(12) United States Patent
Yamada et al.

(10) Patent No.: US 7,521,181 B2
(45) Date of Patent: Apr. 21, 2009

(54) METHODS OF DIAGNOSING RISK OF MYOCARDIAL INFARCTION BY DETECTION OF POLYMORPHISMS IN CONNEXIN AND NADH/NADPH OXIDASE GENES

(75) Inventors: Yoshiji Yamada, Nagoya (JP); Mitsuhiro Yokota, Nagoya (JP)

(73) Assignee: Nagoya Industrial Science Research Institute, Nagoya-shi (JP)

( * ) Notice: Subject to any disclaimer, the term of this patent is extended or adjusted under 35 U.S.C. 154(b) by 776 days.

(21) Appl. No.: 10/517,605

(22) PCT Filed: Mar. 20, 2003

(86) PCT No.: PCT/JP03/03477

§ 371 (c)(1), (2), (4) Date: Dec. 21, 2004

(87) PCT Pub. No.: WO04/001037

PCT Pub. Date: Dec. 31, 2003

(65) Prior Publication Data

US 2005/0260124 A1 Nov. 24, 2005

(30) Foreign Application Priority Data

Jun. 21, 2002 (JP) .............................. 2002-181580

(51) Int. Cl.
*C12Q 1/68* (2006.01)
(52) U.S. Cl. ........................................................ 435/6
(58) Field of Classification Search ...................... 435/6
See application file for complete search history.

(56) References Cited

U.S. PATENT DOCUMENTS

| | | | | |
|---|---|---|---|---|
| 2004/0005566 | A1* | 1/2004 | DePhillipo et al. | 435/6 |
| 2005/0026169 | A1* | 2/2005 | Cargill et al. | 435/6 |
| 2005/0089914 | A1 | 4/2005 | Yamasaki | |
| 2007/0042382 | A1* | 2/2007 | Cargill et al. | 435/6 |

FOREIGN PATENT DOCUMENTS

| | | |
|---|---|---|
| WO | 91/13075 | 9/1991 |
| WO | 01/18250 | 3/2001 |
| WO | 01/79234 | 10/2001 |
| WO | 03/087360 | 10/2003 |

OTHER PUBLICATIONS

Dammerman et al., Proc. Natl. Acad. Sci. USA 90, 4562-4566 (1993).*
Pastinen, T., et al. "Array-based multiplex analysis of candidate genes reveals two independent and additive genetic risk factors for myocardial infarction in the Finnish population;" *Human Molecular Genetics*; vol. 7, No. 9; pp. 1453-1462 (1998).

Li, A., et al. "Relationship of the C242T *p22phox* Gene Polymorphism to Angiographic Coronary Artery Disease and Endothelial Function;" *American Journal of Medical Genetics*; vol. 86, pp. 57-61 (1999).
Rauramaa, R., et al. "Stromelysin-1 and Interleukin-6 Gene Promoter Polymorphisms Are Determinants of Asymptomatic Carotid Artery Atherosclerosis;" *Arterioscler Thromb Vasc Biol.*; vol. 20; pp. 2657-2662 (2000).
Humphries, S., et al. "The 5A/6A polymorphism in the promoter of the stromelysin-1 (MMP-3) gene predicts progression of angiographically determined coronary artery disease in men in the LOCAT gemfibrozil study;" *Atherosclerosis*; vol. 139, pp. 49-56 (1998).
Ye, S., et al. "Progression of Coronary Atherosclerosis Is Associated with a Common Generic Variant of the Human Stromelysin-1 Promoter Which Results in Reduced Gene Expression;" *The Journal of Biological Chemistry*; vol. 271, No. 22. pp. 13055-13060 (1996).
Boekholdt, S., et al. "Genetic Variation in Coagulation and Fibrinolytic Proteins and Their Relation With Acute Myocardial Infarction;" *Circulation*; vol. 104, pp. 3063-3068 (2001).
Yamada, Y., et al. "Prediction of the Risk of Myocardial Infarction From Polymorphisms in Candidate Genes;" *The New England Journal of Medicine*; vol. 347, No. 24, pp. 1916-1923 (2002).
Grutters, J., et al. "Increased Frequency of the Uncommon Tumor Necrosis Factor-857T allele in British and Dutch Patients with Sarcoidosis;" *American Journal of Respiratory and Critical Care Medicine*; vol. 165, pp. 1119-1124 (2002).
Igaku Daijiten, 1985, pp. 12,488-12,489.
P. M. Ridker, et al., "Elevation of Tumor Necrosis Factor- $\alpha$ and Increased Risk of Recurrent Coronary Events After Myocardial Infraction," Circulation, 2000, vol. 101, pp. 2149-2153.
Office Action mailed Jan. 22, 2008, issued in the proceeding of a corresponding Japanese patent application and its partial translation.
The European Patent Office Communication (including Supplementary Partial European Search Report) for corresponding European patent application No. 03712817(PCT/JP0303477), dated Oct. 13, 2005.

(Continued)

*Primary Examiner*—Kenneth R. Horlick
(74) *Attorney, Agent, or Firm*—Edwards Angell Palmer & Dodge LLP

(57) ABSTRACT

It is intended to provide a means of diagnosing myocardial infarction which shows a high accuracy and a high predictability. The risk of myocardial infarction is diagnosed by a method comprising the following steps: (i) the step of analyzing 2 or more polymorphisms among 10 gene polymorphisms or 5 gene polymorphisms proved as relating to myocardial infarction; (ii) the step of determining the genotype of a nucleic acid sample based on the polymorphism data obtained in the above step; and (iii) the step of determining the genetic risk of myocardial infarction from the genotype thus obtained.

1 Claim, 13 Drawing Sheets

OTHER PUBLICATIONS

Hung-I. Yeh, et al. "Connexin37 gene polymorphism and coronary artery disease in Taiwan;" *International Journal of Cardiology*; vol. 81, pp. 251-255 (2001).

Werner Koch, et al. "Interleukin-10 and tumor necrosis factor gene polymorphisms and risk of coronary artery disease and myocardial infarction;" *Atherosclerosis*; vol. 159, pp. 137-144 (2001).

M. Boerma, et al. "A genetic polymorphism in connexin 37 as a prognostic marker for atherosclerotic plaque development;" *Journal of Internal Medicine*; vol. 246, pp. 211-218 (1999).

Elvis Brscic, et al. "Acute myocardial infarction in young adults: Prognostic role of angiotensin-converting enzyme, angiotensin II type I receptor, apolipoprotein E, endothelial constitutive nitric oxide synthase, and glycoprotein IIIa genetic polymorphisms at medium-term follow-up;" *American Heart Journal*; vol. 139, No. 6, pp. 979-984 (2000).

Juliano C. Padovani, et al. "Gene Polymorphisms in the TNF Locus and the Risk of Myocardial Infarction;" *Thrombosis Research*; vol. 100, pp. 263-269 (2000).

M.E. Marenberg, et al.; "Genetic Susceptibility to Death From Coronary Heart Disease in a Study of Twins;" *The New England Journal of Medicine*; vol. 330; No. 15; Apr. 14, 1994; pp. 1041-1046.

J.J. Nora, et al.; "Genetic-Epidemiologic Study of Early-onset Ischemic Heart Disease;" *Circulation*; vol. 61; No. 3; Mar. 1980; pp. 503-508.

U. Broeckel, et al.; "A comprehensive linkage analysis for myocardial infarction and its related risk factors;" *Nature Genetics*; vol. 30; Feb. 2002; pp. 210-214.

F. Cambien, et al.; "Detection polymorphism in the gene for angiotensin-converting enzyme is a potent risk factor for myocardial infarction;" *Nature*; vol. 359; Oct. 15, 1992; pp. 641-644.

E. J. Weiss, et al; "A Polymorphism of a Platelet Glycoprotein Receptor as an Inherited Risk Factor for Coronary Thrombosis;" *The New England Journal of Medicine*; vol. 334; No. 17; Apr. 25, 1996; pp. 1090-1094.

L. Iacoviello, et al.; "Polymorphisms in the Coagulation Factor VII Gene and the Risk of Myocardial Infarction;" *The New England Journal of Medicine*; vol. 338; No. 2; Jan. 8, 1998; pp. 79-85.

J.A. Kuivenhoven, et al., "The Role of a Common Variant of the Cholesteryl Ester Transfer Protein Gene in the Progression of Coronary Atherosclerosis;" *The New England Journal of Medicine*; vol. 338; No. 2; Jan. 8, 1998; pp. 86-93.

M. Boerma, et al.; "A genetic polymorphism in connexin 37 as a prognostic marker for atherosclerotic plaque development;" *Journal of Internal Medicine*; vol. 246; 1999; pp. 211-218.

N. Inoue, et al.; "Polymorphism of the NADH/NADPH Oxidase *p22 phox* Gene in Patients With Coronary Artery Disease;" *Circulation*; vol. 97; 1998; pp. 135-137.

E.J. Topol, et al; "Single Nucleotide Polymorphisms in Multiple Novel Thrombospondin Genes May Be Associated With Familial Premature Myocardial Infarction:" *Circulation*; vol. 104; Nov. 27, 2001; pp. 2641-2644.

T. Skoog, et al.; "A common functional polymorphism (C→A substitution at position - 863) in the promoter region of the tumour necrosis factor-α (TNF-α) gene associated with reduced circulating levels of TNF-α;" *Human Molecular Genetics*; vol. 8; No. 8; 1999; pp. 1443-1449.

Y. Yamada, et al.; "Identification of the $G^{994}$→T Missense Mutation in Exon 9 of the Plasma Platelet-Activating Factor Acetylhydrolase Gene as an Independent Risk Factor for Coronay Artery Disease in Japanese Men;" *Metabolism*; vol. 47; No. 2; Feb. 1998; pp. 177-181.

W. Koch, et al.; "Interleukin-10 and tumor necrosis factor gene polymorphisms and risk of coronary artery disease and myocardial infraction;" *Artherosclerosis*; vol. 159; 2001; pp. 137-144.

I. Inoue, et al.' "A Nucleotide Substitution in the Promotor of Human Angiotensinogen Is Associated with Essential Hypertension and Affects Basal Transcription In Vitro;" *J. Clin. Invest*; vol. 99; No. 7; Apr. 1997; pp. 1786-1797.

J.-C. Lambert, et al.; "Independent association of an APOE gene promoter polymorphism with increased risk of myocardial infarction and decreased APOE plasma concentrations—the ECTIM study;" *Human Molecular Genetics*; vol. 9; No. 1; 2000; pp. 57-61.

M. Eto, et al.; "Increased frequencies of apolipoprotein ϵ2 and ϵ4 alleles in patients with ischemic heart disease;" *Clinical Genetics*; vol. 36; 1989; pp. 183-188.

J. Ruiz, et al.; "Gln-Arg192 polymorphism of paraoxonase and coronary heart disease in type 2 diabetes;" *The Lancet*; vol. 346; Sep. 30, 1995; pp. 869-872.

M. Murata, et al.; "Coronary Artery Disease and Polymorphisms in a Receptor Mediating Shear Stress-Dependent Platelet Activation;" *Circulation*; vol. 96; No. 10; Nov. 18, 1997; pp. 3281-3286.

P. Eriksson, et al.; "Allele-specific increase in basal transcription of the plasminogen-activator inhibitor 1 gene is associated with myocardial infarction;" *Proc. Natl. Acad. Sci. USA*; vol. 92; Mar. 1995; pp. 1851-1855.

S. Ye, et al.; "Preliminary report: genetic variation in the human stromelysin promoter is associated with progression of coronary atherosclerosis;" *Br Heart J*; vol. 73; 1995; pp. 209-215.

R.W. Mahley; "Apolipoprotein E: Cholesterol Transport Protein with Expanding Role in Cell Biology;" *Science*; vol. 240; Apr. 29, 1988; pp. 622-630.

W.J. Schneider, et al.; "Familial Dysbetalipoproteinemia. Abnormal Binding of Mutant Apoprotein E to Low Density Lipoprotein Receptors of Human Fibroblasts and Membranes from Liver and Adrenal of Rats, Rabbits, and Cows;" *J. Clin. Invest.*; vol. 68; Nov. 1981; pp. 1075-1085.

R.E. Gregg, et al.; "Type III Hyperlipoproteinemia: Defective Metabolism of an Abnormal Apolipoprotein E;" *Science*; vol. 211; Feb. 6, 1981; pp. 584-586.

J.L. Breslow, et al.; "Studies of familial type III hyperlipoproteinemia using as a genetic marker the apoE phenotype E2/2;" *Journal of Lipid Research*; vol. 23; 1982; pp. 1224-1235.

P.M. Sullivan, et al.; "Type III Hyperlipoproteinemia and Spontaneous Atherosclerosis in Mice Resulting from Gene Replacement of Mouse *Apoe* with Human *APOE*2;"* *The Journal of Clinical Investigation*; vol. 102; No. 1; Jul. 1998; pp. 130-135.

S.S. Kumari, et al.; "Functional Expression and Biophysical Properties of Polymorphic Variants of the Human Gap Junction Protein Connexin37;" *Biochemical and Biophysical Research Communications*; vol. 274; No. 1; 2000; pp. 216-224.

E. Dupont, et al.; "Altered Connexin Expression in Human Congestive Heart Failure;" *J Mol Cell Cardiol*; vol. 33; 2001; pp. 359-371.

S. Kumari, et al.; "Two Polymorphic Variants of Human Connexin37 Exhibit Different Biophysical Properties;" *Molecular Biology of the Cell*; vol. 9 (Suppl.); Nov. 1998; pp. 93a 538.

K.E. Reed, et al.; "Molecular cloning and functional expression ofhuman connexin37, an endothelial cell gap junction protein;" *J. Clin. Invest.*; vol. 93; No. 2; 1993; pp. 997-1004.

* cited by examiner

Fig.1

| gene | polymorphism | gene | polymorphism |
|---|---|---|---|
| Angiotensin converting enzyme | I/D in intron 16 | Insulin receptor substrate-1 | 3494G→A (Gly972Arg) |
| Angiotensin II type I receptor | -535C→T | Interleukin-10 | -1082G→A |
| Angiotensinogen | -6G→A | | -819T→C |
| Apolipoprotein A1 | -75G→A | | -592A→C |
| | 83C→T | | -889C→T |
| Apolipoprotein B | I/D in signal peptide | Interleukin-1α | -511C→T |
| Apolipoprotein C-III | -482C→T | Interleukin-1β | 3953C→T |
| | 1100C→T | Interleukin-6 | -634C→G |
| Apolipoprotein E | -491A→T | | -174G→C |
| | -219G→T | LDL receptor related protein | 766C→T |
| | 3932T→C (Cys112Arg) | Leptin | -1887C→A |
| | 4070C→T (Arg158Cys) | Lipoprotein lipase | 280G→A (Asp9Asn) |
| Apolipoprotein (a) | 93C→T | | 1127A→G (Asn291Ser) |
| | 121G→A | Manganese superoxide dismutase | 47C→T (Ala16Val) |
| | 11764A→C (Thr12Pro) | | 173T→C (Ile58Thr) |
| ATP-binding cassette transporter 1 | -477C→T | Matrix Gla protein | -7G→A |
| | 1051G→A (Arg219Lys) | | 7158A→G (Thr83Ala) |
| Atrial natriuretic peptide | 664G→A (Val7Met) | Metalloproteinase-1 (collagenase) | -1607G→GG |
| Atrial natriuretic peptide clearance receptor | -55A→C | Metalloproteinase-12 (macrophage elastase) | -82A→G |
| β2-adrenergic receptor | 46A→G (Arg16Gly) | Methionine synthase | 2756A→G (Asp919Gly) |
| | 79C→G (Gln27Glu) | Methylenetetrahydrofolate reductase | 677C→T (Ala222Val) |
| | 491C→T (Thr164Ile) | Monocyte chemoattractant protein-1 | -2518G→A |
| β3-adrenergic receptor | 190T→C (Trp64Arg) | NADH/NADPH oxidase p22 phox | 242C→T (His72Tyr) |
| β-Fibrinogen | -854G→A | Neuropeptide Y | 1128T→C (Leu7Pro) |
| | -455G→A | Paraoxonase | -107T→C |
| | 148C→T | | 172A→T (Met55Leu) |
| | 8059G→A (Arg448Lys) | | 584G→A (Gln192Arg) |
| CD14 receptor | -260C→T | PECAM1 (CD31) | 1454C→G (Leu125Val) |

Fig.2

| | | | |
|---|---|---|---|
| Chemokine receptor 2 | 190G→A (Val64Ile) | PECAM1 (CD31) | 4428G→A (Ser563Asn) |
| Cholesterol ester transfer protein | 1061A→G (Ile405Val) | Peroxisome proliferator-activated receptor-α | 696C→G (Leu162Val) |
| | 1163A→G (Asp442Gly) | Peroxisome proliferator-activated receptor -γ2 | 34C→G (Pro12Ala) |
| | 1200G→A (Arg451Gln) | | 344C→A (Pro115Gln) |
| Coagulation factor V | 1691G→A (Arg506Gln) | Plasminogen-activator inhibitor-1 | −668/4G→5G |
| Coagulation factor VII | 11496G→A (Arg353Glu) | Platelet-activating factor acetylhydrolase | 994G→T (Val279Phe) |
| Coagulation factor XII | 46C→T | Prothrombin | 20210G→A |
| Coagulation factor XIII A-subunit | 163G→T (Val34Leu) | P-selectin | 76666A→C (Thr715Pro) |
| Connexin 37 | 1019C→T (Pro319Ser) | Scavenger receptor-BI | 4G→A (Gly2Ser) |
| Endothelial nitric oxide synthase | −786T→C | | 403G→A (Val135Ile) |
| | 894G→T (Glu298Asp) | Serotonin 2A receptor | 102T→C |
| Endothelin-1 | 5665G→T (Lys198Asn) | Stromelysin-1 | −1171/5A→6A |
| E-selectin | 98G→T | Thrombomodulin | −33G→A |
| | 561A→C (Ser128Arg) | | −10GG→TA |
| | 1839C→T (Leu554Phe) | | 845G→A (Ala25Thr) |
| Extracellular superoxide dismutase | 5775C→G (Arg213Gly) | | 2136C→T (Ala455Val) |
| Fatty acid-binding protein 2 | 2445G→A (Ala54Thr) | Thrombopoietin | 5713A→G |
| Fractalkine receptor | 84635G→A (Val249Ile) | Thrombospondin 1 | 2210A→G (Asn700Ser) |
| Glycoprotein Ia | 807C→T | Thrombospondin 4 | 1186G→C (Ala387Pro) |
| | 873G→A | Tissue factor pathway inhibitor | 874G→A (Val264Met) |
| Glycoprotein Ibα | 1648A→G (Lys505Glu) | Transforming growth factor-β1 | −509C→T |
| Glycoprotein IIIa | 1018C→T (Thr145Met) | | 869T→C (Leu10Pro) |
| Glycoprotein PC-1 | 1565T→C (Leu33Pro) | Tumor necrosis factor-α | −863C→A |
| G-protein β3 subunit | 97A→C (Lys121Gln) | | −850C→T |
| Hemochromatosis-associated protein | 825C→T (splice variant) | | −308G→A |
| | 845G→A (Cys282Tyr) | | −238G→A |
| Hepatic lipase | −480C→T | von Willebrand factor | −1234C→T |
| | −250G→A | | −1051G→A |

Fig.3

| gene | SNP | label | primer | frequency | probe | formamide |
|------|-----|-------|--------|-----------|-------|-----------|
| | | | annealing temperature, 55-67.5°C; Mg, 1-4 mM | | | |
| Platelet-activatibg factor acetylhydrolase | 994G→T | FITC | TTCTTTTGGTGGAGCAACXGT | | | |
| | | TxR | ATTCTTTTGGTGGAGCAACXTT | 40 | | |
| | | biotin | TCTTACCTGAATCTCTGATCTTCA | | | |
| NADH/NADPH oxidase p22 phox | 242C→T | FITC | ACCACGGGCGGTCATGXGC | | | |
| | | TxR | ACCACGGCGGTCATGXAC | 40 | | |
| | | biotin | GCAGCAAAGGAGTCCCGAGT | | | |
| Connexin 37 | 1019C→T | TxR | CTCAGAAATGGCCAAAAXCC | | | |
| | | FITC | CCTCAGAATGGCCAAAAXTC | 35 | | |
| | | biotin | GCAGAGCTGCTGGGACGA | | | |
| Angiotensinogen | -6G→A | TxR | CGGCAGCTTCTTCCCXCG | | | |
| | | FITC | CGGCAGCTTCTTCCCXTG | 35 | | |
| | | biotin | CCACCCCTCAGCTATAAATAGG | | | |
| Tumor necrosis factor-α | -863C→A | TxR | GGCCCTGTCTTCGTTAAXGG | | | |
| | | FITC | ATGGCCCTGTCTTCGTTAAXTG | 35 | | |
| | | biotin | CCAGGGCTATGGAAGTCGAGTATC | | | |
| Apolipoprotein C-III | -482C→T | FITC | CGGAGCCACTGATGCXCG | | AGCCACTGATGCXCGGTCT | |
| | | | CGGAGCCACTGATGCXTG | 35 | AGCCACTGATGCXTGGTCT | 30% |
| | | biotin | TGTTTGGAGTAAAGGCACAGAA | | | |
| Interleukin-10 | -592A→C | FITC | CAGAGACTGGCTTCCTACAXGA | | | |
| | | TxR | CCAGAGACTGGCTTCCTACAXTA | 35 | | |
| | | biotin | GCCTGGAACACATCCTGTGA | | | |

Fig.4

| Gene | Mutation | Label | Sequence | | |
|---|---|---|---|---|---|
| Apolipoprotein E | -219G→T | FITC | GAATGGAGGAGGGTGTCTXGA | | |
| | | TxR | AGAATGGAGGAGGGTGTCTXTA | 35 | |
| | | biotin | CCAGGAAGGGAGGACACCTC | | |
| Interleukin-10 | -819T→C | FITC | TACCCTTGTACAGGTGATGTAXTA | 35 | GTACAGGTGATGTAXTATCTCTGTG |
| | | TxR | TACCCTTGTACAGGTGATGTAXCA | 35 | GTACAGGTGATGTAXCATCTCTGTG 40% |
| | | biotin | ATAGTGAGCAAACTGAGGCACA | | |
| Thrombospondin 4 | 1186G→C | TxR | CGAGTTGGGAACGCACXCT | 35 | |
| | | FITC | CGAGTTGGGAACGCACXGT | | |
| | | biotin | GGTCTGCACTGACATTGATGAG | | |
| Paraoxonase | 584G→A | FITC | ACCCAAATACATCTCCCAGGAXCG | 35 | |
| | | TxR | AACCCAAATACATCTCCCAGGXCT | | |
| | | biotin | GAATGATATTGTTGCTGTGTGGAC | | |
| Apolipoprotein E | 4070C→T | FITC | CCGATGACCTGCAGAAXCG | 40 | |
| | | TxR | GCCGATGACCTGCAGAAXTG | | |
| | | biotin | CGGCCTGGTACACTGCCAG | | |
| Plasminogen activator inhibitor-1 | -668/4G→5G | biotin | GGCACAGAGAGTCTGGACACG | 35 | TGGACACGTGGGGGAGTCAG |
| | | FITC | GGCCGCCTCCGATGATACA | | TGGACACGTGGGGGAGTCAGC 45% |
| Stromelysin-1 | -1171/5A→6A | TxR | TTTGATGGGGGAAAAXCC | 40 | |
| | | biotin | TTGATGGGGGAAAAAXCC | | |
| Glycoprotein Iba | 1018C→T | FITC | CCTCATATCAATGTGGCAA | 40 | |
| | | TxR | CCCAGGGCTCCTGXCG | | |
| | | biotin | CCCCAGGGCTCCTGXTG | | |
| | | | TGAGCTTCTCCAGCTTGGGTG | | |

Fig.5

|  | male (n = 451) | | female (n = 458) | |
|---|---|---|---|---|
|  | control (n = 232) | myocardial infarction case (n = 219) | control (n = 232) | myocardial infarction case (n = 226) |
| age (years) | 52.4 ± 3.6 | 51.8 ± 6.0 | 62.6 ± 8.8 | 62.2 ± 8.3 |
| Body mass index (kg/m$^2$) | 23.8 ± 2.5 | 24.2 ± 2.7 | 23.4 ± 3.2 | 23.2 ± 2.9 |
| smoking (%) | 60.3 | 60.7 | 9.5 | 16.5*1 |
| hypertension (%) | 43.5 | 42.9 | 69.8 | 65.5 |
| diabetes (%) | 11.2 | 16.0 | 15.5 | 36.7† |
| hypercholesterolemia (%) | 45.3 | 52.5 | 59.9 | 66.8 |
| hyperuricemia (%) | 16.4 | 21.0 | 10.3 | 11.9 |

Fig.6

| gene | polymorphism | genetic model | P | gene | polymorphism | genetic model | P |
|---|---|---|---|---|---|---|---|
| male | | | | female | | | |
| Platelet-activating factor acetylhydrolase | 994G→T | additive | 0.0006 | Paraoxonase | 584G→A | dominant | 0.009 |
| NADH/NADPH oxidase p22 phox | 242C→T | dominant | 0.006 | Interleukin-6 | -634C→G | additive | 0.009 |
| Connexin 37 | 1019C→T | additive | 0.007 | Connexin 37 | 1019C→T | dominant | 0.013 |
| Thrombospondin 4 | 1186G→C | dominant | 0.013 | ATP-binding cassette transporter 1 | 1051G→A | additive | 0.014 |
| Angiotensinogen | -6G→A | recessive | 0.019 | Tumor necrosis factor-α | -850C→T | additive | 0.015 |
| Tumor necrosis factor-α | -863C→A | dominant | 0.045 | Endothelin-1 | 5665G→T | recessive | 0.028 |
| Transforming growth factor-β1 | 869T→C | additive | 0.049 | Apolipoprotein E | 4070C→T | recessive | 0.038 |
| G-protein β3 subunit | 825C→T | additive | 0.051 | Apolipoprotein C-III | -482C→T | recessive | 0.044 |
| Apolipoprotein C-III | -482C→T | recessive | 0.057 | Apolipoprotein E | 3932T→C | dominant | 0.047 |
| Interleukin-10 | -819T→C | recessive | 0.061 | CD14 receptor | -260C→T | additive | 0.050 |
| Thrombomodulin | 2136C→T | additive | 0.065 | Tumor necrosis factor-α | -238G→A | dominant | 0.052 |
| Apolipoprotein E | 4070C→T | additive | 0.074 | Plasminogen-activator inhibitor-1 | -668/4G→5G | recessive | 0.055 |
| Glycoprotein Ia | A1648→G | recessive | 0.080 | Fatty acid-binding protein 2 | 2445G→A | additive | 0.057 |
| Interleukin-10 | -592A→C | recessive | 0.088 | Insulin receptor substrate-1 | 3494G→A | dominant | 0.058 |
| Apolipoprotein E | -219G→T | recessive | 0.092 | Stromelysin-1 | -1171/5A→6A | additive | 0.072 |
| Thrombopoietin | 5713A→G | recessive | 0.094 | Glycoprotein Ibα | 1018C→T | additive | 0.072 |
| Apolipoprotein C-III | 1100C→T | recessive | 0.095 | E-selectin | A561→C | dominant | 0.074 |
| Chemokine receptor 2 | 190G→A | recessive | 0.097 | Endothelial nitric oxide synthase | -786T→C | dominant | 0.087 |
| Endothelial nitric oxide synthase | -786T→C | dominant | 0.098 | | | | |

Fig.7

|  | male (n = 3309) | | female (n = 1752) | |
|---|---|---|---|---|
|  | control (n = 1306) | myocardial infarction case (n = 2003) | control (n = 936) | myocardial infarction case (n = 816) |
| Age (years) | 60.1 ± 9.6 | 60.8 ± 10.3 | 60.8 ± 11.2 | 60.5 ± 10.6 |
| Body mass index (kg/m$^2$) | 23.6 ± 2.6 | 23.6 ± 2.9 | 23.0 ± 3.3 | 23.4 ± 3.5*1 |
| Smoking (%) | 57.6 | 58.2 | 9.5 | 15.5*2 |
| Hypertension (%) | 53.6 | 45.0*2 | 59.4 | 55.9 |
| Diabetes mellitus (%) | 15.4 | 32.4*2 | 16.5 | 42.1*1 |
| Hypercholesterolemia (%) | 35.4 | 43.7*2 | 51.2 | 56.8*3 |
| Hyperuricemia (%) | 17.2 | 14.2*3 | 9.7 | 13.2*1 |

Fig.8

| gene | polymorphism | distribution of genotype (%) | | | | | |
|---|---|---|---|---|---|---|---|
| | | control | | | myocardial infarction case | | |
| male (n = 3309) | | | | | | | |
| Connexin 37 | 1019C→T | CC, 72.5 | CT, 22.7 | TT, 4.9 | CC, 66.3 | CT, 28.8 | TT, 4.9 |
| Tumor necrosis factor-α | -863C→A | CC, 70.9 | CA, 20.7 | AA, 8.5 | CC, 75.5 | CA, 17.9 | AA, 6.6 |
| NADH/NADPH oxidase p22 phox | 242C→T | CC, 74.8 | CT, 24.2 | TT, 1.0 | CC, 79.7 | CT, 19.0 | TT, 1.3 |
| Angiotensinogen | -6G→A | GG, 2.6 | GA, 29.6 | AA, 67.8 | GG, 4.3 | GA, 33.4 | AA, 62.3 |
| Apolipoprotein E | -219G→T | GG, 8.4 | GT, 42.7 | TT, 48.9 | GG, 7.2 | GT, 39.2 | TT, 53.6 |
| Platelet-activating factor acetylhydrolase | 994G→T | GG, 71.2 | GT, 26.3 | TT, 2.5 | GG, 68.1 | GT, 29.2 | TT, 2.6 |
| Apolipoprotein C-III | -482C→T | CC, 28.1 | CT, 48.4 | TT, 23.5 | CC, 27.5 | CT, 51.2 | TT, 21.3 |
| Thrombospondin 4 | 1186G→C | GG, 88.1 | GC, 11.8 | CC, 0.1 | GG, 85.4 | GC, 14.0 | CC, 0.5 |
| Interleukin-10 | -819T→C | TT, 47.2 | TC, 42.4 | CC, 10.4 | TT, 47.2 | TC, 39.6 | CC, 13.1 |
| Interleukin-10 | -592A→C | AA, 47.5 | AC, 41.8 | CC, 10.6 | AA, 46.2 | AC, 40.4 | CC, 13.4 |
| female (n = 1752) | | | | | | | |
| Stromelysin-1 | -1171/5A→6A | 5A/5A, 1.2 | 5A/6A, 47.1 | 6A/6A, 51.7 | 5A/5A, 1.8 | 5A/6A, 37.9 | 6A/6A, 60.2 |
| Plasminogen activator inhibitor-1 | -668/4G→5G | 4G/4G, 43.8 | 4G/5G, 44.2 | 5G/5G, 12.0 | 4G/4G, 37.3 | 4G/5G, 49.6 | 5G/5G, 13.1 |
| Glycoprotein Ibα | 1018C→T | CC, 76.7 | CT, 20.8 | TT, 2.5 | CC, 77.7 | CT, 21.6 | TT, 0.7 |
| Paraoxonase | 584G→A | GG, 44.7 | GA, 45.0 | AA, 10.3 | GG, 44.6 | GA, 41.7 | AA, 13.6 |
| Apolipoprotein E | 4070C→T | CC, 91.2 | CT, 8.7 | TT, 0.1 | CC, 91.8 | CT, 7.2 | TT, 1.0 |

Fig.9

| gene | polymorphism | Dominant | | Recessive | | Additive | |
|---|---|---|---|---|---|---|---|
| | | P | OR (95% CI) | P | OR (95% CI) | P | OR (95% CI) |
| male (n = 3309) | | | | | | | |
| Connexin 37 | 1019C→T | 0.0001 | 1.4 (1.2-1.7) | 0.7834 | | <0.0001 | 1.5 (1.2-1.7) |
| Tumor necrosis factor-α | -863C→A | 0.0020 | 0.7 (0.6-0.9) | 0.0235 | 0.7 (0.5-1.0) | 0.0105 | 0.7 (0.5-0.9) |
| NADH/NADPH oxidase p22 phox | 242C→T | 0.0027 | 0.7 (0.6-0.9) | 0.9462 | | 0.0021 | 0.7 (0.6-0.9) |
| Angiotensinogen | -6G→A | 0.0563 | | 0.0038 | 0.8 (0.7-0.9) | 0.0283 | 0.6 (0.4-0.9) |
| Apolipoprotein E | -219G→T | 0.4015 | | 0.0085 | 1.2 (1.1-1.4) | 0.1557 | |
| Platelet-activating factor acetylhydrolase | 994G→T | 0.0349 | 1.2 (1.0-1.4) | 0.6522 | | 0.0227 | 1.2 (1.0-1.4) |
| Apolipoprotein C-III | -482C→T | 0.6297 | | 0.0367 | 0.8 (0.7-1.0) | 0.2716 | |
| Thrombospondin 4 | 1186G→C | 0.0373 | 1.3 (1.0-1.6) | 0.0834 | | 0.0700 | |
| Interleukin-10 | -819T→C | 0.9108 | | 0.0375 | 1.3 (1.0-1.6) | 0.0738 | |
| Interleukin-10 | -592A→C | 0.2692 | | 0.0427 | 1.3 (1.0-1.6) | 0.0394 | 1.3 (1.0-1.7) |
| female (n = 1752) | | | | | | | |
| Stromelysin-1 | -1171/5A→6A | <0.0001 | 2.1 (1.6-2.8) | 0.0002 | 1.5 (1.2-1.9) | <0.0001 | 2.2 (1.6-2.9) |
| Plasminogen activator inhibitor-1 | -668/4G→5G | 0.0008 | 1.5 (1.2-1.8) | 0.4495 | | 0.0010 | 1.5 (1.2-1.9) |
| Glycoprotein Ibα | 1018C→T | 0.6065 | | 0.0238 | 0.3 (0.1-0.8) | 0.0242 | 0.3 (0.1-0.8) |
| Paraoxonase | 584G→A | 0.3966 | | 0.0349 | 1.4 (1.0-2.0) | 0.1017 | |
| Apolipoprotein E | 4070C→T | 0.6881 | | 0.0399 | 9.7 (1.6-185.6) | 0.0418 | 9.5 (1.6-181.7) |

Fig.10

| gene | locus | polymorphism | genetic model | P | odds ratio | 95% CI |
|---|---|---|---|---|---|---|
| male | | | | | | |
| Connexin 37 | 1p35.1 | 1019C→T | TT + CT versus CC | 0.0124 | 1.31 | 1.06-1.61 |
| Tumor necrosis factor-α | 6p21.3 | -863C→A | AA + CA versus CC | 0.0336 | 0.79 | 0.64-0.98 |
| NADH/NADPH oxidase p22 phox | 16q24 | 242C→T | TT + CT versus CC | 0.2926 | 0.88 | 0.70-1.11 |
| Angiotensinogen | 1q42-q43 | -6G→A | AA versus GA + GG | 0.0251 | 0.79 | 0.65-0.97 |
| Apolipoprotein E | 19q13.2 | -219G→T | TT versus GT + GG | 0.0209 | 1.26 | 1.03-1.51 |
| Platelet-acrivating factor acetylhydrolase | 6p21.2-p12 | 994G→T | TT + GT versus GG | 0.0155 | 1.30 | 1.05-1.59 |
| Apolipoprotein C-III | 11q23 | -482C→T | TT versus CT + CC | 0.0606 | 0.80 | 0.64-1.01 |
| Thrombospondin 4 | 5q13 | 1186G→C | CC + GC versus GG | 0.0011 | 1.64 | 1.22-2.21 |
| Interleukin-10 | 1q31-q32 | -819T→C | CC versus CT + TT | 0.5643 | 1.20 | 0.65-2.17 |
| Interleukin-10 | 1q31-q32 | -592A→C | CC versus CA + AA | 0.6323 | 1.16 | 0.63-2.12 |
| female | | | | | | |
| Stromelysin-1 | 11q23 | -1171/5A→6A | 6A/6A + 5A/6A versus 5A/5A | <0.0001 | 1.87 | 1.42-2.47 |
| Plasminogen activator inhibitor-1 | 7q21.3-q22 | -668/4G→5G | 5G/5G + 4G/5G versus 4G/4G | 0.0005 | 1.50 | 1.19-1.89 |
| Glycoprotein Ibα | 22q11.2 | 1018C→T | TT versus CT + CC | 0.0308 | 0.28 | 0.09-0.89 |
| Paraoxonase | 7q21.3 | 584G→A | AA versus GA + GG | 0.1889 | 1.27 | 0.89-1.81 |
| Apolipoprotein E | 19q13.2 | 4070C→T | TT versus CT + CC | 0.0872 | 6.96 | 0.75-64.36 |

Fig.11

| Thrombospondin 4 (0 = GG, 1 = GC = CC) | Connexin 37 (0 = CC, 1 = CT = TT) | Platelet-activating factor acetylhydrolase (0 = GG, 1 = GT = TT) | Angiotensinogen (0 = GA = GG, 1 = AA) | Tumor necrosis factor-α (0 = CC, 1 = CA = AA) | odds ratio |
|---|---|---|---|---|---|
| 1 | 1 | 1 | 0 | 0 | 4.50 |
| 1 | 1 | 1 | 0 | 1 | 3.55 |
| 1 | 1 | 1 | 1 | 0 | 3.55 |
| 1 | 1 | 1 | 1 | 1 | 2.79 |
| 1 | 1 | 0 | 0 | 0 | 3.47 |
| 1 | 1 | 0 | 0 | 1 | 2.73 |
| 1 | 1 | 0 | 1 | 0 | 2.73 |
| 1 | 1 | 0 | 1 | 1 | 2.15 |
| 1 | 0 | 1 | 0 | 0 | 3.44 |
| 1 | 0 | 1 | 0 | 1 | 2.71 |
| 1 | 0 | 1 | 1 | 0 | 2.71 |
| 1 | 0 | 1 | 1 | 1 | 2.13 |
| 1 | 0 | 0 | 0 | 0 | 2.65 |
| 1 | 0 | 0 | 0 | 1 | 2.08 |
| 1 | 0 | 0 | 1 | 0 | 2.08 |
| 1 | 0 | 0 | 1 | 1 | 1.64 |
| 0 | 1 | 1 | 0 | 0 | 2.75 |
| 0 | 1 | 1 | 0 | 1 | 2.16 |
| 0 | 1 | 1 | 1 | 0 | 2.16 |
| 0 | 1 | 1 | 1 | 1 | 1.70 |
| 0 | 1 | 0 | 0 | 0 | 2.11 |
| 0 | 1 | 0 | 0 | 1 | 1.66 |
| 0 | 1 | 0 | 1 | 0 | 1.66 |
| 0 | 1 | 0 | 1 | 1 | 1.31 |
| 0 | 0 | 1 | 0 | 0 | 2.10 |
| 0 | 0 | 1 | 0 | 1 | 1.65 |
| 0 | 0 | 1 | 1 | 0 | 1.65 |
| 0 | 0 | 1 | 1 | 1 | 1.30 |
| 0 | 0 | 0 | 0 | 0 | 1.61 |
| 0 | 0 | 0 | 0 | 1 | 1.27 |
| 0 | 0 | 0 | 1 | 0 | 1.27 |
| 0 | 0 | 0 | 1 | 1 | 1.00 |

Fig. 12

| Apolipoprotein E (0 = CC = CT, 1 = TT) | Glycoprotein Ibα (0 = CC = CT, 1 = TT) | Stromelysin-1 (0 = 5A/5A, 1 = 5A/6A = 6A/6A) | Plasminogen activator inhibitor-1 (0 = 4G/4G, 1 = 4G/5G = 5G/5G) | Paraoxonase (0 = GG = GA, 1 = AA) | odds ratio |
|---|---|---|---|---|---|
| 1 | 0 | 1 | 1 | 1 | 88.51 |
| 1 | 0 | 1 | 1 | 0 | 69.70 |
| 1 | 0 | 1 | 0 | 1 | 59.01 |
| 1 | 0 | 1 | 0 | 0 | 46.46 |
| 1 | 0 | 0 | 1 | 1 | 47.33 |
| 1 | 0 | 0 | 1 | 0 | 37.27 |
| 1 | 0 | 0 | 0 | 1 | 31.56 |
| 1 | 0 | 0 | 0 | 0 | 24.85 |
| 1 | 1 | 1 | 1 | 1 | 24.79 |
| 1 | 1 | 1 | 1 | 0 | 19.52 |
| 1 | 1 | 1 | 0 | 1 | 16.53 |
| 1 | 1 | 1 | 0 | 0 | 13.02 |
| 1 | 1 | 0 | 1 | 1 | 13.26 |
| 1 | 1 | 0 | 1 | 0 | 10.44 |
| 1 | 1 | 0 | 0 | 1 | 8.84 |
| 1 | 1 | 0 | 0 | 0 | 6.96 |
| 0 | 0 | 1 | 1 | 1 | 12.72 |
| 0 | 0 | 1 | 1 | 0 | 10.01 |
| 0 | 0 | 1 | 0 | 1 | 8.48 |
| 0 | 0 | 1 | 0 | 0 | 6.68 |
| 0 | 0 | 0 | 1 | 1 | 6.80 |
| 0 | 0 | 0 | 1 | 0 | 5.36 |
| 0 | 0 | 0 | 0 | 1 | 4.53 |
| 0 | 0 | 0 | 0 | 0 | 3.57 |
| 0 | 1 | 1 | 1 | 1 | 3.56 |
| 0 | 1 | 1 | 1 | 0 | 2.81 |
| 0 | 1 | 1 | 0 | 1 | 2.37 |
| 0 | 1 | 1 | 0 | 0 | 1.87 |
| 0 | 1 | 0 | 1 | 1 | 1.91 |
| 0 | 1 | 0 | 1 | 0 | 1.50 |
| 0 | 1 | 0 | 0 | 1 | 1.27 |
| 0 | 1 | 0 | 0 | 0 | 1.00 |

Fig.13
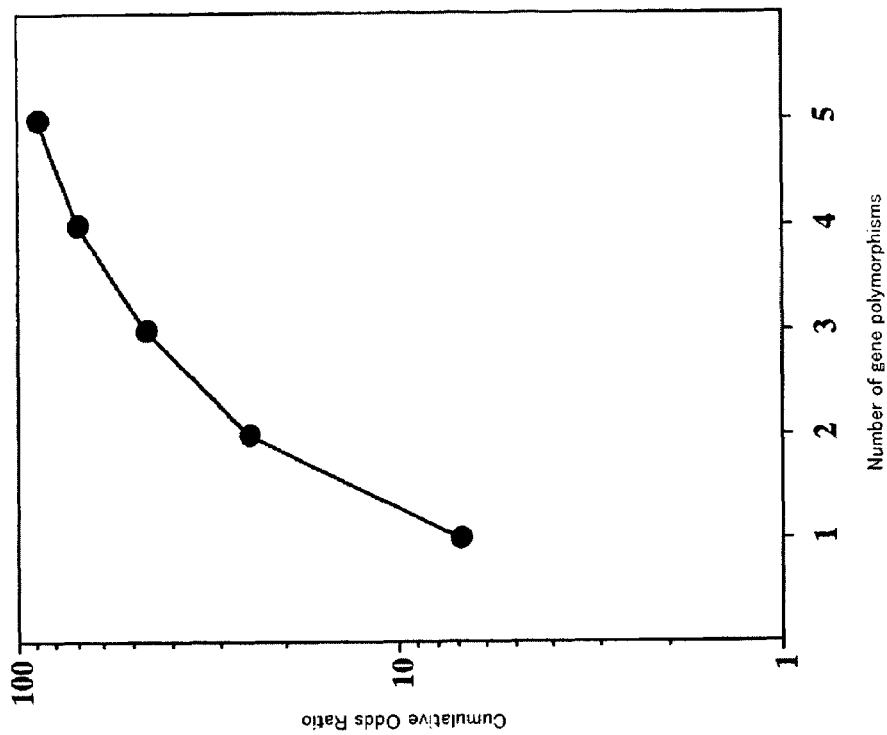
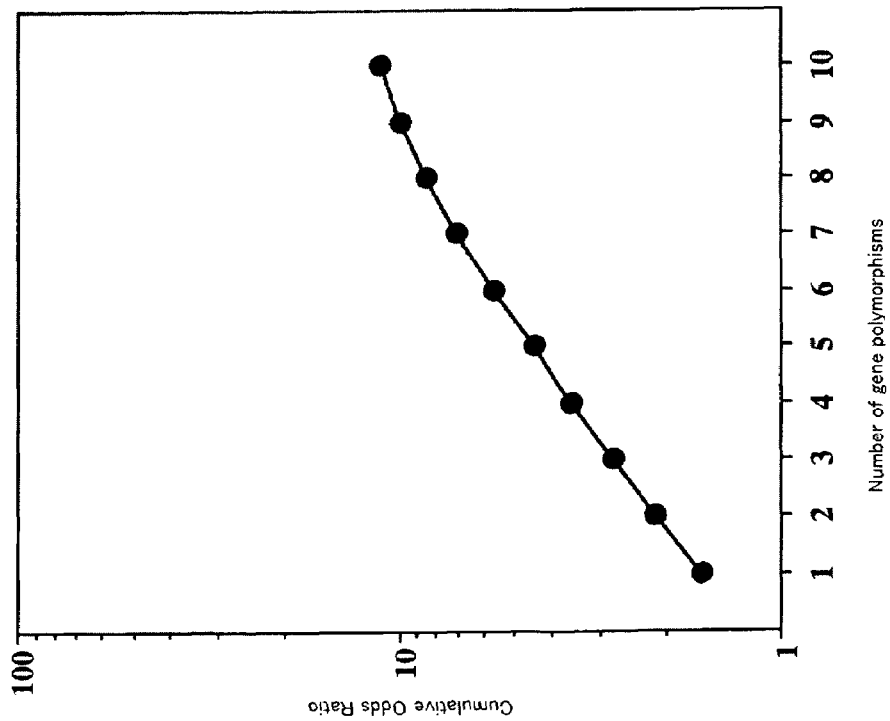

SEQUENCE LISTING

<160> NUMBER OF SEQ ID NOS: 64

<210> SEQ ID NO 1
<211> LENGTH: 1601
<212> TYPE: DNA
<213> ORGANISM: Homo sapiens

<400> SEQUENCE: 1

```
ctccggccat cgtccccacc tccacctggg ccgcccgcga ggcagcggac ggaggccggg      60
agccatgggt gactggggct tcctggagaa gttgctggac caggtccagg agcactcgac     120
cgtggtgggt aagatctggc tgacggtgct cttcatcttc cgcatcctca tcctgggcct     180
ggccggcgag tcagtgtggg gtgacgagca gtcagatttc gagtgtaaca cggcccagcc     240
aggctgcacc aacgtctgct atgaccaggc cttccccatc tcccacatcc gctactgggt     300
gctgcagttc ctcttcgtca gcacacccac cctggtctac ctgggccatg tcatttacct     360
gtctcggcga gaagagcggc tgcggcagaa ggaggggag ctgcgggcac tgccggccaa     420
ggacccacag gtggagcggg cgctggcggc cgtagagcgt cagatggcca agatctcggt     480
ggcagaagat ggtcgcctgc gcatccgcgg agcactgatg ggcacctatg tcgccagtgt     540
gctctgcaag agtgtgctag aggcaggctt cctctatggc cagtggcgcc tgtacggctg     600
gaccatggag cccgtgtttg tgtgccagcg agcaccctgc ccctacctcg tggactgctt     660
tgtctctcgc cccacggaga agaccatctt catcatcttc atgttggtgg ttggactcat     720
ctccctggtg cttaacctgc tggagttggt gcacctgctg tgtcgctgcc tcagccgggg     780
gatgagggca cggcaaggcc aagacgcacc cccgacccag ggcacctcct cagaccctta     840
cacggaccag gtcttcttct acctcccgt gggcaggg ccctcatccc caccatgccc     900
cacctacaat gggctctcat ccagtgagca gaactgggcc aacctgacca cagaggagag     960
gctggcgtct tccaggcccc ctctcttcct ggacccaccc cctcagaatg gccaaaaacc    1020
cccaagtcgt cccagcagct ctgcttctaa gaagcagtat gtatagaggc ctgtggctta    1080
tgtcacccaa cagaggggtc ctgagaagtc tggctgcctg ggatgccccc tgcccctcc    1140 tggaaggctc tgcagagatg actgggctgg ggaagcagat gcttgctggc catggagcct    1200
cattgcaagt tgttcttgaa cacctgaggc cttcctgtgg cccaccaggc actacggctt    1260
```

-continued

```
cctctccaga tgtgctttgc ctgagcacag acagtcagca tggaatgctc ttggccaagg    1320
gtactggggc cctctggcct tttgcagctg atccagagga acccagagcc aacttacccc    1380
aacctcaccc tatggaacag tcacctgtgc gcaggttgtc ctcaaaccct ctcctcacag    1440
gaaaaggcgg attgaggctg ctgggtcagc cttgatcgca cagacagagc ttgtgccgga    1500
tttggccctg tcaaggggac tggtgccttg ttttcatcac tccttcctag ttctactgtt    1560
caagcttctg aaataaacag gacttgatca caaaaaaaaa a                       1601
```

<210> SEQ ID NO 2
<211> LENGTH: 1178
<212> TYPE: DNA
<213> ORGANISM: Homo sapiens
<220> FEATURE:
<221> NAME/KEY: misc_feature
<222> LOCATION: (881)..(881)
<223> OTHER INFORMATION: n stands for any base

<400> SEQUENCE: 2

```
ggggaagcaa aggagaagct gagaagatga aggaaaagtc aggtctggaa ggggcggggg     60
tcagggagct cctgggagat atggccacat gtagcggctc tgaggaatgg gttacaggag    120
acctctgggg agatgtgacc acagcaatgg gtaggagaat gtccagggct atggaagtcg    180
agtatcgggg acccccccctt aacgaagaca gggccatgta gagggcccca gggagtgaaa    240
gagcctccag gacctccagg tatgaatac aggggacgtt taagaagata tggccacaca    300
ctggggccct gagaagtgag agcttcatga aaaaaatcag ggaccccaga gttccttgga    360
agccaagact gaaaccagca ttatgagtct ccgggtcaga atgaaagaag aaggcctgcc    420
ccagtggtct gtgaattccc ggggtgatt tcactccccg ggctgtccca ggcttgtccc    480
tgctaccccc acccagcctt tcctgaggcc tcaagctgcc accagccccc cagctccttc    540
tccccgcaga cccaaacaca ggcctcagga ctcaacacag cttttccctc caacccgtt     600 ttctctccct caaggactca gctttctgaa gcccctccca gttctagttc tatcttttc     660 ctgcatcctg tctggaagtt agaaggaaac agaccacaga cctggtcccc aaaagaaatg    720
gaggcaatag gttttgaggg gcatgggac ggggttcagc ctccagggtc ctacacacaa    780
atcagtcagt ggcccagaag acccccctcg gaatcggagc agggaggatg gggagtgtga    840
ggggtatcct tgatgcttgt gtgtccccaa cttttcaaat nccgccccc gcgatggaga    900 agaaaccgag acagaaggtg cagggcccac taccgcttcc tccagatgag cttatgggtt    960
tctccaccaa ggaagttttc cgctggttga atgattcttt ccccgccctc ctctcgcccc   1020
agggacatat aaaggcagtt gttggcacac ccagccagca gacgctccct cagcaaggac   1080
agcagaggac cagctaagag ggagagaagc aactgcagac ccccctgaa aacaaccctc    1140 agacgccaca tccctgaca agctgccagg caggttct                            1178
```

<210> SEQ ID NO 3
<211> LENGTH: 971
<212> TYPE: DNA
<213> ORGANISM: Homo sapiens

<400> SEQUENCE: 3

```
ccaggctgca gtgcagtggt gcagctgtga ctcatggcag cctccacctg gctcaggcca     60
ccctcttacc tcagcctctg gagtagctgg gaccacaggc acacaccact gcacctggct    120
tttaaatttt ttgtagagat gagggtctca ctatgttgcc caggctggtc tcaaactcct    180
```

```
gggctccagt gatcctcccg cctcagcctc ccaaaatgct gggattccag gcatgagcca    240
ccgtgctcgg gcccctctct gtgttgtctt cagtaaaggg agttcccgt ggcccctcag     300 gctgagctgg gctgttcctt aaccacatgg cttcagtgtg gcgggcgtgt ttgtgtgcct    360
gctggagtac ccccggggga agaggaagaa gggctccacc atggagcgct ggtgagtctc    420
ctcctgatct ggggtctctc cggggctgc ggggcccagg cagggctcac agggttgggt     480
ggagcttggt ttctcacttg gaggctccgg aaccaaccct ttggtgcttg tgggtaaacc    540
aaggccggtg cctgcccggt gtgttttgtg ggaggaaaga ggcctgggtg ccctggggtg    600
gtcagcaggg cagcaaagga gtcccgagtg ggagaggccc agccgcgccg tctcgccttc    660
ctccctcccc caggggacag aagtacatga ccgccgtggt gaagctgttc gggcccttta    720
ccaggaatta ctatgttcgg gccgtcctgc atctcctgtg agtccccgtc ccgcaccccc    780
tctagggctc aggagggctt ggagccgacc ctccccactg tcccaccggc cgggctgcct    840
ggacaggagc cacccccact tacctcagtg ttttttccaaa caaaaattcg ggtccctggc   900
tctggcaggg cctgtgtctg ctgtctagtg tgcaggattt gtaaggatcc actccaaatc    960
cgaggagctc g                                                        971

<210> SEQ ID NO 4
<211> LENGTH: 1278
<212> TYPE: DNA
<213> ORGANISM: Homo sapiens

<400> SEQUENCE: 4
ccagacaagt gattttgag gagtccctat ctataggaac aaagtaatta aaaaaatgta     60
tttcagaatt tacaggccca tgtgagatat gatttttta aatgaagatt tagagtaatg     120
ggtaaaaaag aggtatttgt gtgtttgttg attgttcagt cagtgaatgt acagcttctg    180
cctcatatcc aggcaccatc tcttcctgct ctttgttgtt aaatgttcca ttcctgggta    240
atttcatgtc tgccatcgtg gatatgccgt ggctccttga acctgcttgt gttgaagcag    300
gatcttcctt cctgtccctt cagtgcccta ataccatgta tttaaggctg gacacatcac    360
cactcccaac ctgcctcacc cactgcgtca cttgtgatca ctggcttctg gcgactctca    420
ccaaggtctc tgtcatgccc tgttataacg actacaaaag caagtcttac ctataggaaa    480
ataagaatta aaccctttt actggtcatg tgaaacttac catttgcaat tgtacagca     540 taaacacaga acagcacatc tttcaatgcc tgcatcctga aggcatttg tttgtgtctt    600 tcaatctggc tgtgctattg ttggtgttta acagtctccc cagctacact ggaaacttcc    660
agaaggcact tttcacttgc ttgtgtgttt tccccagtgt ctattagagg cctttgcaca    720
gggtaggctc tttggagcag ctgaaggtca cacatcccat gagcgggcag cagggtcaga    780
agtggccccc gtgttgccta agcaagactc tcccctgccc tctgccctct gcacctccgg    840
cctgcatgtc cctgtggcct cttggggta catctcccgg ggctgggtca gaaggcctgg    900
gtggttggcc tcaggctgtc acacacctag ggagatgctc ccgtttctgg gaaccttggc    960
cccgactcct gcaaacttcg gtaaatgtgt aactcgaccc tgcaccggct cactctgttc   1020
agcagtgaaa ctctgcatcg atcactaaga cttcctggaa gaggtcccag cgtgagtgtc    1080
gcttctggca tctgtccttc tggccagcct gtggtctggc caagtgatgt aaccctcctc   1140
tccagcctgt gcacaggcag cctgggaaca gctccatccc caccctcag ctataaatag    1200 ggcctcgtga cccggccagg ggaagaagct gccgttgttc tgggtactac agcagaaggt    1260
aagccggggg ccccctca                                                 1278
```

<210> SEQ ID NO 5
<211> LENGTH: 1426
<212> TYPE: DNA
<213> ORGANISM: Homo sapiens

<400> SEQUENCE: 5

```
caaggtcaca cagctggcaa ctggcagagc caggattcac gccctggcaa tttgactcca      60
gaatcctaac cttaacccag aagcacggct tcaagcccct ggaaaccaca atacctgtgg     120
cagccagggg gaggtgctgg aatctcattt cacatgtggg gaggggctc ccctgtgctc      180
aaggtcacaa ccaaagagga agctgtgatt aaaacccagg tcccatttgc aaagcctcga    240
cttttagcag gtgcatcata ctgttcccac ccctcccatc ccacttctgt ccagccgcct    300
agccccactt tctttttttt cttttttga acagtctcc ctcttgctga ggctggagtg      360
cagtggcgag atctcggctc actgtaacct ccgcctcccg ggttcaagcg attctcctgc    420
ctcagcctcc caagtagcta ggattacagg cgcccgccac cacgcctggc taacttttgt    480
attttagta gagatgggt ttcaccatgt tggccaggct ggtctcaaac tcctgacctt       540
aagtgattcg cccactgtgg cctcccaaag tgctgggatt acaggcgtga gctaccgccc    600
ccagcccctc ccatcccact tctgtccagc ccctagccc ctttctttt ctgggatcca      660
ggagtccaga tccccagccc cctctccaga ttacattcat ccaggcacag gaaaggacag   720
ggtcaggaaa ggaggactct gggcggcagc ctccacattc cccttccacg cttggccccc    780
agaatggagg agggtgtctg tattactggg cgaggtgtcc tcccttcctg gggactgtgg    840
ggggtggtca aaagacctct atgccccacc tccttcctcc ctctgccctg ctgtgcctgg    900
ggcaggggga gaacagccca cctcgtgact ggggggctggc ccagcccgcc ctatccctgg    960
gggaggggc gggacagggg gagccctata attggacaag tctgggatcc ttgagtccta    1020
ctcagcccca gcggaggtga aggacgtcct tccccaggag ccggtgagaa gcgcagtcgg    1080
gggcacgggg atgagctcag gggcctctag aaagagctgg gaccctggga agccctggcc    1140
tccaggtagt ctcaggagag ctactcgggg tcggcttgg ggagaggagg agcggggtg     1200
aggcaagcag caggggactg gacctgggaa gggctgggca gcagagacga cccgacccgc    1260
tagaaggtgg ggtggggaga gcagctgac tgggatgtaa gccatagcag gactccacga    1320
gttgtcacta tcatttatcg agcacctact gggtgtcccc agtgtcctca gatctccata    1380
actggggagc caggggcagc gacacggtag ctagccgtcg attgga               1426
```

<210> SEQ ID NO 6
<211> LENGTH: 1505
<212> TYPE: DNA
<213> ORGANISM: Homo sapiens

<400> SEQUENCE: 6

```
gctggtcgga ggctcgcagt gctgtcggcg agaagcagtc gggtttggag cgcttgggtc      60
gcgttggtgc gcggtggaac gcgcccaggg accccagttc ccgcgagcag ctccgcgccg    120
cgcctgagag actaagctga aactgctgct cagctcccaa gatggtgcca cccaaattgc    180
atgtgctttt ctgcctctgc ggctgcctgg ctgtggttta tccttttgac tggcaataca    240
taaatcctgt tgcccatatg aaatcatcag catgggtcaa caaaatacaa gtactgatgg    300
ctgctgcaag ctttggccaa actaaaatcc cccggggaaa tggccttat tccgttggtt      360
gtacagactt aatgtttgat cacactaata agggcacctt cttgcgttta tattatccat    420
```

-continued

```
cccaagataa tgatcgcctt gacacccttt ggatcccaaa taaagaatat ttttggggtc      480
ttagcaaatt tcttggaaca cactggctta tgggcaacat tttgaggtta ctctttggtt      540
caatgacaac tcctgcaaac tggaattccc ctctgaggcc tggtgaaaaa tatccacttg      600
ttgttttttc tcatggtctt ggggcattca ggacacttta ttctgctatt ggcattgacc      660
tggcatctca tgggtttata gttgctgctg tagaacacag agatagatct gcatctgcaa      720
cttactattt caaggaccaa tctgctgcag aaatagggga caagtcttgg ctctaccttagaa   780 gaaccctgaa acaagaggag agacacata tacgaaatga gcaggtacgg caaagagcaa       840
aagaatgttc ccaagctctc agtctgattc ttgacattga tcatgaaag ccagtgaaga       900 atgcattaga tttaaagttt gatatggaac aactgaagga ctctattgat agggaaaaaa     960
tagcagtaat tggacattct tttggtggag caacggttat tcagactctt agtgaagatc    1020
agagattcag atgtggtatt gccctggatg catggatgtt tccactgggt gatgaagtat    1080
attccagaat tcctcagccc ctcttttta tcaactctga atatttccaa tatcctgcta     1140
atatcataaa aatgaaaaaa tgctactcac ctgataaaga aagaaagatg attacaatca    1200
ggggttcagt ccaccagaat tttgctgact tcacttttgc aactggcaaa ataattggac    1260
acatgctcaa attaaaggga gacatagatt caaatgtagc tattgatctt agcaacaaag    1320
cttcattagc attcttacaa aagcatttag gacttcataa agattttgat cagtgggact    1380
gcttgattga aggagatgat gagaatctta ttccagggac caacattaac acaaccaatc    1440
aacacatcat gttacagaac tcttcaggaa tagagaaata caattaggat taaaataggt    1500
ttttt                                                                 1505

<210> SEQ ID NO 7
<211> LENGTH: 1419
<212> TYPE: DNA
<213> ORGANISM: Homo sapiens

<400> SEQUENCE: 7
gaattctgag ggcagagcgg gccactttct aggcctctga tttcatactg tggtgttagt       60
tacttctgag aggacagctt gctgccagag ctctatttt tatgttagag gctccttctg      120
cctgcagact ctgctgtctg ggaagggcac agcgttagga gggagaggga ggtgtgagtc     180
cctccgtgga cccgctgctt tgtacttctc tatctcattt cctttcagc accactctgg      240 gaaatcagta ttccagcccc attttatcct cagaaaattg aggctctgag atgttatctc     300
tgtgacctgg gtcctattac gtgccaaagg catcatttaa gcctaagatg tcctggctcc     360
aaggtgtcag catctggaag acaggcgcct catcctgcca tccctgctgc ggcttcactg     420
tggcccaggg gacatctcag cccgagaagg tcagcggccc cctcctggac caccgactcc     480
ccgcagaact cctctgtgcc ctctcctcac cagaccttgt tcctcccagt tgctcccaca    540
gccagggggc agtgagggct gctcttcccc cagccccact gaggaaccca ggaaggtgaa    600
cgagagaatc agtcctggtg ggggctgggg agggccccag acatgagacc agctcctccc   660
ccaggggatg ttatcagtgg gtccagaggg caaaataggg agcctggtgg agggaggggc   720
aaaggcctcg ggctctgagc ggccttggcc ttctccacca acccctccct acactcaggg   780
ggaggcggcg gtggggcaca cagggtgggg ggcgggtggc gggctgctgg gtgagcagca   840
ctcgcctgcc tggattgaaa cccagagatg gaggtgctgg gagggggctgt gagagctcag    900 ccctgtaacc aggccttgcc ggagccactg atgcccggtc ttctgtgcct ttactccaaa    960
catcccccag cccaagccac ccacttgttc tcaagtctga agaagaagtc cctcacccct   1020
```

```
ctactccagg ctgtgttcag ggcttggggc tggtggaggg aggggcctga aattccagtg    1080
tgaaaggctg agatgcccga gccctggcc tatgtccaag ccatttcccc tctctcacca    1140
gcctctccct ggggagccag tcagctagga aggaatgagg gctccccagg cccacccca    1200 gttcctgagc tcatctgggc tgcagggctg gcgggacagc agcgtggact cagtctccta    1260
gggatttccc aactctcccg cccgcttgct gcatctggac accctgcctc aggccctcat    1320
ctccactggt cagcaggtga cctttgccca gcgccctggg tcctcagtgc ctgctgccct    1380
ggagatgata taaacaggt cagaaccctc ctgcctgtc                            1419

<210> SEQ ID NO 8
<211> LENGTH: 3074
<212> TYPE: DNA
<213> ORGANISM: Homo sapiens

<400> SEQUENCE: 8
gaattccggg gagcaggaag agccaacatg ctggccccgc gcggagccgc cgtcctcctg      60
ctgcacctgg tcctgcagcg gtggctagcg gcaggcgccc aggccacccc ccaggtcttt     120
gaccttctcc catcttccag tcagaggcta aacccaggcg ctctgctgcc agtcctgaca     180
gaccccgccc tgaatgatct ctatgtgatt ccaccttca agctgcagac taaaagttca     240
gccaccatct tcggtcttta ctcttcaact gacaacagta aatattttga atttactgtg     300
atgggacgct taagcaaagc catcctccgt tacctgaaga cgatgggaa ggtgcatttg     360 gtggttttca acaacctgca gctggcagac ggaaggcggc acaggatcct cctgaggctg     420
agcaatttgc agcgagggc cggctcccta gagctctacc tggactgcat ccaggtggat     480
tccgttcaca atctccccag ggcctttgct ggccctccc agaaacctga gccattgaa     540 ttgaggactt tccagaggaa gccacaggac ttcttggaag agctgaagct ggtggtgaga     600
ggctcactgt tccaggtggc cagcctgcaa gactgcttcc tgcagcagag tgagccactg     660
gctgccacag gcacagggga ctttaaccgg cagttcttgg gtcaaatgac acaattaaac     720
caactcctgg gagaggtgaa ggaccttctg agacagcagg ttaaggaaac atcatttttg     780
cgaaacacca tagctgaatg ccaggcttgc ggtcctctca gtttcagtc tccgacccca     840 agcacggtgg tcgcccggc tcccctgca ccgccaacac gcccacctcg tcggtgtgac     900
tccaacccat gtttccgagg tgtccaatgt accgacagta gagatggctt ccagtgtggg     960
ccctgccccg agggctacac aggaaacggg atcacctgta ttgatgttga tgagtgcaaa    1020
taccatccct gctacccggg cgtgcactgc ataaatttgt ctcctggctt cagatgtgac    1080
gcctgcccag tgggcttcac agggcccatg gtgcagggtg ttgggatcag ttttgccaag    1140
tcaaacaagc aggtctgcac tgacattgat gagtgtcgaa atggagcgtg cgttcccaac    1200
tcgatctgcg ttaatacttt gggatcttac cgctgtgggc cttgtaagcc ggggtatact    1260
ggtgatcaga taaggggatg caaagtggaa agaaactgca gaaacccaga gctgaaccct    1320
tgcagtgtga atgcccagtg cattgaagag aggcagggg atgtgacatg tgtgtgtgga    1380
gtcggttggg ctggagatgg ctatatctgt ggaaaggatg tggacatcga cagttacccc    1440
gacgaagaac tgccatgctc tgccaggaac tgtaaaaagg acaactgcaa atatgtgcca    1500
aattctggcc aagaagatgc agacagagat ggcattggcg acgcttgtga cgaggatgct    1560
gacggagatg ggatcctgaa tgagcaggat aactgtgtcc tgattcataa tgtgaccaa    1620 aggaacagcg ataaagatat ctttgggat gcctgtgata actgcctgag tgtcttaaat    1680
```

```
aacgaccaga aagacaccga tggggatgga agaggagatg cctgtgatga tgacatggat    1740
ggagatggaa taaaaaacat tctggacaac tgcccaaaat ttcccaatcg tgaccaacgg    1800
gacaaggatg gtgatggtgt gggggatgcc tgtgacagtt gtcctgatgt cagcaaccct    1860
aaccagtctg atgtggataa tgatctggtt ggggactcct gtgacaccaa tcaggacagt    1920
gatggagatg ggcaccagga cagcacagac aactgcccca ccgtcattaa cagtgcccag    1980
ctggacaccg ataaggatgg aattggtgac gagtgtgatg atgatgatga caatgatggt    2040
atcccagacc tggtgccccc tggaccagac aactgccggc tggtccccaa cccagcccag    2100
gaggatagca cagcgacgg agtgggagac atctgtgagt ctgactttga ccaggaccag     2160
gtcatcgatc ggatcgacgt ctgcccagag aacgcagagg tcaccctgac cgacttcagg    2220
gcttaccaga ccgtgggcct ggatcctgaa ggggatgccc agatcgatcc caactgggtg    2280
gtcctgaacc agggcatgga gattgtacag accatgaaca gtgatcctgg cctggcagtg    2340
gggtacacag cttttaatgg agttgacttc gaagggacct tccatgtgaa tacccagaca    2400
gatgatgact atgcaggctt tatctttggc taccaagata gctccagctt ctacgtggtc    2460
atgtggaagc agacggagca gacatattgg caagccaccc cattccgagc agttgcagaa    2520
cctggcattc agctcaaggc tgtgaagtct aagacaggtc aggggagca tctccggaac     2580 tccctgtggc acgggggga caccagtgac caggtcaggc tgctgtggaa ggactccagg     2640
aatgtgggct ggaaggacaa ggtgtcctac cgctggttcc tacagcacag gccccaggtg    2700
ggctacatca gggtacgatt ttatgaaggc tctgagttgg tggctgactc tggcgtcacc    2760
atagacacca caatgcgtgg aggccgactt ggcgttttct gcttctctca agaaaacatc    2820
atctggtcca acctcaagta tcgctgcaat gacaccatcc tgaggacttt ccaagagttt    2880
caaacccaga atttcgaccg cttcgataat taaaccaagg aagcaatctg taactgcttt    2940
tcggaacact aaaaccatat atattttaac ttcaattttc tttagctttt accaaccccaa   3000 atatatcaaa acgttttatg tgaatgtggc aataaaggag aagagatcat ttttaaaaaa    3060
aaaaaaaaaa aaaa                                                      3074
```

<210> SEQ ID NO 9
<211> LENGTH: 1327
<212> TYPE: DNA
<213> ORGANISM: Homo sapiens

<400> SEQUENCE: 9

```
gatccccaga gactttccag atatctgaag aagtcctgat gtcactgccc cggtccttcc     60
ccaggtagag caacactcct cgtcgcaacc caactggctc cccttacctt ctacacacac    120
acacacacac acacacacac acacacaaat ccaagacaac actactaagg               180
cttctttggg agggggaagt agggataggt aagaggaaag taagggacct cctatccagc    240
ctccatggaa tcctgacttc ttttccttgt tatttcaact tcttccaccc catcttttaa    300
actttagact ccagccacag aagcttacaa ctaaagaaa ctctaaggcc aatttaatcc     360
aaggtttcat tctatgtgct ggagatggtg tacagtaggg tgaggaaacc aaattctcag    420
ttggcactgg tgtacccttg tacaggtgat gtaacatctc tgtgcctcag tttgctcact    480
ataaaataga gacggtaggg gtcatggtga gcactacctg actagcatat aagaagcttt    540
cagcaagtgc agactactct tacccacttc ccccaagcac agttggggtg ggggacagct    600
gaagaggtga aaacatgtgc ctgagaatcc taatgaaatc ggggtaaagg agcctggaac    660
acatcctgtg accccgcctg tcctgtagga agccagtctc tggaaagtaa aatggaaggg    720
```

```
ctgcttggga actttgagga tatttagccc accccctcat ttttacttgg ggaaactaag    780
gcccagagac ctaaggtgac tgcctaagtt agcaaggaga agtcttgggt attcatccca    840
ggttgggggg acccaattat ttctcaatcc cattgtattc tggaatgggc aatttgtcca    900
cgtcactgtg acctaggaac acgcgaatga gaacccacag ctgagggcct ctgcgcacag    960
aacagctgtt ctccccagga aatcaacttt ttttaattga gaagctaaaa aattattcta   1020
agagaggtag cccatcctaa aaatagctgt aatgcagaag ttcatgttca accaatcatt   1080
tttgcttacg atgcaaaaat tgaaaactaa gtttattaga gaggttagag aaggaggagc   1140
tctaagcaga aaaaatcctg tgccgggaaa ccttgattgt ggcttttttaa tgaatgaaga   1200 ggcctccctg agcttacaat ataaaagggg gacagagagg tgaaggtcta cacatcaggg   1260
gcttgctctt gcaaaaccaa accacaagac agacttgcaa aagaaggcat gcacagctca   1320
gcactgc                                                             1327

<210> SEQ ID NO 10
<211> LENGTH: 2376
<212> TYPE: DNA
<213> ORGANISM: Homo sapiens

<400> SEQUENCE: 10
tctagaaatg tctgcatgat ttttggattt tttgactttt aatttacctg tttgacattt     60
gctatgagcc tttcactcat aactaatata ttatttagtt ctctaagtaa ttttttggtta   120 cctactatat atcagatacc atgctaagta ctaggaatac agaatcaaat gaggcatggt   180
ccataccctc aagtagctta cattagaatg agagagacag ataaaccatt tcactacagt   240
tcagtgtgga aaatagagta gcagaggcag gtacaaggta ccattgaaca atgattaatg   300
actcttcctg ggacttggga acatcttccc agggaagtcg tcgaagctgt tttaaaatat   360
agcaaacttt tgtatttagt tcaggaacag catggcccat tttgccaatc acatcttaac   420
agttggaaaa gcaaacatat tatctatcag gctttcctct aaactttaaa tatgttttat   480
aagttataac tccagagaaa atttacaaag gataaacctt aatatagaag gaattagagc   540
tgccacagct tctacacttt taacctctca atatttatc tgttgggctc cactgtttct   600
tcctggaatt cacatcactg ccaccactct gttctccttg tcctcatatc aatgtggcca   660 aatatttttcc ctgtatttca atcaggacaa gacatggttt ttccccccca tcaaaggaat   720
ggagaaccat agaatactag ttttaaaatg tctttaggcc aggtgccgtg acccatgtct   780
gtaatcctag cactttgaga ggttgaggca ggagaatcac ttgatcccag agctcgaaac   840
cagcctgggc aacatagtga aacctctgtc tctattttt aaataaaatt tgaaaaagtc   900
tttagacata atctagtcta aaaatgaagg cttaaatgtg atgtatagcc ccctgccaag   960
tggctatcac ctgtgtgggc atcttcagtc atagggatct tattgccaca gagaaatccc  1020
tttaaactta ttgggtaaaa tctctccaat gtttattaag aaacacacaa aaaataaagc  1080
aaagaagaaa atgcaaaaga gttataaatg agaggaagca aaatgggcac ttattaaagg  1140
tctaataaat gcacatttgt atccatcatt ctactgagtt cttactccca agatgttctt  1200 cccctttagca aacaaataag caagtcagca agaaagaaa gaacaaacaa aatgtggtga  1260
tcagggaagc attgaggaga tggatggtgg caggtggcaa gaggactata aaagttttac  1320
aaaatgtctt cctctgaata tgtttagagt cttgcattca agcatttatt atacaccaat  1380
aatgtgagca acactttact tgacaaagaa acagaaaaga aaggaaagga agaaaacaga  1440
```

-continued

```
agagcatgaa gagaaaattt aggatggatt ctgttcttca acttcaaagc atctgctaat    1500
ttgaatttag ggaggagggg aaaaggttga aagagaataa gacatgtgta gaagacaagg    1560
acagagagaa tttcagtccg gtaagcaatg taattcattt caattctaca actatttatg    1620
gagcagctac gtgggcccat cacccattaa taaattggtt acagaattaa aaccaaccca    1680
aagggaatat acttccttct ttttcacaga ccctctttgt tctattctgc ccatgaggtt    1740
ttcctcctca agaaccagca aatccaacga cagtcaatag caggcattac aaatcagatt    1800
cagaaaaata aatcacccct tctaaatttc ttctagatat tatctttttat gttttgagta    1860 taattgtata tagtatagac tatagctatg tatgtacact ttccacttac atcttttatt    1920
tgcttttata atgtctttct taaaataaaa ctgcttttag aagttctgca caattctgat    1980
ttttaccaag tcaacctact tcttctctca aaaggacaaa cataaattgt ctagtgaatt    2040
ccagtcaatt tttccagaag aaaaaaaatg ctccagtttt ctcctctacc aagacaggaa    2100
gcacttcctg gagattaatc actgtgttgc cttgcaaaat tgggaaggtt gagagaaatt    2160
agtaaagtag gttgtatcat cctactttga atttggaatg tttggaaatg gtcctgctgc    2220
catttggatg aaagcaagga tgagtcaagc tgcgggtgat ccaaacaaac actgtcactc    2280
tttaaaagct gcgctcccga ggttggacct acaaggaggc aggcaagaca gcaaggcata    2340
gagacaacat agagctaagt aaagccagtg gaaatg                              2376
```

<210> SEQ ID NO 11
<211> LENGTH: 959
<212> TYPE: DNA
<213> ORGANISM: Homo sapiens

<400> SEQUENCE: 11

```
aagcttttac catggtaacc cctggtcccg ttcagccacc accaccccac ccagcacacc     60
tccaacctca gccagacaag gttgttgaca caagagagcc ctcaggggca cagagagagt    120
ctggacacgt gggggagtca gccgtgtatc atcggaggcg gccgggcaca tggcagggat    180
gagggaaaga ccaagagtcc tctgttgggc ccaagtccta gacagacaaa acctagacaa    240
tcacgtggct ggctgcatgc cctgtggctg ttgggctggg cccaggagga gggaggggcg    300
ctctttcctg gaggtggtcc agagcaccgg gtggacagcc ctgggggaaa acttccacgt    360
tttgatggag gttatctttg ataactccac agtgacctgg ttcgccaaag gaaaagcagg    420
caaacgtgag ctgtttttttt tttctccaag ctgaacacta ggggtcctag gcttttttggg    480 tcacccggca tggcagacag tcaacctggc aggacatccg ggagagacag acacaggcag    540
agggcagaaa ggtcaaggga ggttctcagg ccaaggctat tggggtttgc tcaattgttc    600
ctgaatgctc ttacacacgt acacacacag agcagcacac acacacacac acacatgcct    660
cagcaagtcc cagagaggga ggtgtcgagg gggacccgct ggctgttcag acggactccc    720
agagccagtg agtgggtggg gctggaacat gagttcatct atttcctgcc cacatctggt    780
ataaaaggag gcagtggccc acagaggagc acagctgtgt ttggctgcag ggccaagagc    840
gctgtcaaga agacccacac gccccctcc agcagctgaa ttcctgcagc tcagcagccg    900
ccgccagagc aggacgaacc gccaatcgca aggcacctct gagaacttca ggtaggaga    959
```

<210> SEQ ID NO 12
<211> LENGTH: 2480
<212> TYPE: DNA
<213> ORGANISM: Homo sapiens

<400> SEQUENCE: 12

-continued

```
gacgctctgt gccttcggag gtctttctgc ctgcctgtcc tcatgcctct cctcctcttg      60
ctgctcctgc tgccaagccc cttacacccc caccccatct gtgaggtctc caaagtggcc     120
agccacctag aagtgaactg tgacaagagg aatctgacag cgctgcctcc agacctgccg     180
aaagacacaa ccatcctcca cctgagtgag aacctcctgt acaccttctc cctggcaacc     240
ctgatgcctt acactcgcct cactcagctg aacctagata ggtgcgagct caccaagctc     300
caggtcgatg ggacgctgcc agtgctgggg accctggatc tatcccacaa tcagctgcaa     360
agcctgccct tgctagggca gacactgcct gctctcaccg tcctggacgt ctccttcaac     420
cggctgacct cgctgcctct tggtgccctg cgtggtcttg gcgaactcca agagctctac     480
ctgaaaggca atgagctgaa gaccctgccc cagggctcc tgacgccac acccaagctg      540
gagaagctca gtctggctaa caacaacttg actgagctcc ccgctgggct cctgaatggg     600
ctggagaatc tcgacaccct tctcctccaa gagaactcgc tgtatacaat accaaagggc     660
tttttttggt cccacctcct gccttttgct tttctccacg ggaacccctg gttatgcaac     720
tgtgagatcc tctatttttcg tcgctggctg caggacaatg ctgaaaatgt ctacgtatgg     780
aagcaaggtg tggacgtcaa ggccatgacc tctaacgtgg ccagtgtgca gtgtgacaat     840
tcagacaagt ttcccgtcta caaatacccca ggaaaggggt gccccaccct tggtgatgaa     900
ggtgacacag acctatatga ttactaccca gaagaggaca ctgagggcga taaggtgcgt     960
gccacaagga ctgtggtcaa gttccccacc aaagcccata caaccccctg gggtctattc    1020
tactcatggt ccactgcttc tctagacagc caaatgccct cctccttgca tccaacacaa    1080
gaatccacta aggagcagac cacattccca cctagatgga ccccaaattt cacacttcac    1140
atggaatcca tcacattctc caaaactcca aaatccacta ctgaaccaac ccaagcccg    1200
accacctcag agcccgtccc ggagcccgcc ccaaacatga ccaccctgga gcccactcca    1260
agcccgacca ccccagagcc cacctcagag cccgccccca gcccgaccac cccggagccc    1320
accccaatcc cgaccatcgc cacaagcccg accatcctgg tgtctgccac aagcctgatc    1380
actccaaaaa gcacattttt aactaccaca aaacccgtat cactcttaga atccaccaaa    1440
aaaaccatcc ctgaacttga tcagccacca aagctccgtg gggtgctcca agggcatttg    1500
gagagctcca gaaatgaccc ttttctccac cccgactttt gctgcctcct cccctgggc    1560
ttctatgtct tgggtctctt ctggctgctc tttgcctctg tggtcctcat cctgctgctg    1620
agctgggttg ggcatgtgaa accacaggcc ctggactctg gccaaggtgc tgctctgacc    1680
acagccacac aaaccacaca cctggagctg cagagggggac ggcaagtgac agtgccccgg    1740
gcctggctgc tcttccttcg aggttcgctt cccactttcc gctccagcct cttcctgtgg    1800
gtacggccta atggccgtgt ggggcctcta gtggcaggaa ggaggccctc agctctgagt    1860
cagggtcgtg gtcaggacct gctgagcaca gtgagcatta ggtactctgg ccacagcctc    1920
tgagggtggg aggtttgggg accttgagag aagagcctgt gggctctcct attggaatct    1980
agttgggggt tggagggta aggaacacag ggtgataggg gagggtctt agttcctttt    2040
tctgtatcag aagccctgtc ttcacaacac aggcacacaa tttcagtccc agccaaagca    2100
gaaggggtaa tgcatggac ttggcggggg gacaagacaa agctcccgat gctgcatggg    2160
gcgctgccag atctcacggt gaaccatttt ggcagaatac agcatggttc ccacatgcat    2220
ttatgcacag aagaaaatct ggaaagtgat ttatcaggat gtgagcactc gttgtgtctg    2280
gatgttacaa atatgggtgg ttttattttc tttttccctg tttagcattt tctagttttc    2340
```

```
ttatcaggat gtgagcactc gttgtgtctg gatgttacaa atatgggtgg ttttattttc    2400
tttttccctg tttagcattt tctagttttc cactattatt gtatattatc tgtataataa    2460
aaaataattt tagggttggg                                                2480

<210> SEQ ID NO 13
<211> LENGTH: 1337
<212> TYPE: DNA
<213> ORGANISM: Homo sapiens

<400> SEQUENCE: 13
cccccgacca tggcgaagct gattgcgctc accctcttgg ggatgggact ggcactcttc      60
aggaaccacc agtcttctta ccaaacacga cttaatgctc tccgagaggt acaacccgta     120
gaacttccta actgtaattt agttaaagga atcgaaactg gctctgaaga catggagata     180
ctgcctaatg gactggcttt cattagctct ggattaaagt atcctggaat aaagagcttc     240
aaccccaaca gtcctggaaa atacttctg atggacctga atgaagaaga tccaacagtg     300
ttggaattgg ggatcactgg aagtaaattt gatgtatctt catttaaccc tcatgggatt     360
agcacattca cagatgaaga taatgccatg tacctcctgg tggtgaacca tccagatgcc     420
aagtccacag tggagttgtt taaatttcaa gaagaagaaa atcgcttttt gcatctaaaa     480
accatcagac ataaacttct gcctaatttg aatgatattg ttgctgtggg acctgagcac     540
ttttatggca caaatgatca ctatttcttt gaccccttact tacaatcctg ggagatgtat     600
ttgggtttag cgtggtcgta tgttgtctac tatagtccaa gtgaagttcg agtggtggca     660
gaaggatttg attttgctaa tggaatcaac atttcacccg atggcaagta tgtctatata     720
gctgagttgc tggctcataa gattcatgtg tatgaaaagc atgctaattg gactttaact     780
ccattgaagt cccttgactt taatacctc gtggataaca tatctgtgga tcctgagaca     840
ggagaccttt gggttggatg ccatcccaat ggcatgaaaa tcttcttcta tgactcagag     900
aatcctcctg catcagaggt gcttcgaatc cagaacattc taacagaaga acctaaagtg     960
acacaggttt atgcagaaaa tggcacagtg ttgcaaggca gtacagttgc ctctgtgtac    1020
aaagggaaac tgctgattgg cacagtgttt cacaaagctc tttactgtga gctctaacag    1080
accgatttgc acccatgcca tagaaactga ggccattatt tcaaccgctt gccatattcc    1140
gaggacccag tgttcttagc tgaacaatga atgctgaccc taaatgtgga catcatgaag    1200
catcaaagca ctgtttaact gggagtgata tgatgtgtag ggcttttttt tgagaataca    1260
ctatcaaatc agtcttggaa tacttgaaaa cctcatttac cataaaaatc cttctcacta    1320
aaatggataa atcagtt                                                  1337

<210> SEQ ID NO 14
<211> LENGTH: 5515
<212> TYPE: DNA
<213> ORGANISM: Homo sapiens

<400> SEQUENCE: 14
ggaacttgat gctcagagag gacaagtcat tgcccaagg tcacacagct ggcaactggc       60
agacgagatt cacgccctgg caatttgact ccagaatcct aaccttaacc cagaagcacg     120
gcttcaagcc ctggaaacca caatacctgt ggcagccagg gggaggtgct ggaatctcat     180
ttcacatgtg gggaggggc tcctgtgctc aaggtcacaa ccaaagagga agctgtgatt     240
aaaacccagg tcccatttgc aaagcctcga cttttagcag gtgcatcata ctgttcccac     300
ccctcccatc ccacttctgt ccagccgcct agccccactt tcttttttttt cttttttga     360
```

```
gacagtctcc ctcttgctga ggctggagtg cagtggcgag atctcggctc actgtaacct    420
ccgcctcccg ggttcaagcg attctcctgc ctcagcctcc caagtagcta ggattacagg    480
cgcccgccac cacgcctggc taacttttgt attttagta gagatggggt ttcaccatgt    540
tggccaggct ggtctcaaac tcctgacctt aagtgattcg cccactgtgg cctcccaaag    600
tgctgggatt acaggcgtga gctaccgccc cagcccctc ccatcccact tctgtccagc    660
cccctagccc tactttcttt ctgggatcca ggagtccaga tccccagccc cctctccaga    720
ttacattcat ccaggcacag gaaaggacag ggtcaggaaa ggaggactct gggcggcagc    780
ctccacattc cccttccacg cttggccccc agaatggagg agggtgtctg tattactggg    840
cgaggtgtcc tcccttcctg gggactgtgg ggggtggtca aaagacctct atgccccacc    900
tccttcctcc ctctgccctg ctgtgcctgg ggcaggggga gaacagccca cctcgtgact    960
gggctgccca gcccgcccta tccctggggg aggggcggg acaggggag ccctataatt   1020 ggacaagtct gggatccttg agtcctactc agccccagcg gaggtgaagg acgtccttcc   1080
ccaggagccg gtgagaagcg cagtcggggg cacgggatg agctcagggg cctctagaaa   1140
gagctgggac cctgggaagc cctggcctcc aggtagtctc aggagagcta ctcggggtcg   1200
ggcttgggga gaggaggagc gggggtgagg caagcagcag gggactggac ctgggaaggg   1260
ctgggcagca gagacgaccc gacccgctag aaggtggggt ggggagagca gctggactgg   1320
gatgtaagcc atagcaggac tccacgagtt gtcactatca ttatcgagca cctactgggt   1380
gtccccagtg tcctcagatc tccataactg gggagccagg ggcagcgaca cggtagctag   1440
ccgtcgattg gagaactta aaatgaggac tgaattagct cataaatgga acacggcgct   1500
taactgtgag gttggagctt agaatgtgaa gggagaatga ggaatgcgag actgggactg   1560
agatggaacc ggcggtgggg agggggtggg gggatggaat ttgaaccccg ggagaggaag   1620
atggaatttt ctatggaggc cgacctgggg atggggagat aagagaagac caggaggag   1680 ttaaataggg aatgggttgg gggcggcttg gtaaatgtgc tgggattagg ctgttgcaga   1740
taatgcaaca aggcttggaa ggctaacctg gggtgaggcc gggttggggg cgctgggggt   1800
gggaggagtc ctcactggcg gttgattgac agtttctcct tccccagact ggccaatcac   1860
aggcaggaag atgaaggttc tgtgggctgc gttgctggtc acattcctgg caggtatggg   1920
ggcggggctt gctcggttcc ccccgctcct cccctctca tcctcacctc aacctcctgg   1980
ccccattcag acagaccctg ggcccctct tctgaggctt ctgtgctgct tcctggctct   2040
gaacagcgat ttgacgctct ctgggcctcg gtttccccca tccttgagat aggagttaga   2100
agttgttttg ttgttgttgt ttgttgttgt tgttttgttt ttttgagatg aagtctcgct   2160
ctgtcgccca ggctggagtg cagtggcggg atctcggctc actgcaagct ccgcctccca   2220
ggtccacgcc attctcctgc ctcagcctcc caagtagctg ggactacagg cacatgccac   2280
cacacccgac taactttttt gtattttcag tagagacggg gtttcaccat gttggccagg   2340
ctggtctgga actcctgacc tcaggtgatc tgcccgtttc gatctcccaa agtgctggga   2400
ttacaggcgt gagccaccgc acctggctgg gagttagagg tttctaatgc attgcaggca   2460
gatagtgaat accagacacg gggcagctgt gatctttatt ctccatcacc cccacacagc   2520
cctgcctggg gcacacaagg acactcaata catgcttttc cgctgggccg gtggctcacc   2580
cctgtaatcc cagcactttg ggaggccaag gtgggaggat cacttgagcc caggagttca   2640
acaccagcct gggcaacata gtgagaccct gtctctacta aaaatacaaa aattagccag   2700
```

```
gcatggtgcc acacacctgt gctctcagct actcaggagg ctgaggcagg aggatcgctt    2760
gagcccagaa ggtcaaggtt gcagtgaacc atgttcaggc cgctgcactc cagcctgggt    2820
gacagagcaa gaccctgttt ataaatacat aatgctttcc aagtgattaa accgactccc    2880
ccctcaccct gcccaccatg gctccaaaga agcatttgtg gagcaccttc tgtgtgcccc    2940
taggtagcta gatgcctgga cggggtcaga aggaccctga cccgaccttg aacttgttcc    3000
acacaggatg ccaggccaag gtggagcaag cggtggagag agagcggag cccgagctgc    3060
gccagcagac cgagtggcag agcggccagc gctgggaact ggcactgggt cgcttttggg    3120
attacctgcg ctgggtgcag acactgtctg agcaggtgca ggaggagctg ctcagctccc    3180
aggtcaccca ggaactgagg tgagtgtccc catcctggcc cttgaccctc ctggtgggcg    3240
gctatacctc cccaggtcca ggtttcattc tgccccgtc gctaagtctt gggggcctg     3300
ggtctctgct ggttctagct tcctcttccc atttctgact cctggcttta gctctctgga    3360
attctctctc tcagctttgt ctctctctct tcccttctga ctcagtctct cacactcgtc    3420
ctggctctgt ctctgtcctt ccctagctct tttatataga gacagagaga tggggtctca    3480
ctgtgttgcc caggctggtc ttgaacttct gggctcaagc gatcctcccg cctcggcctc    3540
ccaaagtgct gggattagag gcatgagcac cttgcccggc ctcctagctc cttcttcgtc    3600
tctgcctctg ccctctgcat ctgctctctg catctgtctc tgtctccttc tctcggcctc    3660
tgccccgttc cttctctccc tcttgggtct ctctggctca tccccatctc gcccgcccca    3720
tcccagccct tctcccccgc ctccccactg tgcgacaccc tcccgccctc tcggccgcag    3780
ggcgctgatg gacgagacca tgaaggagtt gaaggcctac aaatcggaac tggaggaaca    3840
actgaccccg gtggcggagg agacgcgggc acggctgtcc aaggagctgc aggcggcgca    3900
ggccccggctg gcgcggaca tggaggacgt gcgcggccgc ctggtgcagt accgcggcga    3960
ggtgcaggcc atgctcggcc agagcaccga ggagctgcgg gtgcgcctcg cctcccacct    4020
gcgcaagctg cgtaagcggc tcctccgcga tgccgatgac ctgcagaagc gcctggcagt    4080
gtaccaggcc ggggcccgcg agggcgccga gcgcggcctc agcgccatcc gcgagcgcct    4140
ggggcccctg gtggaacagg gccgcgtgcg ggccgccact gtgggctccc tggccggcca    4200
gccgctacag gagcgggccc aggcctgggg cgagcggctg cgcgcgcgga tggaggagat    4260
gggcagccgg acccgcgacc gcctggacga ggtgaaggag caggtggcgg aggtgcgcgc    4320
caagctggag gagcaggccc agcagatacg cctgcaggcc gaggccttcc aggcccgcct    4380
caagagctgg ttcgagcccc tggtggaaga catgcagcgc cagtgggccg ggctggtgga    4440
gaaggtgcag gctgccgtgg gcaccagcgc cgcccctgtg cccagcgaca atcactgaac    4500
gccgaagcct gcagccatgc gacccacgc caccccgtgc ctcctgcctc cgcgcagcct    4560
gcagcgggag accctgtccc cgccccagcc gtcctcctgg ggtggaccct agtttaataa    4620
agattcacca agtttcacgc atctgctggc ctcccctgt gatttcctct aagcccagc     4680
ctcagttct ctttctgccc acatactgcc acacaattct cagcccctc ctctccatct     4740
gtgtctgtgt gtatctttct ctctgccctt ttttttttt tagacggagt ctggctctgt    4800
cacccaggct agagtgcagt ggcacgatct ggctcactg caacctctgc ctcttgggtt    4860
caagcgattc tgctgcctca gtagctggga ttacaggctc acaccaccac acccggctaa    4920
ttttttgtatt tttagtagag acgagctttc accatgttgg ccaggcaggt ctcaaactcc    4980
tgaccaagtg atccacccgc cggcctccca aagtgctgag attacaggcc tgagccacca    5040
tgcccggcct ctgcccctct ttctttttta gggggcaggg aaaggtctca ccctgtcacc    5100
```

-continued

```
cgccatcaca gctcactgca gcctccacct cctggactca agtgataagt gatcctcccg    5160
cctcagcctt tccagtagct gagactacag gcgcatacca ctaggattaa tttgggggg     5220 ggtggtgtgt gtggagatgg ggtctggctt tgttggccag gctgatgtgg aattcctggg    5280
ctcaagcgat actcccacct tggcctcctg agtagctgag actactggct agcaccacca    5340
cacccagctt tttattatta tttgtagaga caaggtctca atatgttgcc caggctagtc    5400
tcaaacccct ggctcaagag atcctccgcc atcggcctcc caaagtgctg ggattccagg    5460
catgggctcc gagcggcctg cccaacttaa taatattgtt cctagagttg cactc          5515
```

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (17)..(17)
<223> OTHER INFORMATION: n stands for any base

<400> SEQUENCE: 15
ctcagaatgg ccaaaancc                                                  19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (18)..(18)
<223> OTHER INFORMATION: n stands for any base

<400> SEQUENCE: 16
cctcagaatg gccaaaantc                                                 20

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 17
gcagagctgc tgggacga                                                   18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (18)..(18)
<223> OTHER INFORMATION: n stands for any base

<400> SEQUENCE: 18
ggccctgtct tcgttaaggg                                                 20

<210> SEQ ID NO 19
<211> LENGTH: 22
<212> TYPE: DNA

```
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (20)..(20)
<223> OTHER INFORMATION: n stands for any base

<400> SEQUENCE: 19
atggccctgt cttcgttaan tg                                              22

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 20
ccagggctat ggaagtcgag tatc                                            24

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 21
accacggcgg tcatgngc                                                   18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 22
accacggcgg tcatgnac                                                   18

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 23
gcagcaaagg agtcccgagt                                                 20

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base
```

```
<400> SEQUENCE: 24
cggcagcttc ttcccncg                                              18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 25
cggcagcttc ttcccntg                                              18

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 26 ccaccccctca gctataaata gg                                        22

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (19)..(19)
<223> OTHER INFORMATION: n stands for any base

<400> SEQUENCE: 27
gaatggagga gggtgtctng a                                          21

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (20)..(20)
<223> OTHER INFORMATION: n stands for any base

<400> SEQUENCE: 28
agaatggagg agggtgtctn ta                                         22

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 29
ccaggaaggg aggacacctc                                            20

<210> SEQ ID NO 30
```

```
<211> LENGTH: 21
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (19)..(19)
<223> OTHER INFORMATION: n stands for any base

<400> SEQUENCE: 30
ttcttttggt ggagcaacng t                                              21

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (20)..(20)
<223> OTHER INFORMATION: n stands for any base

<400> SEQUENCE: 31
attcttttgg tggagcaacn tt                                             22

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 32
tcttacctga atctctgatc ttca                                           24

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 33
cggagccact gatgcncg                                                  18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 34
cggagccact gatgcntg                                                  18

<210> SEQ ID NO 35
<211> LENGTH: 22
<212> TYPE: DNA
<213> ORGANISM: Artificial Sequence
```

<220> FEATURE:
<223> OTHER INFORMATION: Description of Artificial Sequence:Primer

<400> SEQUENCE: 35
tgtttggagt aaaggcacag aa                                              22

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (17)..(17)
<223> OTHER INFORMATION: n stands for any base

<400> SEQUENCE: 36
cgagttggga acgcacnct                                                  19

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (17)..(17)
<223> OTHER INFORMATION: n stands for any base

<400> SEQUENCE: 37
cgagttggga acgcacngt                                                  19

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 38
ggtctgcact gacattgatg ag                                              22

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (22)..(22)
<223> OTHER INFORMATION: n stands for any base

<400> SEQUENCE: 39 taccccttgta caggtgatgt anta                                           24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (22)..(22)
<223> OTHER INFORMATION: n stands for any base

```
<400> SEQUENCE: 40 taccccttgta caggtgatgt anca                                              24

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 41
atagtgagca aactgaggca ca                                                 22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (20)..(20)
<223> OTHER INFORMATION: n stands for any base

<400> SEQUENCE: 42
cagagactgg cttcctacan ga                                                 22

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (21)..(21)
<223> OTHER INFORMATION: n stands for any base

<400> SEQUENCE: 43
ccagagactg gcttcctaca nta                                                23

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 44
gcctggaaca catcctgtga                                                    20

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (17)..(17)
<223> OTHER INFORMATION: n stands for any base

<400> SEQUENCE: 45
tttgatgggg ggaaaaanac                                                    19

<210> SEQ ID NO 46
<211> LENGTH: 18
```

```
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 46
ttgatggggg gaaaancc                                                      18

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 47
cctcatatca atgtggccaa                                                    20

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 48
ggcacagaga gagtctggac acg                                                23

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 49
ggccgcctcc gatgataca                                                     19

<210> SEQ ID NO 50
<211> LENGTH: 16
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (14)..(14)
<223> OTHER INFORMATION: n stands for any base

<400> SEQUENCE: 50
cccagggctc ctgncg                                                        16

<210> SEQ ID NO 51
<211> LENGTH: 17
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (15)..(15)
<223> OTHER INFORMATION: n stands for any base

<400> SEQUENCE: 51
```

```
ccccagggct cctgntg                                                          17
```

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence:Primer

<400> SEQUENCE: 52

```
tgagcttctc cagcttgggt g                                                     21
```

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (22)..(22)
<223> OTHER INFORMATION: n stands for any base

<400> SEQUENCE: 53

```
acccaaatac atctcccagg ancg                                                  24
```

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (22)..(22)
<223> OTHER INFORMATION: n stands for any base

<400> SEQUENCE: 54

```
aacccaaata catctcccag gnct                                                  24
```

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 55

```
gaatgatatt gttgctgtgg gac                                                   23
```

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (17)..(17)
<223> OTHER INFORMATION: n stands for any base

<400> SEQUENCE: 56

```
ccgatgacct gcagaancg                                                        19
```

<210> SEQ ID NO 57
<211> LENGTH: 20
<212> TYPE: DNA
<213> ORGANISM: Artificial Sequence

```
<220> FEATURE:
<223> OTHER INFORMATION: Description of Artificial Sequence:Primer
<220> FEATURE:
<221> NAME/KEY: misc_feature
<222> LOCATION: (18)..(18)
<223> OTHER INFORMATION: n stands for any base

<400> SEQUENCE: 57
gccgatgacc tgcagaantg                                              20

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 58
cggcctggta cactgccag                                               19

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence:Probe
<220> FEATURE:
<221> NAME/KEY: misc_feature
<222> LOCATION: (13)..(13)
<223> OTHER INFORMATION: n stands for any base

<400> SEQUENCE: 59
agccactgat gcncggtct                                               19

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence:Probe
<220> FEATURE:
<221> NAME/KEY: misc_feature
<222> LOCATION: (13)..(13)
<223> OTHER INFORMATION: n stands for any base

<400> SEQUENCE: 60
agccactgat gcntggtct                                               19

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence:Probe
<220> FEATURE:
<221> NAME/KEY: misc_feature
<222> LOCATION: (16)..(16)
<223> OTHER INFORMATION: n stands for any base

<400> SEQUENCE: 61
agtacaggtg atgtantatc tctgtg                                       26

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence:Probe
<220> FEATURE:
```

```
<221> NAME/KEY: misc_feature
<222> LOCATION: (15)..(15)
<223> OTHER INFORMATION: n stands for any base

<400> SEQUENCE: 62
gtacaggtga tgtancatct ctgtg                                              25

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:Probe

<400> SEQUENCE: 63
tggacacgtg ggggagtcag                                                    20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:Probe

<400> SEQUENCE: 64
tggacacgtg gggagtcagc                                                    20
```

METHODS OF DIAGNOSING RISK OF MYOCARDIAL INFARCTION BY DETECTION OF POLYMORPHISMS IN CONNEXIN AND NADH/NADPH OXIDASE GENES

TECHNICAL FIELD

The present invention relates to a detection method using genes associated with myocardial infarction. More particularly, it relates to a detection method using a plurality of gene polymorphisms associated with myocardial infarction and to a kit used for the method. The present invention can be used for, for example, diagnosing a risk of myocardial infarction.

BACKGROUND ART

Myocardial infarction is a multifactorial disease and its development is defined by the interaction between individual's genetic background and various environmental factors (Marenberg M E, Risch N, Berkman L F, Floderus B, de Faire U. Genetic susceptibility to death from coronary heart disease in a study of twins. N Engl J Med 1994;330:1041-1046., Nora J J, Lortscher R H, Spangler R D, Nora A H, Kimberling W J. Genetic-epidemiologic study of early-onset ischemic heart disease. Circulation 1980; 61: 503-508). In general, the risk of myocardial infarction is increased in proportion to the number of conventional risk factors such as hypertension, diabetes, hyperlipidemia, etc (Nora J J, Lortscher R H, Spangler R D, Nora A H, Kimberling W J. Genetic-epidemiologic study of early-onset ischemic heart disease. Circulation 1980; 61: 503-508). These risk factors themselves are partially regulated by genetic factors. However, since a family history is an independent predictable factor of myocardial infarction, it is suggested that there are genetic factors susceptible for myocardial infarction other than conventional risk factors (Marenberg M E, Risch N, Berkman L F, Floderus B, de Faire U. Genetic susceptibility to death from coronary heart disease in a study of twins. N Engl J Med 1994; 330: 1041-1046). In addition, cases in which myocardial infarction may be developed without any conventional risk factors also suggest the relationship between myocardial infarction and genetic factors.

Myocardial infarction is a disease with the highest mortality in the Western countries. Even in the case where myocardial infarction is not lethal, it may be complicated with heart failure, angina pectoris and refractory arrhythmia, thus deteriorating the quality of life of patients. Therefore, needless to say, it is important to prevent myocardial infarction. One of the methods for preventing myocardial infarction is to identify genes susceptible for myocardial infarction. By linkage analysis (Broeckel U, Hengstenberg C, Mayer B, et al. A comprehensive linkage analysis for myocardial infarction and its related risk factors. Nature genet 2002;30:210-214) and association studies by candidate genes (Cambien F, Poirier O, Lecerf L, et al. Deletion polymorphism in the gene for angiotensin-converting enzyme is a potent risk factor for myocardial infarction. Nature 1992; 359: 641-644. Weiss E J, Bray P F, Tayback M, et al. A polymorphism of a platelet glycoprotein receptor as an inherited risk factor for coronary thrombosis. N Engl J Med 1996; 334: 1090-1094., Iacoviello L, Di Castelnuovo A, De Knijff P, et al. Polymorphisms in the coagulation factor VII gene and the risk of myocardial infarction. N Engl J Med 1998;338:79-85., Kuivenhoven J A, Jukema J W, Zwinderman A H, et al. The role of a common variant of the cholesterol ester transfer protein gene in the progression of coronary atherosclerosis. N Engl J Med 1998; 338: 86-93), gene locus on the chromosome and some candidate genes which are associated with myocardial infarction have been identified. Previously, by studies of genetic epidemiology, there have been reported the relationships between the myocardial infarction and gene polymorphisms such as angiotensin converting enzyme (Cambien F, Poirier O, Lecerf L, et al. Deletion polymorphism in the gene for angiotensin-converting enzyme is a potent risk factor for myocardial infarction. Nature 1992; 359: 641-644), platlet glycoprotein IIIa (Weiss E J, Bray P F, Tayback M, et al. A genetical polymorphism of a platelet glycoprotein receptor as an inherited risk factor for coronary thrombosis. N Engl J Med 1996; 334: 1090-1094), blood coagulation factor VII, cholesterol ester tnrasfer protein (Kuivenhoven J A, Jukema J W, Zwinderman A H, et al. The role of a common variant of the cholesterol ester transfer protein gene in the progression of coronary atherosclerosis. N Engl J Med 1998; 338: 86-93), and the like. However, there have been conflicting reports, certain conclusion has never been reached. Furthermore, since different races have different gene polymorphisms, it is important to construct a database as to the relationship between polymorphisms and myocardial infarction in each race.

DISCLOSURE OF INVENTION

As mentioned above, a large number of relation analyses between gene polymorphisms and coronary artery disease or myocardial infarction have been carried out previously. However, many studies have not reached a certain finding in terms of significance thereof. This is mainly because populations of subjects in many studies are not sufficient and not only gene polymorphisms but also environmental factors are different between races. Furthermore, even if the relationship with myocardial infarction is recognized, in the analysis of large scale population, relative risk (odds ratio) is generally low.

The present invention was made on the basis of the above-mentioned background, and the object thereof is to provide a means of diagnosing genetic risk of myocardial infarction with high accuracy and high predictability and to contribute to a primary prevention of myocardial infarction.

To achieve the above-mentioned objects, the present inventors have extracted 71 genes which were estimated to be associated with coronary arteriosclerosis, coronary artery spasm, hypertension, diabetes, hyperlipidemia, etc., and mainly selected 112 polymorphisms which were predicted to be associated with functional changes of genes by the use of a plurality of public databases. Then, as to 112 polymorphisms of 71 genes, a large scale relation analysis of more than 5000 cases was carried out. As a result, the present inventors succeeded in identifying ten SNPs (single nucleotide polymorphisms) which were associated with myocardial infarction in males and five SNPs in females. In addition, by using the combination of these polymorphisms, it was found that in a stepwise forward selection of multivariate logistic regression analysis, a maximum odds ratio of 11.26 in males and maximum odds ratio of 88.51 in females were presented. Based on these results, it was possible to obtain a finding in that by selecting a plurality of SNPs from these SNPs and using the combination of the results of analysis of each SNP, diagnosis of myocardial infarction can be carried out with high reliability and high predictability. Meanwhile as to one of the five SNPs that were found to be associated with myocardial infarction in females, even by analyzing the polymorphism singly, extremely high odds ratio could be obtained. The present invention was completed based on the above findings and provides the following configuration.

[1] A method for detecting the genotype in a nucleic acid sample, comprising the following step (a):
  (a) analyzing two or more polymorphisms selected from the group consisting of the following (1) to (10) in a nucleic acid sample:
    (1) polymorphism at the base number position 1019 of the connexin 37 gene;
    (2) polymorphism at the base number position –863 of the tumor necrosis factor α gene;
    (3) polymorphism at the base number position 242 of the NADH/NADPH oxidase p22 phox gene;
    (4) polymorphism at the base number position –6 of the angiotensinogen gene:
    (5) polymorphism at the base number position –219 of the apolipoprotein E gene;
    (6) polymorphism at the base number position 994 of the platelet-activating factor acetylhydrolase gene;
    (7) polymorphism at the base number position –482 of the apolipoprotein C-III gene;
    (8) polymorphism at the base number position 1186 of the thrombospondin 4 gene;
    (9) polymorphism at the base number position –819 of the interleukin-10 gene; and
    (10) polymorphism at the base number position –592 of the interleukin-10 gene.

[2] A method for detecting the genotype in a nucleic acid sample, comprising the following step (b):
  (b) analyzing two or more polymorphisms selected from the group consisting of the following (11) to (15) in a nucleic acid sample:
    (11) polymorphism at the base number position –1171 of the stromelysin 1 gene;
    (12) polymorphism at the base number position –668 of the plasminogen activator inhibitor-1 gene;
    (13) polymorphism at the base number position 1018 of the glycoprotein Ibα gene;
    (14) polymorphism at the base number position 584 of the paraoxonase gene: and
    (15) polymorphism at the base number position 4070 of the apolipoprotein E gene.

[3] A method for detecting the genotype in a nucleic acid sample, comprising the following step (c):
  (c) analyzing polymorphism at the base number position 4070 of the apolipoprotein E gene in a nucleic acid sample.

[4] A method for diagnosing the risk of myocardial infarction, comprising the following steps (i) to (iii):
  (i) analyzing two or more polymorphisms selected from the group consisting of the following (1) to (10) in a nucleic acid sample:
    (1) polymorphism at the base number position 1019 of the connexin 37 gene;
    (2) polymorphism at the base number position –863 of the tumor necrosis factor α gene;
    (3) polymorphism at the base number position 242 of the NADH/NADPH oxidase p22 phox gene;
    (4) polymorphism at the base number position –6 of the angiotensinogen gene:
    (5) polymorphism at the base number position –219 of the apolipoprotein E gene;
    (6) polymorphism at the base number position 994 of the platelet-activating factor acetylhydrolase gene;
    (7) polymorphism at the base number position –482 of the apolipoprotein C-III gene;
    (8) polymorphism at the base number position 1186 of the thrombospondin 4 gene;
    (9) polymorphism at the base number position –819 of the interleukin-10 gene; and
    (10) polymorphism at the base number position –592 of the interleukin-10 gene;
  (ii) determining, based on the information about polymorphism which was obtained in the step (i), the genotype of the nucleic acid sample; and
  (iii) assessing, based on the genotype determined, a genetic risk of myocardial infarction.

[5] A method for diagnosing the risk of myocardial infarction, comprising the following steps (iv) to (vi):
  (iv) analyzing two or more polymorphisms selected from the group consisting of the following (11) to (15) in a nucleic acid sample:
    (11) polymorphism at the base number position –1171 of the stromelysin 1 gene;
    (12) polymorphism at the base number position –668 of the plasminogen activator inhibitor-1 gene;
    (13) polymorphism at the base number position 1018 of the glycoprotein Ibα gene;
    (14) polymorphism at the base number position 584 of the paraoxonase gene: and
    (15) polymorphism at the base number position 4070 of the apolipoprotein E gene;
  (v) determining, based on the information about polymorphism which was obtained in the step (i), the genotype of the nucleic acid sample; and
  (vi) assessing, based on the genotype determined, a genetic risk of myocardial infarction.

[6] A method for diagnosing the risk of myocardial infarction, comprising the following steps (vii) to (ix):
  (vii) analyzing polymorphism at the base number position 4070 of the apolipoprotein E gene in a nucleic acid sample;
  (viii) determining, based on the information about polymorphism which was obtained in the step (vii), the genotype of the nucleic acid sample; and
  (ix) assessing, based on the genotype determined, a genetic risk of myocardial infarction.

[7] A kit for detecting the genotype, comprising two or more of nucleic acids selected from the group consisting of the following (1) to (10):
  (1) a nucleic acid for polymorphism analysis at the base number position 1019 of the connexin 37 gene;
  (2) a nucleic acid for polymorphism analysis at the base number position –863 of the tumor necrosis factor α gene;
  (3) a nucleic acid for polymorphism analysis at the base number position 242 of the NADH/NADPH oxidase p22 phox gene;
  (4) a nucleic acid for polymorphism analysis at the base number position –6 of the angiotensinogen gene:
  (5) a nucleic acid for polymorphism analysis at the base number position –219 of the apolipoprotein E gene;
  (6) a nucleic acid for polymorphism analysis at the base number position 994 of the platelet-activating factor acetylhydrolase gene;
  (7) a nucleic acid for polymorphism analysis at the base number position –482 of the apolipoprotein C-III gene;
  (8) a nucleic acid for polymorphism analysis at the base number position 1186 of the thrombospondin 4 gene;
  (9) a nucleic acid for polymorphism analysis at the base number position –819 of the interleukin-10 gene; and
  (10) a nucleic acid for polymorphism analysis at the base number position –592 of the interleukin-10 gene.

[8] A kit for detecting the genotype, comprising two or more of nucleic acids selected from the group consisting of the following (11) to (15):
  (11) a nucleic acid for polymorphism analysis at the base number position −1171 of the stromelysin 1 gene;
  (12) a nucleic acid for polymorphism analysis at the base number position −668 of the plasminogen activator inhibitor-1 gene;
  (13) a nucleic acid for polymorphism analysis at the base number position 1018 of the glycoprotein Ibα gene;
  (14) a nucleic acid for polymorphism analysis at the base number position 584 of the paraoxonase gene: and
  (15) a nucleic acid for polymorphism analysis at the base number position 4070 of the apolipoprotein E gene.

[9] A kit for detecting the genotype, comprising a nucleic acid for polymorphism analysis at the base number position 4070 of the apolipoprotein E gene.

[10] Fixed nucleic acids comprising the following two or more nucleic acid selected from the group consisting of the following (1) to (10) fixed to an insoluble support:
  (1) a nucleic acid for polymorphism analysis at the base number position 1019 of the connexin 37 gene;
  (2) a nucleic acid for polymorphism analysis at the base number position −863 of the tumor necrosis factor α gene;
  (3) a nucleic acid for polymorphism analysis at the base number position 242 of the NADH/NADPH oxidase p22 phox gene;
  (4) a nucleic acid for polymorphism analysis at the base number position −6 of the angiotensinogen gene:
  (5) a nucleic acid for polymorphism analysis at the base number position −219 of the apolipoprotein E gene;
  (6) a nucleic acid for polymorphism analysis at the base number position 994 of the platelet-activating factor acetylhydrolase gene;
  (7) a nucleic acid for polymorphism analysis at the base number position −482 of the apolipoprotein C-III gene;
  (8) a nucleic acid for polymorphism analysis at the base number position 1186 of the thrombospondin 4 gene;
  (9) a nucleic acid for polymorphism analysis at the base number position −819 of the interleukin-10 gene; and
  (10) a nucleic acid for polymorphism analysis at the base number position −592 of the interleukin-10 gene.

[11] Fixed nucleic acids comprising the following two or more nucleic acid selected from the group consisting of the following (11) to (15) fixed to an insoluble support:
  (11) a nucleic acid for polymorphism analysis at the base number position −1171 of the stromelysin 1 gene;
  (12) a nucleic acid for polymorphism analysis at the base number position −668 of the plasminogen activator inhibitor-1 gene;
  (13) a nucleic acid for polymorphism analysis at the base number position 1018 of the glycoprotein Ibα gene;
  (14) a nucleic acid for polymorphism analysis at the base number position 584 of the paraoxonase gene: and
  (15) a nucleic acid for polymorphism analysis at the base number position 4070 of the apolipoprotein E gene.

[12] Fixed nucleic acids comprising a nucleic acid for polymorphism analysis at the base number position 4070 of the apolipoprotein E gene fixed to an insoluble support.

BRIEF DESCRIPTION OF DRAWINGS

FIG. 1 is a table summarizing 112 gene polymorphisms examined in a screening related analysis in Examples.

FIG. 2 is also a table summarizing 112 gene polymorphisms examined in a screening related analysis in Examples.

FIG. 3 is a table summarizing primers (SEQ ID NOs: 30, 31, 32, 21, 22, 23, 15, 16, 17, 24, 25, 26, 18, 19, 20, 33, 34, 35, 42, 43 and 44 in this order from the top), probes (SEQ ID NOs: 59 and 60 in this order from the top) and other conditions used in order to determine the genotype in Examples. In FIG. 3, FITC denotes fluorescein isothiocyanate and TxR denotes Texas Red, respectively.

FIG. 4 is also a table summarizing primers (SEQ ID NOs: 27, 28, 29, 39, 40, 41, 36, 37, 38, 53, 54, 55, 56, 57, 58, 48, 49, 45, 46, 47, 50, 51 and 52 in this order from the top), probes (SEQ ID NOs: 61, 62, 63 and 64 in this order from the top) and other conditions used in order to determine the genotype in Examples. In FIG. 4, FITC denotes fluorescein isothiocyanate and TxR denotes Texas Red, respectively.

FIG. 5 is a table summarizing the backgrounds of 909 gene polymorphisms examined in a screening related analysis in Examples. Data of age and body mass index are represented by average i standard deviation. In table, *1 denotes P=0.0278 and *2 denotes P<0.0001 versus controls, respectively.

FIG. 6 is a table summarizing gene polymorphisms which were found to be associated with myocardial infarction.

FIG. 7 is a table summarizing the backgrounds of all 5061 subjects in the relation analysis in Examples. Data of age and body mass index are represented by average ± standard deviation. In table, *1 denotes P=0.022, *2 denotes P<0.001 and *3 denotes P=0.017, respectively.

FIG. 8 is a table summarizing distribution of gene polymorphisms which were found to be associated with myocardial infarction in all 5061 subjects in the relation analysis in Examples.

FIG. 9 is a table showing results of multivariate logistic regression analysis of gene polymorphisms and myocardial infarction in all 5061 subjects in the relation analysis according to Examples. In table, OR denotes odds ratio and CI denotes confidence interval.

FIG. 10 is a table showing results of stepwise forward selection method of multivariate logistic regression analysis of gene polymorphisms associated with myocardial infarction. In this table, CI denotes confidence interval.

FIG. 11 is a table showing results of diagnosis of genetic risk (risk of development) of myocardial infarction using a combination of 5 gene polymorphisms in male.

FIG. 12 is a table showing results of diagnosis of genetic risk (risk of development) of myocardial infarction using a combination of 5 gene polymorphisms in female.

FIG. 13 is a graph showing the relationship between the number of gene polymorphisms combined and the odds ratio in contracting myocardial infarction. Note here that (A) shows the case of male subjects and (B) shows the case of female subjects.

BEST MODE FOR CARRYING OUT THE INVENTION

The first aspect of the present invention relates to a method for detecting the genotype in a nucleic acid sample. One embodiment of the present invention is featured by including the step of analyzing two or more polymorphisms selected from the group consisting of the following (1) to (10). Furthermore, another embodiment of the present invention is featured by including the step of analyzing two or more polymorphisms selected from the group consisting of the following (11) to (15). In addition, further embodiment of the present invention is featured by including at least the step of analyzing the following (15). Note here that it is possible to determine, based on the information about polymorphism which was obtained in the above-mentioned step, the genotype of the nucleic acid sample; and thereby to assess, based on the genotype determined, a genetic risk of myocardial infarction.

(1) polymorphism at the base number position 1019 of the connexin 37 gene: 1019C→T (hereinafter, also referred to as "connexin 37 (1019C→T) polymorphism")
(2) polymorphism at the base number position −863 of the tumor necrosis factor α gene: −863C→A (hereinafter, also referred to as "TNFα (−863C→A) polymorphism")
(3) polymorphism at the base number position 242 of the NADH/NADPH oxidase p22 phox gene: 242C→T (hereinafter, also referred to as "NADH/NADPH oxidase p22 phox (242C→T) polymorphism")
(4) polymorphism at the base number position −6 of the angiotensinogen gene: −6→GA (hereinafter, also referred to as "polymorphism angiotensinogen (−6G→A)")
(5) polymorphism at the base number position −219 of the apolipoprotein E gene: −219G→T (hereinafter, also referred to as "Apo E-219 (−219G→T) polymorphism")
(6) polymorphism at the base number position 994 of the platelet-activating factor acetylhydrolase gene: 994G→T (hereinafter, also referred to as "PAF acetylhydrolase (994G→T) polymorphism")
(7) polymorphism at the base number position −482 of the apolipoprotein C-III gene: −482C→T (hereinafter, also referred to as "Apo C-III (−482C→T) polymorphism")
(8) polymorphism at the base number position 1186 of the thrombospondin 4 gene: 1186G→(hereinafter, also referred to as "TSP4 (1186G→C) polymorphism")
(9) polymorphism at the base number position −819 of the interleukin-10 gene: −819T→C (hereinafter, also referred to as "IL-10 (−819T→C) polymorphism")
(10) polymorphism at the base number position −592 of the Interleukin-10 gene: −592A→C (hereinafter, also referred to as "IL-10 (−592A→C) polymorphism")
(11) polymorphism at the base number position −1171 of the stromelysin 1 gene: −1171/5A→6A (hereinafter, also referred to as "stromelysin 1 (−1171/5A→6A) polymorphism")
(12) polymorphism at the base number position −668 of the plasminogen activator inhibitor 1 gene: −668/4G→5G (hereinafter, also referred to as "PAI1 (−668/4G→5G) polymorphism")
(13) polymorphism at the base number position 1018 of the glycoprotein Ibα gene: 1018C→T (hereinafter, also referred to as "glycoprotein Ibα (1018C→T) polymorphism")
(14) polymorphism at the base number position 584 of the paraoxonase gene: 584G→A (hereinafter, also referred to as "paraoxonase (584G→A) polymorphism")
(15) polymorphism at the base number position 4070 of the apolipoprotein E gene: 4070C→T (hereinafter, also referred to as "Apo E (4070C→T) polymorphism")

In the above, description such as 1019C→T means that polymorphism at the relevant base number position consists of two genotypes, bases before and after the arrow. Herein, −1171/5A→6A means a polymorphism consisting of a genotype having five A (adenines) existing successively in the 3' direction from the base number position −1171 and a genotype having six A existing successively in the 3' direction from the base number position −1171. Similarly, −668/4G→5G means a polymorphism consisting of a genotype having four G (guanines) existing successively in the 3' direction from the base number −668 and a gene having five G existing successively in the 3' direction from the base number −668.

The base number of each gene is expressed using as standards the known sequences which are registered in the public database, GenBank (NCBI). Note here that in the base sequence of SEQ ID NO: 1 (Accession No. M96789: *Homo sapiens* connexin 37 (GJA4) mRNA, complete cds), the 1019th base corresponds to the base at position 1019 of the connexin 37 gene. Similarly, in the base sequence of SEQ ID NO: 2 (Accession No. L11698: *Homo sapiens* tumor necrosis factor alpha gene, promoter region), the 197th base corresponds to the base at position −863 of tumor necrosis factor α gene; in the base sequence of SEQ ID NO: 3 (Accession No. M61107: *Homo sapiens* cytochrome b light chain (CYBA) gene, exons 3 and 4), the 684th base corresponds to the base at position 242 of NADH/NADPH oxidase p22 phox gene; in the base sequence of SEQ ID NO: 4 (Accession No. X15323: *H. apiens* angiotensinogen gene 5' region and exon 1), the 463th base corresponds to the base at position −6 of angiotensinogen gene; in the base sequence of SEQ ID NO: 5 (Accession No. AF055343: *Homo sapiens* apolipoprotein E (APOE) gene, 5' regulatory region, partial sequence), the 801th base corresponds to the base at position −219 of the apolipoprotein E gene; in the sequence of SEQ ID NO: 6 (Accession No. U20157: Human platelet-activating factor acetylhydrolase mRNA, complete cds), the 996th base corresponds to the base at position 994 of the platelet-activating factor acetylhydrolase gene; in the sequence of SEQ ID NO: 7 (Accession No. X13367: Human DNA for apolipoprotein C-III 5'-flank), the 936th base corresponds to the base at position −482 of the apolipoprotein C-III gene; in the sequence of SEQ ID NO: 8 (Accession No. Z19585: *H. sapiens* mRNA for thrombospondin-4), the 1186th base corresponds to the base at position 1186 of the thrombospondin 4 gene; in the sequence of SEQ ID NO: 9 (Accession No. Z30175: *H. sapiens* IL-10 gene for interleukin-10 (promoter)), the 455th base corresponds to the base at position −819 and the 682th base corresponds to the base at position −592 of the interleukin-10 gene, respectively; in the sequence of SEQ ID NO: 10 (Accession No. U43511: *Homo sapiens stromelysin-1* gene, promoter region), the 698th base corresponds to the base at position −1171 of the stromelysin 1 gene; in the sequence of SEQ ID NO: 11 (Accession No. X13323: Human gene for plasminogen activator inhibitor 1 (PAI-1) 5'-flank and exon 1), the 131th base corresponds to the base at position −668 of the plasminogen activator inhibitor 1 gene; in the sequence of SEQ ID NO: 12 (Accession No. J02940: Human platelet glycoprotein Ib alpha chain mRNA, complete cds), the 524th base corresponds to the base at position 1018 of the glycoprotein Ibα gene; in the sequence of SEQ ID NO: 13 (Accession No. M63012: *H. sapiens* serum paraoxonase (PON) 1 mRNA, complete cds), the 584th base corresponds to the base at position 584 of the paraoxonase gene; and in the sequence of SEQ ID NO: 14 (Accession No. M10065: Human apolipoprotein E (epsilon-4 allele) gene, complete cds), the 4070th base corresponds to the base at position 4070 of the apolipoprotein E gene.

In the present invention, "analyzing polymorphism" refers to the investigation as to what genotype a nucleic acid sample has in the gene polymorphism to be analyzed. It is the same meaning as the investigation on the base (base sequence) of the position in which the polymorphism exists. Typically, for example, in the case of the analysis of the connexin 37 (1019C→T) polymorphism, it refers to investigation on what genotype, i.e., TT (homozygote of allele T) or CT (heterozygote of allele C and allele T) or CC (homozygote of allele C), the connexin 37 gene in a nucleic acid sample has.

As shown in Examples mentioned below, the polymorphisms mentioned (1) to (10) above are polymorphisms that are recognized as being particularly effective to be used in determining genetic risk of myocardial infarction in an analysis of Japanese male subjects. Therefore, analysis targeting these polymorphisms enables diagnosis with higher accuracy and with higher predictability when subjects are males, particularly, Japanese males.

Similarly, as shown in Examples mentioned below, the polymorphisms mentioned (11) to (15) above are polymorphisms that are recognized as being particularly effective to be used in determining genetic risk of myocardial infarction in an analysis of Japanese female subjects. Therefore, analysis targeting these polymorphisms enables diagnosis with higher accuracy and with higher predictability when subjects are females, particularly, Japanese females. Among these polymorphisms, as to the polymorphism described in (15), as shown in Examples mentioned below, it was confirmed that by analyzing the polymorphism, it was possible to determine the genetic risk of myocardial infarction with extremely high odds ratio. Therefore, by analyzing this polymorphism singly, it is possible to determine the genetic risk of myocardial infarction with high accuracy and high predictability. Of course, in addition to the analysis of the polymorphism (15), analysis of any one or a plurality of polymorphisms selected from (11) to (14) is carried out in combination, and thereby it may be possible to detect the genotype or to diagnose a genetic risk of myocardial infarction.

Herein, in principle, in proportion to the increase in the number of polymorphisms to be analyzed, the genotypes of nucleic acid sample are classified more finely. Thereby, it is possible to diagnose a genetic risk of myocardial infarction with higher predictability. From this viewpoint, it is preferable to detect the genotype by analyzing a larger number of polymorphisms in the above-mentioned polymorphisms (1) to (10). Therefore, it is the most preferable to analyze all of the polymorphisms (1) to (10). In the case where detection is carried out by combining nine or less of polymorphisms, it is possible to preferentially select the polymorphisms with higher odds ratios as in Examples mentioned below. For example, in the case where eight polymorphisms are used in combination, it is preferable to select nine polymorphisms with higher odds ratio, that is, to select (1), (3), (5), (6), (7), (8), (9) and (10). Similarly, in the case where seven polymorphisms are used in combination, it is preferable to select (1), (3), (5), (6), (8), (9) and (10). Similarly, in the case where 6 polymorphisms are used in combination, it is preferable to select (1), (5), (6), (8), (9) and (10). Similarly, in the case where five polymorphisms are used in combination, it is preferable to select (1), (5), (6), (8), and (9).

Similarly, in the case where two or more polymorphisms selected from the group consisting of polymorphisms (11) to (15), it is most preferable to analyze all these polymorphisms, that is, five polymorphisms. In the case where detection is carried out by combining four or less of polymorphisms, it is possible to preferentially select the polymorphisms with higher odds ratios in Examples mentioned below. For example, in the case where four polymorphisms are used in combination, it is preferable to select four polymorphisms with higher odds ratio, that is, to select (11), (12), (14) and (15). Similarly, in the case where three polymorphisms are used in combination, it is preferable to select (11), (12) and (15). Similarly, in the case where two polymorphisms are used in combination, it is preferable to select (11) and (15).

A method for analyzing each genetic polymorphism is not particularly limited. Known methods may include, for example, amplification by PCR using an allele-specific primer (and probe), a method for polymorphism analysis of amplified product by means of fluorescence or luminescence, PCR-RFLP (polymerase chain reaction-restriction fragment length polymorphism) method, PCR-SSCP (polymerase chain reaction-single strand conformation polymorphism) method (Orita, M. et al., Proc. Natl. Acad. Sci., U.S.A., 86, 2766-2770 (1989), etc.), PCR-SSO (specific sequence oligonucleotide) method, which use PCR method, ASO (allele specific oligonucleotide) hybridization method combining the PCR-SSO method and a dot hybridization method (Saiki, Nature, 324, 163-166 (1986), etc.), or TaqMan-PCR method (Livak, K J, Genet Anal, 14, 143 (1999), Morris, T. et al., J. Clin. Microbiol. ,34, 2933 (1996)), Invader method (Lyamichev V et al., Nat Biotechnol, 17, 292 (1999)), MALDI-TOF/MS (matrix) method using a primer extension method (Haff L A, Smirnov I P, Genome Res 7, 378 (1997)), RCA (rolling cycle amplification) method (Lizardi P M et al., Nat Genet 19,225 (1998)), a method using DNA microchip or microarray (Wang D G et al., Science 280, 1077 (1998), etc.)), a primer extension method, a Southern blot hybridization method, a dot hybridization method (Southern, E., J. Mol. Biol. 98, 503-517 (1975)), etc.), or the like. Furthermore, an analysis may be made by direct sequencing of the portion of polymorphism which is subject to analysis. Note here that polymorphisms may be analyzed by combining these methods ad libitum.

In the case where the amount of nucleic acid sample is small, it is preferable to analyze it by a method using PCR (for example, PCR-RFLP method) from the viewpoint of detection sensitivity or accuracy. Furthermore, any of the above-mentioned analysis methods may be employed after nucleic acid sample is amplified in advance (including a partial region of nucleic acid sample) by a gene amplification such as PCR method or a method applying PCR method.

Meanwhile, in the case where a large number of nucleic acid samples are analyzed, a method capable of analyzing a large number of samples in a relatively short period of time, particularly, for example, allele-specific PCR method, allele-specific hybridization method, TaqMan-PCR method, Invader method, MALDI-TOF/MS (matrix) method using primary extension method, RCA (rolling cycle amplification) method, or a method using a DNA chip or a micro-array.

The above methods use nucleic acids (also called "nucleic acids for polymorphism analysis" in the present invention), e.g., primer and probe in accordance with each method. Example of the nucleic acids for polymorphism analysis may include: a nucleic acid with a sequence complementary to a given region including the site of polymorphism (partial DNA region) in the gene which contains polymorphism that is subject to the analysis; and a nucleic acid (primer) which has a sequence complementary to a given region including the site of polymorphism(partial DNA region) and which is designed to allow the specific amplification of the DNA fragment containing the relevant site of polymorphism. In the case where polymorphism at position 1019 of the connexin 37 gene is a subject to be analyzed, an example of such nucleic acids includes a nucleic acid having a sequence complementary to a partial DNA region including the position 1019 of the connexin 37 gene in which the base at position 1019 is C (cytosine), or a nucleic acid having a sequence complementary to a partial DNA region including the position 1019 of the connexin 37 gene in which the base at position 1019 is T (thymine).

Other concrete examples of nucleic acids for polymorphism analysis may include a set of nucleic acids which is designed to specifically amplify the partial DNA region that contains the relevant site of polymorphism only in the case where the site of polymorphism that is a subject to the analysis is a certain genotype. A more concrete example may include for example, a set of nucleic acids which is designed to specifically amplify the partial DNA region including the site of polymorphism that is subject to the analysis and which consists of a sense primer that specifically hybridizes the partial DNA region including the relevant site of polymorphism in an antisense strand whose site of polymorphism is a certain genotype and of an antisense primer that specifically hybridizes a partial region of the sense strand. In the case where polymorphism at position 1019 of the connexin 37 gene is a subject to the analysis, examples of such a set of nucleic acids include a set of nucleic acids which is designed to specifically amplify the partial DNA region including the base at position 1019 of the connexin 37 gene and which consists of a sense primer that specifically hybridizes the partial DNA region containing the base at position 1019 in the antisense strand of the connexin 37 gene whose base at 1019 is C (cytosine) and of an antisense primer that specifically hybridizes a partial region of the sense strand; or a set of nucleic acids which consists of a sense primer that specifically hybridizes the partial DNA region including the base at position 1019 in the antisense strand of the connexin 37 gene whose base at position 1019 is T (thymine) and of an antisense primer that specifically hybridizes a partial region of the sense strand. The length of the partial DNA region to be amplified here is set accordingly in a range which is appropriate for its detection, and is for example, 50 bp to 200 bp, and preferably 80 bp to 150 bp. More concrete example of the set of nucleic acids for analyzing the connexin 37 (1019C→T) polymorphism for example may include a set containing the following sequences. Note here that an underlined part in the following sequences means a part corresponding to the polymorphism. Furthermore, in the sequence, N denotes any of A, T, C and G.

```
Sense primer
CTCAGAATGGCCAAAANCC:,          SEQ ID NO: 15
or

CCTCAGAATGGCCAAAANTC:          SEQ ID NO: 16

Antisense primer
GCAGAGCTGCTGGGACGA:            SEQ ID NO: 17
```

Similarly, an example of a nucleic acid primer for analyzing the TNFα (−863C→A) polymorphism may include a set of nucleic acids including the following sequences.

```
Antisense primer
GGCCCTGTCTTCGTTAANGG:,         SEQ ID NO: 18
or

ATGGCCCTGTCTTCGTTAANTG:        SEQ ID NO: 19

Sense primer
CCAGGGCTATGGAAGTCGAGTATC:      SEQ ID NO: 20
```

Similarly, an example of a nucleic acid primer for analyzing the NADH/NADPH oxidase p22 phox (242C→T) polymorphism may include a set of nucleic acids including the following sequences.

```
Antisense primer
ACCACGGCGGTCATGNGC:,           SEQ ID NO: 21
or

ACCACGGCGGTCATGNAC:            SEQ ID NO: 22

Sense primer
GCAGCAAAGGAGTCCCGAGT:          SEQ ID NO: 23
```

Similarly, an example of a nucleic acid primer for analyzing the angiotensinogen (−6G→A) polymorphism may include a set of nucleic acids including the following sequences.

```
Antisense primer
CGGCAGCTTCTTCCCNCG:.           SEQ ID NO: 24
or

CGGCAGCTTCTTCCCNTG:            SEQ ID NO: 25

Sense primer
CCACCCCTCAGCTATAAATAGG:        SEQ ID NO: 26
```

Similarly, an example of a nucleic acid primer for analyzing the Apo E (−219G→T) polymorphism may include a set of nucleic acids including the following sequences.

```
Sense primer
GAATGGAGGAGGGTGTCTNGA:,        SEQ ID NO: 27
or

AGAATGGAGGAGGGTGTCTNTA:        SEQ ID NO: 28

Antisense primer
CCAGGAAGGGAGGACACCTC:          SEQ ID NO: 29
```

Similarly, an example of a nucleic acid primer for analyzing the PAF acetylhydrolase (994G→T) polymorphism may include a set of nucleic acids including the following sequences.

```
Sense primer
TTCTTTTGGTGGAGCAACNGT:,        SEQ ID NO: 30
or

ATTCTTTTGGTGGAGCAACNTT:        SEQ ID NO: 31

Antisense primer
TCTTACCTGAATCTCTGATCTTCA:      SEQ ID NO: 32
```

Similarly, an example of a nucleic acid primer for analyzing the Apo C-III (−482C→T) polymorphism may include a set of nucleic acids including the following sequences.

```
Sense primer
CGGAGCCACTGATGCNCG:,           SEQ ID NO: 33
or

CGGAGCCACTGATGCNTG:            SEQ ID NO: 34

Antisense primer
TGTTTGGAGTAAAGGCACAGAA:        SEQ ID NO: 35
```

Similarly, an example of a nucleic acid primer for analyzing the TSP4 (1186G→C) polymorphism may include a set of nucleic acids including the following sequences.

```
Sense primer
CGAGTTGGGAACGCACNCT:,          SEQ ID NO: 36
or

CGAGTTGGGAACGCACNGT:           SEQ ID NO: 37

Antisense primer
GGTCTGCACTGACATTGATGAG:        SEQ ID NO: 38
```

Similarly, an example of a nucleic acid primer for analyzing the IL-10(−819T→C) polymorphism may include a set of nucleic acids including the following sequences.

```
Sense primer
TACCCTTGTACAGGTGATGTANTA:.        SEQ ID NO: 39
or

TACCCTTGTACAGGTGATGTANCA:         SEQ ID NO: 40

Antisense primer
ATAGTGAGCAAACTGAGGCACA:           SEQ ID NO: 41
```

Similarly, an example of a nucleic acid primer for analyzing the IL-10 (-592A→C) polymorphism may include a set including the following sequences.

```
Antisense primer
CAGAGACTGGCTTCCTACANGA:,          SEQ ID NO: 42
or

CCAGAGACTGGCTTCCTACANTA:          SEQ ID NO: 43

Sense primer
GCCTGGAACACATCCTGTGA:             SEQ ID NO: 44
```

Similarly, an example of a nucleic acid primer for analyzing the stromelysin 1 (-1171/5A→6A) polymorphism may include a set of nucleic acids including the following sequences.

```
Sense primer
TTTGATGGGGGGAAAAANAC:,            SEQ ID NO: 45
or

TTGATGGGGGGAAAANCC:               SEQ ID NO: 46

Antisense primer
CCTCATATCAATGTGGCCAA:             SEQ ID NO: 47
```

Similarly, an example of a nucleic acid primer for analyzing the PAI1 (-668/4G→5G) polymorphism may include a set of nucleic acids including the following sequences.

```
Sense primer
GGCACAGAGAGAGTCTGGACACG:          SEQ ID NO: 48

Antisense primer
GGCCGCCTCCGATGATACA:              SEQ ID NO: 49
```

Similarly, an example of a nucleic acid primer for analyzing the glycoprotein Ibα (1018C→T) polymorphism may include a set of nucleic acids including the following sequences.

```
Sense primer
CCCAGGGCTCCTGNCG:,                SEQ ID NO: 50
or

CCCCAGGGCTCCTGNTG:                SEQ ID NO: 51

Antisense primer
TGAGCTTCTCCAGCTTGGGTG:            SEQ ID NO: 52
```

Similarly, an example of a nucleic acid primer for analyzing the paraoxonase (584G→A) polymorphism may include a set of nucleic acids including the following sequences.

```
Sense primer
ACCCAAATACATCTCCCAGGANCG:,        SEQ ID NO: 53
or

AACCCAAATACATCTCCCAGGNCT:         SEQ ID NO: 54
```

```
Antisense primer
GAATGATATTGTTGCTGTGGGAC:          SEQ ID NO: 55
```

Similarly, an example of a nucleic acid primer for analyzing the Apo E (4070C→T) polymorphism may include a set of nucleic acids including the following sequences.

```
Sense primer
CCGATGACCTGCAGAANCG:,             SEQ ID NO: 56
or

GCCGATGACCTGCAGAANTG:             SEQ ID NO: 57

Antisense primer
CGGCCTGGTACACTGCCAG:              SEQ ID NO: 58
```

On the other hand, a concrete example of the probe can include:

as a probe for analyzing Apo C-III (-482C→T) polymorphism,

```
AGCCACTGATGCNCGGTCT:,             SEQ ID NO: 59
or

AGCCACTGATGCNTGGTCT:,             SEQ ID NO: 60
``` as a probe for analyzing IL-10 (-819T→C) polymorphism,

```
GTACAGGTGATGTANTATCTCTGTG:,       SEQ ID NO: 61
or,

GTACAGGTGATGTANCATCTCTGTG:,       SEQ ID NO: 62
and
``` as a probe for analyzing PAI1 (-668/4G→5G) polymorphism,

```
TGGACACGTGGGGGAGTCAG:,            SEQ ID NO: 63
or

TGGACACGTGGGGAGTCAGC:.            SEQ ID NO: 64
```

The above nucleic acid primers and nucleic acid probes are mere examples. Nucleic acid primers may contain a partially modified base sequence as long as they can carry out the aimed amplification reaction without inconvenience, while nucleic acid probes may contain a partially modified base sequence as long as they can carry out the aimed hybridization reaction without inconvenience. "Partially modified" herein means that part of bases is deleted, replaced, inserted, and/or added. The numbers of modified bases are for example one to seven, preferably one to five, and more preferably one to three. Note here that such a modification is made in the portions other than bases which correspond to the site of polymorphism, in principle. However, in the case where the polymorphism that is a subject of analysis is stromelysin 1 (-1171/5A→6A) polymorphism or PAI1 (-668/4G→5G) polymorphism, primers or probes obtained by modifying a part of base corresponding to a polymorphism site may be used.

As nucleic acids for polymorphism analysis (probes or primers), DNA fragments or RNA fragments are used accordingly in response to the analysis method employed. The base length of nucleic acids for polymorphism analysis may be sufficient if it exerts respective functions of each nucleic acid.

Base lengths in the case of use as primers are for example, 10 to 50 bp, preferably 15 to 40 bp, and more preferably 15 to 30 bp.

Note here that in the case of use as primers, some mismatches to the sequence which constitutes the template may be admitted as long as the primer can specifically hybridize the subject for amplification and amplify the target DNA fragment. In the case of probes, some mismatches to the sequence which is subject to detection may be similarly admitted as long as the probe can specifically hybridize the sequence which is subject to detection. The numbers of mismatches are one to several, preferably one to five, and more preferably one to three.

Nucleic acids for polymorphism analysis (primers and probes) can be synthesized in accordance with known methods, e.g., phosphodiester method. Note here that textbooks (e.g., Molecular Cloning, Third Edition, Cold Spring Harbor Laboratory Press, New York) can be referred with respect to the design, synthesis, and others of nucleic acids for polymorphism analysis.

Nucleic acids for polymorphism analysis in the present invention can be labeled with labeling substances in advance. The use of such labeled nucleic acids allows, for example, the analysis of polymorphism by using the labeling amount in the product of amplification as a marker. Furthermore, by labeling two kinds of primers which were designed specifically amplify the partial DNA region in the gene of each genotype that constitute polymorphism with labeling substances that are different from each other, the genotype of a nucleic acid sample can be discriminated according to the labeling substance and labeling amount to be detected based on the product of amplification. Concrete examples of detection methods using these labeled primers may include: a method for detecting polymorphism, comprising labeling, with fluorescein isocyanate and Texas red, two kinds of nucleic acid primers (allele-specific sense primers) that respectively and specifically hybridize the sense strand of each genotype constituting polymorphism; amplifying the partial DNA region including the site of polymorphism by using these labeled primers and the antisense primers that specifically hybridize the antisense strand; and measuring the labeling amount of each fluorescent substance in the product of amplification obtained. Note here that labeling of the antisense primer herein with for example, biotin allows the separation of the product of amplification by utilizing the specific binding between biotin and avidin.

Radioactive isotopes, for example, $^{32}P$, and fluorescent substance, for example, fluorescein isothiocyanate, tetramethyl rhodamine isothiocyanate, and Texas red, etc. can be exemplified as labeling substances to be used in labeling nucleic acids for polymorphism analysis. The 5' terminal labeling method using alkaline phosphatase and T4 polynucleotide kinase, the 3' terminal labeling method using T4 DNA polymerase and Klenow fragment, nicktranslation method, random primer method (Molecular Cloning, Third Edition, Chapter 9, Cold Spring Harbor Laboratory Press, New York), and the like can be exemplified as labeling methods.

The above-mentioned nucleic acids for polymorphism analysis can be used also under a condition fixed to an insoluble support. Processing of an insoluble support to be used for the fixation to several forms such as chips and beads allows the more simplified analysis of polymorphism by using these fixed nucleic acids.

A nucleic acid sample can be prepared from blood, skin cells, mucous cells, hair, and others from the subject according to known extraction methods and purification methods. In the case of including the gene which is subject to the analysis of polymorphism, the genome DNA of arbitrary length can be used as a nucleic acid sample. Furthermore, it is not necessary to use a nucleic acid sample in which all genes subject to the analysis are present on one nucleic acid. That is to say, as a nucleic acid sample of the present invention, both material in which all genes subject to the analysis are present on one nucleic acid and material in which genes subject to the analysis are present separately on two or more nucleic acids can be used. Note here that material in a fragmented or partial condition may be accepted as long as the site of polymorphism to be analyzed is at least present, although genes subject to the analysis in a nucleic acid sample are not in a complete condition (i.e., a condition in which the full length of the gene is present).

Analysis of each gene polymorphism is carried out each by each of the gene polymorphism or a plurality or entire gene polymorphisms are carried out simultaneously. In the former case, for example, nucleic acid sample collected from the subjects is divided in accordance with the number of polymorphisms to be analyzed, and analysis of polymorphism is carried out individually. In the latter case, for example, analysis of polymorphism can be carried out by DNA chip or micro-array. Note here that "simultaneousness" herein not only imply that all operations of the analysis process are conducted simultaneously but also include the case in which part of operations (e.g., operation to amplify nucleic acid, hybridization or detection of the probe) is conducted simultaneously.

Polymorphism of each gene can be analyzed by using mRNA which is a product of transcription of the gene which is subject to the analysis. After extracting and purifying mRNA of the gene which is subject to the analysis from blood, urine, and others of the subject, for example, polymorphism can be analyzed with mRNA as a starting material by conducting methods, e.g., Northern blotting method (Molecular Cloning, Third Edition, 7.42, Cold Spring Harbor Laboratory Press, New York), dot blotting method (Molecular Cloning, Third Edition, 7.46, Cold Spring Harbor Laboratory Press, New York), RT-PCR method (Molecular Cloning, Third Edition, 8.46, Cold Spring Harbor Laboratory Press, New York), and methods using the DNA chip (DNA array), and the like.

In addition, in the above-mentioned polymorphism, polymorphism involved with changes in amino acids can analyzed by using the expression product of gene that is a subject to analysis. In this case, material, even being partial protein or partial peptide, can be used as a sample for analysis as long as it contains amino acids which correspond to the site of polymorphism.

Analysis methods using these expression products of gene may include: a method for directly analyzing amino acids at the site of polymorphism, a method for immunologically analyzing utilizing changes of three-dimensional structure, or the like. As the former, a well-known amino acid sequence analysis method (a method using Edman method) can be used. As the latter, ELISA (enzyme-linked immunosorbent assay) using themonoclonal antibody or polyclonal antibody which has binding activity specific to the expression product of gene which has any of genotypes that constitute polymorphism; radioimmunoassay, immunoprecipitation method, immunodiffusion method, and the like can be used.

Information about polymorphism to be obtained by conducting the detection methods of the present invention described above can be used to diagnose a genetic risk of myocardial infarction. That is to say, the present invention also provides a method for diagnosing a genetic risk of myocardial infarction, which comprises a step for determining the genotype in a nucleic acid sample based on information about polymorphism that was obtained by the above-detection methods, and a step for assessing a genetic risk of myocardial infarction based on the determined genotype of the nucleic acid sample. Herein, the determination of the genotype is typically to determine which genotype both alleles of nucleic acid samples have with respect to the polymorphism to be detected. In the case where the subject to be detected is connexin 37 (1019C→T) polymorphism, for example, typically, investigation on what type the connexin 37 gene in a nucleic acid sample is TT (the base at position 1019 is a homozygote of allele T), CT (the base at position 1019 is a heterozygote of allele C and allele T) and CC (the base at position 1019 is a homozygote of allele C) in a nucleic acid sample the connexin 37 gene is.

By considering the results obtained in Example mentioned below, in order to enable a diagnosis of genetic risk of myocardial infarction with high accuracy and high predictability, for example, in the case of the connexin 37 (1019C→T) polymorphism, it is determined whether the genotype in a nucleic acid sample is TT or CT, or CC. Similarly, in the case of the TNFα (−863C→A) polymorphism, it is determined whether the genotype is AA or CA, or CC; in the case of NADH/NADPH oxidase p22 phox (242C→T) polymorphism, it is determined whether the genotype is TT or CT, or CC; in the case of angiotensinogen (−6G→A) polymorphism, it is determined whether the genotype is AA, or GA or GG; in the case of Apo E-219 (−219G→T) polymorphism, it is determined whether the genotype is TT, or GT or GG; in the case of PAF acetylhydrolase (994G→T) polymorphism, it is determined whether the genotype is TT, or GT, or GG; in the case of Apo C-III (−482C→T) polymorphism, it is determined whether the genotype is TT, or CT or CC; in the case of TSP4 (1186G→C) polymorphism, it is determined whether the genotype is CC or GC, or GG; in the case of IL-10 (−819T→C) polymorphism, it is determined whether the genotype is CC, or CT or TT; in the case of IL-10 (−592A→C) polymorphism, it is determined whether the genotype is CC, or CA or AA; in the case of stromelysin 1 (−1171/5A→6A) polymorphism, it is determined whether the genotype is 6A/6A or 5A/6A, or 5A/5A; in the case of PAI1 (−668/4G→5G) polymorphism, it is determined whether the genotype is 5G/5G or 4G/5G, or 4G/4G; in the case of glycoprotein Ibα (1018C→T) polymorphism, it is determined whether the genotype is TT, or CT or CC; in the case of paraoxonase (584G→A) polymorphism, it is determined whether the genotype is AA, or GA or GG; and in the case of Apo E (4070C→T) polymorphism, it is determined whether the genotype is TT, or CT or CC.

Diagnosis of a genetic risk of myocardial infarction enables prediction of potentiality in that myocardial infarction might be developed in the future (susceptibility to development), that is, risk of development (predisposition to development). Furthermore, based on the objective indicator that is the genotype, it is possible to recognize myocardial infarction and to evaluate the state of disease. In other words, according to the diagnosing method of the present invention, it is possible to asses the risk of development of myocardial infarction or to evaluate the state of disease. Above all, it is extremely significant from the clinical viewpoint to carry out the assessment of the risk of development. It is advantageous because awareness in advance of the risk of development contributes to primary prevention of myocardial infarction and makes it possible to take an appropriate measurement.

Information to be obtained by a diagnostic method of the present invention can be used for selecting an appropriate treatment, improvement of prognosis, improvement in QOL (quality of life of patients), or reduction in risk of development.

By carrying out the diagnostic method of the present invention regularly, it is possible to monitor, for example, the risk of development of myocardial infarction. As a result of such monitoring, if the correlation between some external factors (environmental factors, administration of drugs, etc.) and the increase in the risk of development is found, such external factors are recognized as risk factors and it is thought that the risk of development can be reduced based on this information.

By utilizing the genetic information associated with the development of myocardial infarction obtained by the present invention, it is possible to carry out a treatment (including a preventive treatment) for myocardial infarction. For example, as a result of carrying out the diagnostic method of the present invention, in the case where the polymorphism to be analyzed is a genotype to increase the risk of development of myocardial infarction, by introducing and expressing a gene having a genotype with low risk of development is introduced into a living body, the reduction of disease, suppression of development, and reduction of risk of development can be expected due to the expression of genes. The same treatment effect can be expected by a method including: introducing antisense strand with respect to mRNA of gene having a genotype with high risk of development and suppressing the expression of the mRNA.

The introduction of gene or antisense strand can be carried out by a method, for example, a method using a plasmid for gene introduction or a virus vector, electroporation (Potter, H. et al., Proc. Natl. Acad. Sci. U.S.A. 81, 7161-7165(1984), an ultrasonic microbubble (Lawrie, A., et al. Gene Therapy 7, 2023-2027 (2000)), lipofection (Felgner, P. L. et al., Proc. Natl. Acad. Sci. U.S.A. 84, 7413-7417 (1984)), microinjection (Graessmann, M. & Graessmann, A., Proc. Natl. Acad. Sci. U.S.A. 73,366-370(1976)), and the like. By utilizing these methods, desired genes, etc. can be directly introduced (in vivo method) or indirectly introduced (ex vivo method).

The second aspect of the present invention provides kits to be used in the above-mentioned detecting method or diagnostic method in the present invention (kits for detecting the genotype or kits for diagnosing myocardial infarction). Such kits contain nucleic acids (nucleic acid for polymorphism analysis) for analyzing two or more polymorphisms selected from the group consisting of polymorphisms described in (1) to (10) above; or such kits contain nucleic acids (nucleic acid for polymorphism analysis) for analyzing two or more polymorphisms selected from the group consisting of polymorphisms described in (11) to (15) above. As further embodiment, kits are constructed, which contains nucleic acid for polymorphism analysis described in (15) above.

In the analysis methods by which it is applied (a method which utilizes PCR using the above-mentioned allele-specific nucleic acids and the like, PCR-RFLP method, PCR-SSCP method, TaqMan-PCR method, Invader method, etc.), nucleic acids for polymorphism analysis are designed as materials which can specifically amplifies (primer) or specifically detect (probe) the DNA region containing the polymorphism portion to be analyzed or mRNA which corresponds to the region. Concrete examples of kits to be provided according to the present invention are described below.

A kit for detecting the genotype, comprising two or more nucleic acids selected from the group consisting of the below-mentioned (1) to (10):
(1) a nucleic acid having a sequence which is complementary to the partial DNA region containing the base at position 1019 of the connexin 37 gene whose base at position 1019 is C, or a nucleic-acid having a sequence which is complementary to the partial DNA region containing the base at position 1019 of the connexin 37 gene whose base at position 1019 is T:
(2) a nucleic acid having a sequence which is complementary to the partial DNA region containing the base at position −863 of the tumor necrosis factor α gene whose base at position −863 is C, or a nucleic acid having a sequence which is complementary to the partial DNA region containing the base at position −863 of the tumor necrosis factor α gene whose base at position −863 is A:
(3) a nucleic acid having a sequence which is complementary to the partial DNA region containing the base at position 242 of the NADH/NADPH oxidase p22 phox gene whose base at position 242 is C, or a nucleic acid having a sequence which is complementary to the partial DNA region containing the base at position 242 of the NADH/NADPH oxidase p22 phox gene whose base at position 242 is T:
(4) a nucleic acid having a sequence which is complementary to the partial DNA region containing the base at position −6 of the angiotensinogen gene whose base at position −6 is G, or a nucleic acid having a sequence which is complementary to the partial DNA region containing the base at position −6 of the angiotensinogen gene whose base at position −6 is A:
(5) a nucleic acid having a sequence which is complementary to the partial DNA region containing the base at position −219 of the apolipoprotein E gene whose base at position −219 is G, or a nucleic acid having a sequence which is complementary to the partial DNA region containing the base at position −219 of the apolipoprotein E gene whose base at position −219 is T:
(6) a nucleic acid having a sequence which is complementary to the partial DNA region containing the base at position 994 of the platelet-activating factor acetylhydrolase gene whose base at position 994 is G, or a nucleic acid having a sequence which is complementary to the partial DNA region containing the base at position 994 of the platelet-activating factor acetylhydrolase gene whose base at position 994 is T:
(7) a nucleic acid having a sequence which is complementary to the partial DNA region containing the base at position −482 of the apolipoprotein C-III gene whose base at position −482 is C, or a nucleic acid having a sequence which is complementary to the partial DNA region containing the base at position −482 of the apolipoprotein C-III gene whose base at position −482 is T:
(8) a nucleic acid having a sequence which is complementary to the partial DNA region containing the base at position 1186 of the thrombospondin 4 gene whose base at position 1186 is G, or a nucleic acid having a sequence which is complementary to the partial DNA region containing the base at position 1186 of the thrombospondin 4 gene whose base at position 1186 is C:
(9) a nucleic acid having a sequence which is complementary to the partial DNA region containing the base at position −819 of the interleukin-10 gene whose base at position −819 is T, or a nucleic acid having a sequence which is complementary to the partial DNA region containing the base at position −819 of the interleukin-10 gene whose base at position −819 is C: and
(10) a nucleic acid having a sequence which is complementary to the partial DNA region containing the base at position −592 of the interleukin-10 gene whose base at position −592 is A, or a nucleic acid having a sequence which is complementary to the partial DNA region containing the base at position −592 of the interleukin-10 gene whose base at position −592 is C.

In the above mention, kits are constructed by selecting two or more nucleic acids from the group consisting of (1) to (10). However, kits may be constructed by making a group consisting of two or more nucleic acids arbitrarily selected from (1) to (10) and selecting two or more nucleic acids from such a group. For example, kits are constructed by selecting two or more nucleic acids from the group consisting of (1), (5), (6), (8), (9) and (10) (nucleic acids for polymorphism analysis with odds ratio of one or more in Example mentioned below), or kits are constructed by selecting two or more nucleic acids from the group consisting of (1), (5), (6), (8) and (9) (nucleic acids for polymorphism analysis with five highest odds ratios in Example mentioned below).

A kit for detecting the genotype, comprising two or more nucleic acids selected from the group consisting of the following (11) to (15):
(11) a nucleic acid having a sequence which is complementarily to the partial DNA region containing the part of sequence of the stromelysin 1 gene in which five A successively exist in the 3' direction from the position −1171, or a nucleic acid having a sequence which is complementary to the partial DNA region containing the part of sequence of the stromelysin 1 gene in which six A successively exist in the 3' direction from the position −1171;
(12) a nucleic acid having a sequence which is complementary to the partial DNA region containing the part of sequence of the plasminogen activator inhibitor 1 gene in which four G successively exist in the 3' direction from the position −668, or a nucleic acid having a sequence which is complementary to the partial DNA region containing the part of sequence of the plasminogen activator inhibitor 1 gene in which five G successively exist in the 3' direction from the position −668 in the 3' direction;
(13) a nucleic acid having a sequence which is complementary to the partial DNA region containing the base at position 1018 of the glycoprotein Ibα gene whose base at position 1018 is C, or a nucleic acid having a sequence which is complementary to the partial DNA region containing the base at position 1018 of the glycoprotein Ibα gene whose base at position 1018 is T;
(14) a nucleic acid having a sequence which is complementary to the partial DNA region containing the base at position 584 of the paraoxonase gene whose base at position 584 is G, or a nucleic acid having a sequence which is complementary to the partial DNA region containing the base at position 584 of the paraoxonase gene whose base at position 584 is A; and
(15) a nucleic acid having a sequence which is complementary to the partial DNA region containing the base at position 4070 of the apolipoprotein E gene whose base at position 4070 is C, or a nucleic acid having a sequence which is complementary to the partial DNA region containing the base at position 4070 of the apolipoprotein E gene whose base at position 4070 is T.

In the above mention, kits are constructed by selecting two or more nucleic acids from the group consisting of (11) to (15). However, kits may be constructed by making a group consisting of two or more nucleic acids arbitrarily selected from (11) to (15) and selecting two or more nucleic acids from such a group. For example, kits are constructed by selecting two or more nucleic acids from the group consisting of (11), (12), (14) and (15) (nucleic acids for polymorphism analysis with odds ratio of one or more in Example mentioned below), or kits are constructed by selecting two or more nucleic acids from the group consisting of (11), (12) and (15) (nucleic-acids for polymorphism analysis with three highest odds ratios in Example mentioned below).

A kit for detecting the genotype comprising the following nucleic acid:

a nucleic acid having a sequence which is complementary to the partial DNA region containing the base at position 4070 of the apolipoprotein E gene whose base at position 4070 is C, or a nucleic acid having a sequence which is complementary to the partial DNA region containing the base at position 4070 of the apolipoprotein E gene whose base at position 4070 is T.

A kit for detecting the genotype, comprising two or more sets of nucleic acids selected from the group consisting of the following (1) to (10):

(1) a set of nucleic acids which is designed to specifically amplify the partial DNA region containing the base at position 1019 of the connexin 37 gene only in the case where the base at position 1019 of the connexin 37 gene in a nucleic acid sample is C, or a set of nucleic acids which is designed to specifically amplify the partial DNA region containing the base at position 1019 of the connexin 37 gene only in the case where the base at position 1019 of the connexin 37 gene in a nucleic acid sample is T;

(2) a set of nucleic acids which is designed to specifically amplify the partial DNA region containing the base at position −863 of the tumor necrosis factor α gene only in the case where the base at position −863 of the tumor necrosis factor α gene in a nucleic acid sample is C, or a set of nucleic acids which is designed to specifically amplify the partial DNA region containing the base at position −863 of the tumor necrosis factor α gene only in the case where the base at position −863 of the tumor necrosis factor α gene in a nucleic acid sample is A;

(3) a set of nucleic acids which is designed to specifically amplify the partial DNA region containing the base at position 242 of the NADH/NADPH oxidase p22 phox gene only in the case where the base at position 242 of the NADH/NADPH oxidase p22 phox gene in a nucleic acid sample is C, or a set of nucleic acids which is designed to specifically amplify the partial DNA region containing the base at position 242 of the NADH/NADPH oxidase p22 phox gene only in the case where the base at position 242 of the NADH/NADPH oxidase p22 phox gene in a nucleic acid sample is T;

(4) a set of nucleic acids which is designed to specifically amplify the partial DNA region containing the base at position −6 of the angiotensinogen gene only in the case where the base at position −6 of the angiotensinogen gene in a nucleic acid sample is G, or a set of nucleic acids which is designed to specifically amplify the partial DNA region containing the base at position −6 of the angiotensinogen gene only in the case where the base at position −6 of the angiotensinogen gene in a nucleic acid sample is A;

(5) a set of nucleic acids which is designed to specifically amplify the partial DNA region containing the base at position −219 of the apolipoprotein E gene only in the case where the base at position −219 of the apolipoprotein E gene in a nucleic acid sample is G, or a set of nucleic acids which is designed to specifically amplify the partial DNA region containing the base at position −219 of the apolipoprotein E gene only in the case where the base at position −219 of the apolipoprotein E gene in a nucleic acid sample is T;

(6) a set of nucleic acids which is designed to specifically amplify the partial DNA region containing the base at position 994 of the platelet-activating factor acetylhydrolase gene only in the case where the base at position 994 of the platelet-activating factor acetylhydrolase gene in a nucleic acid sample is G, or a set of nucleic acids which is designed to specifically amplify the partial DNA region containing the base at position 994 of the platelet-activating factor acetylhydrolase gene only in the case where the base at position 994 of the platelet-activating factor acetylhydrolase gene in a nucleic acid sample is T;

(7) a set of nucleic acids which is designed to specifically amplify the partial DNA region containing the base at position −482 of the apolipoprotein C-III gene only in the case where the base at position −482 of the apolipoprotein C-III gene in a nucleic acid sample is C, or a set of nucleic acids which is designed to specifically amplify the partial DNA region containing the base at position −482 of the apolipoprotein C-III gene only in the case where the base at position −482 of the apolipoprotein C-III gene in a nucleic acid sample is T;

(8) a set of nucleic acids which is designed to specifically amplify the partial DNA region containing the base at position 1186 of the thrombospondin 4 gene only in the case where the base at position 1186 of the thrombospondin 4 gene in a nucleic acid sample is G, or a set of nucleic acids which is designed to specifically amplify the partial DNA region containing the base at position 1186 of the thrombospondin 4 gene only in the case where the base at position 1186 of the thrombospondin 4 gene in a nucleic acid sample is C;

(9) a set of nucleic acids which is designed to specifically amplify the partial DNA region containing the base at position −819 of the interleukin-10 gene only in the case where the base at position −819 of the interleukin-10 gene in a nucleic acid sample is T, or a set of nucleic acids which is designed to specifically amplify the partial DNA region containing the base at position −819 of the interleukin-10 gene only in the case where the base at position −819 of the interleukin-10 gene in a nucleic acid sample is C; and

(10) a set of nucleic acids which is designed to specifically amplify the partial DNA region containing the base at position −592 of the interleukin-10 gene only in the case where the base at position −592of the interleukin-10 gene in a nucleic acid sample is A, or a set of nucleic acids which, is designed to specifically amplify the partial DNA region containing the base at position −592 of the interleukin-10 gene only in the case where the base at position −592 of the interleukin-10 gene in a nucleic acid sample is C;

In the above mention, kits are constructed by selecting two or more sets of nucleic acids from the group consisting of (1) to (10). However, kits may be constructed by making a group consisting of two or more sets of nucleic acids arbitrarily selected from (1) to (10) and selecting two or more sets of nucleic acids from such a group. For example, kits are constructed by selecting two or more sets of nucleic acids from the group consisting of (1), (5), (6), (8), (9) and (10) (nucleic acids for polymorphism analysis with odds ratio of one or more in Example mentioned below), or kits are constructed by selecting two or more sets of nucleic acids from the group consisting of (1), (5), (6), (8) and (9) (nucleic acids for polymorphism analysis with five highest odds ratios in Example mentioned below).

A kit for detecting the genotype, comprising two or more sets of nucleic acids selected from the group consisting of the following (11) to (15):

(11) a set of nucleic acids which is designed to specifically amplify the partial DNA region containing the part of sequence of the stromelysin 1 gene only in the case where five A exist successively in the 3' direction from the position −1171 in the stromelysin 1 gene in a nucleic acid sample, or a set of nucleic acids which is designed to specifically amplify the partial DNA region containing the part of sequence of the stromelysin 1 gene only in the case where six A exist successively in the 3' direction from the position −1171 in the stromelysin 1 gene in a nucleic acid sample;

(12) a set of nucleic acids which is designed to specifically amplify the partial DNA region containing the part of sequence of the plasminogen activator inhibitor 1 gene only in the case where four G exist successively in the 3' direction from the position −668 in the plasminogen activator inhibitor 1 gene in a nucleic acid sample, or a set of nucleic acids which is designed to specifically amplify the partial DNA region containing the part of sequence of the plasminogen activator inhibitor 1 gene only in the case where five G exist successively in the 3' direction from the position −668 in the plasminogen activator inhibitor 1 gene in a nucleic acid sample;

(13) a set of nucleic acids which is designed to specifically amplify the partial DNA region containing the base at position 1018 of the glycoprotein Ibα gene only in the case where the base at position 1018 of the glycoprotein Ibα gene in a nucleic acid sample is C, or a set of nucleic acids which is designed to specifically amplify the partial DNA region containing the base at position 1018 of glycoprotein Ibα gene only in the case where the base at position 1018 of the glycoprotein Ibα gene in a nucleic acid sample is T;

(14) a set of nucleic acids which is designed to specifically amplify the partial DNA region containing the base at position 584 of the paraoxonase gene only in the case where the base at position 584 of the paraoxonase gene in a nucleic acid sample is G, or a set of nucleic acids which is designed to specifically amplify the partial DNA region containing the base at position 584 of the paraoxonase gene only in the case where the base at position 584 of paraoxonase gene in a nucleic acid sample is A; and

(15) a set of nucleic acids which is designed to specifically amplify the partial DNA region containing the base at position 4070 of the apolipoprotein E gene only in the case where the base at position 4070 of the apolipoprotein E gene in a nucleic acid sample is C, or a set of nucleic acids which is designed to specifically amplify the partial DNA region containing the base at position 4070 of the apolipoprotein E gene only in the case where the base at position 4070 of the apolipoprotein E gene in a nucleic acid sample is T.

In the above mention, kits are constructed by selecting two or more sets of nucleic acids from the group consisting of (11) to (15). However, kits may be constructed by making a group consisting of two or more sets of nucleic acids arbitrarily selected from (11) to (15) and selecting two or more sets of nucleic acids from such a group. For example, kits may be constructed by selecting two or more sets of nucleic acids from the group consisting of (11), (12), (14) and (15) (sets of nucleic acids for polymorphism analysis with odds ratio of one or more in Example mentioned below), or kits may be constructed by selecting two or more sets of nucleic acids from the group consisting of (11), (12) and (15) (sets of nucleic acid for polymorphism analysis with three highest odds ratios in Example mentioned below).

A kit for detecting the genotype, comprising the following set of nucleic acids:

a set of nucleic acids which is designed to specifically amplify the partial DNA region containing the base at position 4070 of the apolipoprotein E gene only in the case where the base at position 4070 of the apolipoprotein E gene in a nucleic acid sample is C, or a set of nucleic acids which is designed to specifically amplify the partial DNA region containing the base at position 4070 of the apolipoprotein E gene only in the case where the base at position 4070 of the apolipoprotein E gene in a nucleic acid sample is T.

A kit for detecting the genotype, comprising two or more sets of nucleic acids selected from the group consisting of the following (1) to (10):

(1) a set of nucleic acids which is designed to specifically amplify the partial DNA region containing the base at position 1019 of the connexin 37 gene and which consists of a sense primer that specifically hybridizes the partial DNA region containing the base at position 1019 of the connexin 37 gene whose base at position 1019 is C and/or a sense primer that specifically hybridizes the partial DNA region containing the base at position 1019 in the connexin 37 gene whose gene at position 1019 is T and of an antisense primer that specifically hybridizes a partial portion of the connexin 37 gene;

(2) a set of nucleic acids which is designed to specifically amplify the partial DNA region containing the base at position −863 of the tumor necrosis factor α gene and which consists of an antisense primer that specifically hybridizes the partial DNA region containing the base at position −863 of the tumor necrosis factor α gene whose base at position −863 is C and/or an antisense primer that specifically hybridizes the partial DNA region containing the base at position −863 in the tumor necrosis factor α gene whose gene at position −863 is A and of a sense primer that specifically hybridizes a partial portion of the tumor necrosis factor α gene;

(3) a set of nucleic acids which is designed to specifically amplify the partial DNA region containing the base at position 242 of the NADH/NADPH oxidase p22 phox gene and which consists of an antisense primer that specifically hybridizes the partial DNA region containing the base at position −863 of the NADH/NADPH oxidase p22 phox gene whose base at position 242 is C and/or an antisense primer that specifically hybridizes the partial DNA region containing the base at position 242 in the NADH/NADPH oxidase p22 phox gene whose gene at position 242 is T and of a sense primer that specifically hybridizes a partial portion of the NADH/NADPH oxidase p22 phox gene;

(4) a set of nucleic acids which is designed to specifically amplify the partial DNA region containing the base at position −6 of the angiotensinogen gene and which consists of an antisense primer that specifically hybridizes the partial DNA region containing the base at position −6 of the angiotensinogen gene whose base at position −6 is G and/or an antisense primer that specifically hybridizes the partial DNA region containing the base at position −6 in the angiotensinogen gene whose gene at position −6 is A and of a sense primer that specifically hybridizes a partial portion of the angiotensinogen gene;

(5) a set of nucleic acids which is designed to specifically amplify the partial DNA region containing the base at position −219 of the apolipoprotein E gene and which consists of a sense primer that specifically hybridizes the partial DNA region containing the base at position –219 of the apolipoprotein E gene whose base at position –219 is G and/or a sense primer that specifically hybridizes the partial DNA region containing the base at position –219 in the apolipoprotein E gene whose gene at position –219 is T and of an antisense primer that specifically hybridizes a partial portion of the apolipoprotein E gene;

(6) a set of nucleic acids which is designed to specifically amplify the partial DNA region containing the base at position 994 of the platelet-activating factor acetylhydrolase gene and which consists of a sense primer that specifically hybridizes the partial DNA region containing the base at position 994 of the platelet-activating factor acetylhydrolase gene whose base at position 994 is G and/or a sense primer that specifically hybridizes the partial DNA region containing the base at position 994 in the platelet-activating factor acetylhydrolase gene whose gene at position 994 is T and of an antisense primer that specifically hybridizes a partial portion of the platelet-activating factor acetylhydrolase gene;

(7) a set of nucleic acids which is designed to specifically amplify the partial DNA region containing the base at position –482 of the apolipoprotein C-III gene and which consists of a sense primer that specifically hybridizes the partial DNA region containing the base at position –482 of the apolipoprotein C-III gene whose base at position –482 is C and/or a sense primer that specifically hybridizes the partial DNA region containing the base at position –482 in the apolipoprotein C-III gene whose gene at position –482 is T and of an antisense primer that specifically hybridizes a partial portion of the apolipoprotein C-III gene;

(8) a set of nucleic acids which is designed to specifically amplify the partial DNA region containing the base at position 1186 of the thrombospondin 4 gene and which consists of a sense primer that specifically hybridizes the partial DNA region containing the base at position 1186 of the thrombospondin 4 whose base at position 1186 is G and/or a sense primer that specifically hybridizes the partial DNA region containing the base at position 1186 in the thrombospondin 4 gene whose gene at position 1186 is C and of an antisense primer that specifically hybridizes a partial portion of the thrombospondin 4 gene;

(9) a set of nucleic acids which is designed to specifically amplify the partial DNA region containing the base at position –819 of the interleukin-10 gene and which consists of a sense primer that specifically hybridizes the partial DNA region containing the base at position –819 of the interleukin-10 whose base at position –819 is T and/or a sense primer that specifically hybridizes the partial DNA region containing the base at position –819 in the interleukin-10 gene whose gene at position –1186 is C and of an antisense primer that specifically hybridizes a partial portion of the interleukin-10 gene; and

(10) a set of nucleic acids which is designed to specifically amplify the partial DNA region containing the base at position –592 of the interleukin-10 gene and which consists of an antisense primer that specifically hybridizes the partial DNA region containing the base at position –592 of the interleukin-10 whose base at position –592 is A and/or an antisense primer that specifically hybridizes the partial DNA region containing the base at position –592 in the interleukin-10 gene whose gene at position –592 is C and of a sense primer that specifically hybridizes a partial portion of the interleukin-10 gene.

In the above mention, kits are constructed by selecting two or more sets of nucleic acids from the group consisting of (1) to (10). However, kits may be constructed by making a group consisting of two or more sets of nucleic acids arbitrarily selected from (1) to (10) and selecting two or more sets of nucleic acids from such a group. For example, kits are constructed by selecting two or more nucleic acids from the group consisting of (1), (5), (6), (8), (9) and (10) (sets of nucleic acids for polymorphism analysis with odds ratio of one or more in Example mentioned below), or kits are constructed by selecting two or more sets of nucleic acids from the group consisting of (1), (5), (6), (8) and (9) (sets of nucleic acids for polymorphism analysis with five highest odds ratios in Example mentioned below).

A kit for detecting the genotype, comprising two or more sets of nucleic acids selected from the group consisting of the following (11) to (15):

(11) a set of nucleic acids which is designed to specifically amplify the partial DNA region containing a part of polymorphism at position –1171 of the stromelysin 1 gene and which consists of a sense primer that specifically hybridizes the partial DNA region containing the corresponding sequence of the stromelysin 1 gene in which five A successively exist in the 3' direction from the position –1171, and/or a sense primer that specifically hybridizes the partial DNA region containing the corresponding sequence of the streomelysin 1 in which six A successively exist in the 3' direction from the position –1171, and an antisense primer that specifically hybridizes a part of region of the stromelysin 1 gene;

(12) a set of nucleic acids consisting of a pair of primers which are designed to specifically amplify the partial DNA region containing a part of polymorphism at position –668 of the plasminogen activator inhibitor 1 gene, as well as a probe that specifically hybridizes the partial DNA region containing the corresponding sequence in the plasminogen activator inhibitor 1 gene in which four G successively exist in the 3' direction from the position –668, and/or a probe that specifically hybridizes the partial DNA region containing the corresponding sequence in the plasminogen activator inhibitor 1 gene in which five G successively exist in the 3' direction from the position –668;

(13) a set of nucleic acids which is designed to specifically amplify the partial DNA region containing the base at position 1018 of the glycoprotein Ibα gene and which consists of a sense primer that specifically hybridizes the partial DNA region containing the base at position 1018 of the glycoprotein Ibα gene in which the base at position 1018 is C, and/or a sense primer that specifically hybridizes the partial DNA region of the glycoprotein Ibα gene in which the base at position 1018 is T, and an antisense primer that specifically hybridizes a part of region of the glycoprotein Ibα gene;

(14) a set of nucleic acids which is designed to specifically amplify the partial DNA region containing the base at position 584 of the paraoxonase gene and which consists of a sense primer that specifically hybridizes the partial DNA region containing the base at position 584 of the paraoxonase gene in which the base at position 584 is G, and/or a sense primer that specifically hybridizes the partial DNA region of the paraoxonase gene in which the base at position 584 is A, and an antisense primer that specifically hybridizes a part of region of the paraoxonase gene; and

(15) a set of nucleic acids which is designed to specifically amplify the partial DNA region containing the base at position 4070 of the apolipoprotein E gene and which consists of a sense primer that specifically hybridizes the partial DNA region containing the base at position 4070 of the apolipoprotein E gene in which the base at position 4070 is C, and/or a sense primer that specifically hybridizes the partial DNA region of the apolipoprotein E gene in which the base at position 4070 is T, and an antisense primer that specifically hybridizes a part of region of the apolipoprotein E gene;

In the above mention, kits are constructed by selecting two or more sets of nucleic acids from the group consisting of (11) to (15). However, kits may be constructed by making a group consisting of two or more sets of nucleic acids arbitrarily selected from (11) to (15) and selecting two or more sets of nucleic acids from such a group. For example, kits are constructed by selecting two or more nucleic acids from the group consisting of (11), (12), (14) and (15) (sets of nucleic acids for polymorphism analysis with odds ratio of one or more in Example mentioned below), or kits are constructed by selecting two or more sets of nucleic acids from the group consisting of (11), (12) and (15) (sets of nucleic acids for polymorphism analysis with three highest odds ratios in Example mentioned below).

A kit for detecting the genotype, comprising the following a set of nucleic acids, a set of nucleic acids which is designed to specifically amplify the partial DNA region containing the base at position 4070 of the apolipoprotein E gene and which consists of a sense primer that specifically hybridizes the partial DNA region containing the base at position 4070 of the apolipoprotein E gene in which the base at position 4070 is C, and/or a sense primer that specifically hybridizes the partial DNA region of the apolipoprotein E gene in which the base at position 4070 is T, and an antisense primer that specifically hybridizes a part of region of the apolipoprotein E gene.

A kit for detecting the genotype comprising two or more sets of nucleic acids selected from the group consisting of the following (1) to (10);

(1) a set of nucleic acids which consists of a first nucleic acid that specifically hybridizes a partial region containing the base at position 1019 in the antisense strand of the connexin 37 gene whose base at position 1019 is C and that is labeled with a first labeling substance, of a second nucleic acid that specifically hybridizes a partial region containing the base at position 1019 in the antisense strand of the connexin 37 gene whose base at position 1019 is T and that is labeled with a second labeling substance, and of a third nucleic acid that specifically hybridizes a partial region of the sense strand of the connexin 37 gene and that can specifically amplify the partial DNA region containing the base at position 1019 of the connexin 37 in concurrent use with the above first or second nucleic acid;

(2) a set of nucleic acids which consists of a first nucleic acid that specifically hybridizes a partial region containing the base at position −863 in the sense strand of the tumor necrosis factor α gene whose base at position −863 is C and that is labeled with a first labeling substance, of a second nucleic acid that specifically hybridizes a partial region containing the base at position −863 in the sense strand of the tumor necrosis factor α gene whose base at position −863 is A and that is labeled with a second labeling substance, and of a third nucleic acid that specifically hybridizes a partial region of the antisense strand of the tumor necrosis factor α gene and that can specifically amplify the partial DNA region containing the base at position −863 of the tumor necrosis factor α in concurrent use with the above first or second nucleic acid;

(3) a set of nucleic acids which consists of a first nucleic acid that specifically hybridizes a partial region containing the base at position 242 in the sense strand of the NADH/NADPH oxidase p22 phox gene whose base at position 242 is C and that is labeled with a first labeling substance, of a second nucleic acid that specifically hybridizes a partial region containing the base at position 242 in the sense strand of the NADH/NADPH oxidase p22 phox gene whose base at position 242 is T and that is labeled with a second labeling substance, and of a third nucleic acid that specifically hybridizes a partial region of the antisense strand of the NADH/NADPH oxidase p22 phox gene and that can specifically amplify the partial DNA region containing the base at position 242 of the NADH/NADPH oxidase p22 phox in concurrent use with the above first or second nucleic acid;

(4) a set of nucleic acids which consists of a first nucleic acid that specifically hybridizes a partial region containing the base at position −6 in the sense strand of the angiotensinogen gene whose base at position −6 is G and that is labeled with a first labeling substance, of a second nucleic acid that specifically hybridizes a partial region containing the base at position −6 in the sense strand of the angiotensinogen gene whose base at position −6 is A and that is labeled with a second labeling substance, and of a third nucleic acid that specifically hybridizes a partial region of the antisense strand of the angiotensinogen gene and that can specifically amplify the partial DNA region containing the base at position −6 of the angiotensinogen in concurrent use with the above first or second nucleic acid;

(5) a set of nucleic acids which consists of a first nucleic acid that specifically hybridizes a partial region containing the base at position −219 in the antisense strand of the apolipoprotein E gene whose base at position −219 is G and that is labeled with a first labeling substance, of a second nucleic acid that specifically hybridizes a partial region containing the base at position −219 in the antisense strand of the apolipoprotein E gene whose base at position −219 is T and that is labeled with a second labeling substance, and of a third nucleic acid that specifically hybridizes a partial region of the sense strand of the apolipoprotein E gene and that can specifically amplify the partial DNA region containing the base at position −219 of the apolipoprotein E in concurrent use with the above first or second nucleic acid;

(6) a set of nucleic acids which consists of a first nucleic acid that specifically hybridizes a partial region containing the base at position 994 in the antisense strand of the platelet-activating factor acetylhydrolase gene whose base at position 994 is G and that is labeled with a first labeling substance, of a second nucleic acid that specifically hybridizes a partial region containing the base at position 994 in the antisense strand of the platelet-activating factor acetylhydrolase gene whose base at position 994 is T and that is labeled with a second labeling substance, and of a third nucleic acid that specifically hybridizes a partial region of the sense strand of the platelet-activating factor acetylhydrolase gene and that can specifically amplify the partial DNA region containing the base at position 994 of the platelet-activating factor acetylhydrolase gene in concurrent use with the above first or second nucleic acid;

(7) a set of nucleic acids which consists of a first nucleic acid that specifically hybridizes a partial region containing the base at position −482 in the antisense strand of the apolipoprotein C-III gene whose base at position −482 is C, of a second nucleic acid that specifically hybridizes a partial region containing the base at position −482 in the antisense strand of the apolipoprotein C-III gene whose base at position −482 is T, of a third nucleic acid that specifically hybridizes a partial region of the sense strand of the apolipoprotein C-III gene and that can specifically amplify the partial DNA region containing the base at position −482 of the apolipoprotein C-III gene in concurrent use with the above first or second nucleic acid, of the fourth nucleic acid that specifically hybridizes the nucleic acid amplified by the use of the first and third nucleic acids; and of the fifth nucleic acid that specifically hybridizes the nucleic acid amplified by the use of the second and third nucleic acids;

(8) a set of nucleic acids which consists of a first nucleic acid that specifically hybridizes a partial region containing the base at position 1186 in the antisense strand of the thrombospondin 4 gene whose base at position 1186 is G and that is labeled with a first labeling substance, of a second nucleic acid that specifically hybridizes a partial region containing the base at position 1186 in the antisense strand of the thrombospondin 4 gene whose base at position 1186 is C and that is labeled with a second labeling substance, and of a third nucleic acid that specifically hybridizes a partial region of the sense strand of the thrombospondin 4 gene and that can specifically amplify the partial DNA region containing the base at position 1186 of the thrombospondin 4 gene in concurrent use with the above first or second nucleic acid;

(9) a set of nucleic acids which consists of a first nucleic acid that specifically hybridizes a partial region containing the base at position −819 in the antisense strand of the interleukin-10 gene whose base at position −819 is T, of a second nucleic acid that specifically hybridizes a partial region containing the base at position −819 in the antisense strand of the interleukin-10 gene whose base at position −819 is C, of a third nucleic acid that specifically hybridizes a partial region of the sense strand of the interleukin-10 gene and that can specifically amplify the partial DNA region containing the base at position −819 of the interleukin-10 gene in concurrent use with the above first or second nucleic acid, of the fourth nucleic acid that specifically hybridizes the nucleic acid amplified by the use of the first and third nucleic acids; and of the fifth nucleic acid that specifically hybridizes the nucleic acid amplified by the use of the second and third nucleic acids; and

(10) a set of nucleic acids which consists of a first nucleic acid that specifically hybridizes a partial region containing the base at position −592 in the sense strand of the interleukin-10 gene whose base at position −592 is A and that is labeled with a first labeling substance, of a second nucleic acid that specifically hybridizes a partial region containing the base at position −592 in the sense strand of the interleukin-10 gene whose base at position −592 is C and that is labeled with a second labeling substance, and of a third nucleic acid that specifically hybridizes a partial region of the antisense strand of the interleukin-10 gene and that can specifically amplify the partial DNA region containing the base at position −592 of the interleukin-10 gene in concurrent use with the above first or second nucleic acid.

In the above mention, kits are constructed by selecting two or more sets of nucleic acids from the group consisting of (1) to (10). However, kits may be constructed by making a group consisting of two or more sets of nucleic acids arbitrarily selected from (1) to (10) and selecting two or more sets of nucleic acids from such a group. For example, kits may be constructed by selecting two or more sets of nucleic acids from the group consisting of (1), (5), (6), (8), (9) and (10) (sets of nucleic acids for polymorphism analysis with odds ratio of one or more in Example mentioned below), or kits may be constructed by selecting two or more sets of nucleic acids from the group consisting of (1), (5), (6), (8) and (9) (sets of nucleic acids for polymorphism analysis with five highest odds ratios in Example mentioned below).

A kit for detecting the genotype, comprising two or more sets of nucleic acids selected from the group consisting of the following (11) to (15):

(11) a set of nucleic acids which consists of a first nucleic acid that specifically hybridizes a partial region containing a sequence which corresponds to the part of sequence in the antisense strand of the stromelysin 1 gene in which five A successively exist in the 3' direction from the position −1171 and that is labeled with a first labeling substance, of a second nucleic acid that specifically hybridizes a partial region containing a sequence which corresponds to the part of sequence in the antisense strand of the stromelysin 1 gene in which six A successively exist in the 3' direction from the position −1171 and that is labeled with a second labeling substance, and of a third nucleic acid that specifically hybridizes a partial region of the sense strand of the stromelysin 1 gene and that can specifically amplify the partial DNA region containing the base at position −1171 of the stromelysin 1 gene in concurrent use with the above first or second nucleic acid;

(12) a set of nucleic acids which consists of a pair of nucleic acids (a first nucleic acid and a second nucleic acid) that is designed to specifically amplify the partial DNA region containing a part of polymorphism at position -668 of the plasminogen activator inhibitor 1 gene, of a third nucleic acid that specifically hybridizes the nucleic acid which is obtained by amplification using plasminogen activator inhibitor 1 gene in which four G successively exist in the 3' direction from the position −668 as a template and the set of nucleic acids, and of a four nucleic acid that specifically hybridizes a nucleic acid which is obtained by amplification using plasminogen activator inhibitor 1 gene in which five G successively exist in the 3' direction from the position −668 as a template and the set of nucleic acids;

(13) a set of nucleic acids which consists of a first nucleic acid that specifically hybridizes a partial region containing a base which corresponds to the base at position 1018 in the antisense strand of the glycoprotein Ibα gene whose base at position 1018 is C and that is labeled with a first labeling substance, of a second nucleic acid that specifically hybridizes a partial region containing a base which corresponds to the base at position 1018 in the antisense strand of the glycoprotein Ibα gene whose base at position 1018 is T and that is labeled with a second labeling substance, and of a third nucleic acid that specifically hybridizes a partial region of the sense strand of the glycoprotein Ibα gene and that can specifically amplify the partial DNA region containing the base at position 1018 of the glycoprotein Ibα gene in concurrent use with the above first or second nucleic acid;

(14) a set of nucleic acids which consists of a first nucleic acid that specifically hybridizes a partial region containing a base which corresponds to the base at position 584 in the antisense strand of the paraoxonase gene whose base at position 584 is G and that is labeled with a first labeling substance, of a second nucleic acid that specifically hybridizes a partial region containing a base which corresponds to the base at position 584 in the antisense strand of the paraoxonase gene whose base at position 584 is A and that is labeled with a second labeling substance, and of a third nucleic acid that specifically hybridizes a partial region of the sense strand of the paraoxonase gene and that can specifically amplify the partial DNA region containing the base at position 584 of the paraoxonase gene in concurrent use with the above first or second nucleic acid; and

(15) a set of nucleic acids which consists of a first nucleic acid that specifically hybridizes a partial region containing a base which corresponds to the part of sequence in the antisense strand of the apolipoprotein E gene whose base at position 4070 is C and that is labeled with a first labeling substance, of a second nucleic acid that specifically hybridizes a partial region containing a base which corresponds to the part of sequence in the antisense strand of the apolipoprotein E gene whose base at position 4070 is T and that is labeled with a second labeling substance, and of a third nucleic acid that specifically hybridizes a partial region of the sense strand of the glycoprotein Ibα gene and that can specifically amplify the partial DNA region containing the base at position 4070 of the apolipoprotein E gene in concurrent use with the above first or second nucleic acid.

In the above mention, kits are constructed by selecting two or more sets of nucleic acids from the group consisting of (11) to (15). However, kits may be constructed by making a group consisting of two or more sets of nucleic acids arbitrarily selected from (11) to (15) and selecting two or more sets of nucleic acids from such a group. For example, kits are constructed by selecting two or more nucleic acids from the group consisting of (11), (12), (14) and (15) (sets of nucleic acids for polymorphism analysis with odds ratio of one or more in Example mentioned below), or kits are constructed by selecting two or more nucleic acids from the group consisting of (11), (12) and (15) (sets of nucleic acids for polymorphism analysis with three highest odds ratios in Example mentioned below).

A kit for detecting the genotype, comprising the following sets of nucleic acids:

a set of nucleic acids which consists of a first nucleic acid that specifically hybridizes a partial region containing a base which corresponds to the part of sequence in the antisense strand of the apolipoprotein E gene whose base at position 4070 is C and that is labeled with a first labeling substance, of a second nucleic acid that specifically hybridizes a partial region containing a base which corresponds to the part of sequence in the antisense strand of the apolipoprotein E gene whose base at position 4070 is T and that is labeled with a second labeling substance, and of a third nucleic acid that specifically hybridizes a partial region of the sense strand of the glycoprotein Ibα gene and that can specifically amplify the partial DNA region containing the base at position 4070 of the apolipoprotein E gene in concurrent use with the above first or second nucleic acid.

In the above-mentioned kits, one or two or more of reagents (buffer, reagent for reaction, and reagent for detection, etc.) may be combined in response to the usage of the kit.

The present invention is hereinafter explained in more detail by way of Examples.

EXAMPLE 1

Selection of Gene Polymorphism

By using several kinds of common databases including PubMed [National Center for Biological Information (NCBI)], Online Mendelian inheritance in Men (NCBI), Single Nucleotide Polymorphism (NCBI), etc., from a comprehensive viewpoint including vascular biology, platelet-leucocyte biology, congealing fibrinogenolysis system, a metabolic factor such as lipid, sugar, etc., 71 genes which were estimated to be associated with coronary arteriosclerosis, coronary artery spasm, hypertension, diabetes, hyperlipidemia, etc. were extracted from genes which had been previously reported. Furthermore, in the polymorphisms existing in these genes, 112 polymorphisms including polymorphisms which exist in promoter regions or exons, or polymorphisms which were located in splice donor sites or acceptor sites and which were expected to be associated with the functional changes of gene products were selected (FIGS. 1 and 2).

EXAMPLE 2

Determination of Gene Polymorphism

Subjects were 5061 Japanese males and females (3309 males and 1752 females) who visited as outpatients or were hospitalized in 15 participating institutes between July 1994 and December 2001. 2819 subjects (2003 males and 816 females) had myocardial infarction. All subjects were subjected to coronary angiography and left ventriculography. Diagnosis of myocardial infarction was carried out based on electrocardiographic change and increases in serum CK, GOT and LDH. Confirmed diagnosis of myocardial infarction was determined based on abnormality in wall motion in left ventriculography and stenosis of left main coronary artery or major coronary arteries corresponding thereto.

Controls were 2242 people (1306 males and 936 females) who visited the participating institutes and had at least one of the conventional risk factors of coronary artery diseases, i.e., smoking (10 cigarettes or more per day), obesity (body mass index $\geq 26$ kg/m$^2$), hypertension (systolic blood pressure $\geq 140$ mmHg or/and diastolic blood pressure $\geq 90$ mmHg), diabetes (fasting blood sugar $\geq 126$ mg/dL or/and hemoglobin A1c $\geq 6.5$%), hyperlipidemia (total cholesterol in serum $\geq 220$ mg/dL), hyperuricemia (male: uric acid $\geq 7.7$ mg/dL, female: uric acid $\geq 5.5$ mg/dL) but did not have coronary artery disease. In these controls, resting electrocardiogram showed normal, and also in exercise tolerance test, no change showing myocardial ischemia was observed.

From each of the subjects, 7 mL of venous blood was collected in a tube containing 50 mmol/L EDTA-2Na and genome DNA was extracted by using DNA extraction kit (Qiagen, Chatsworth, Calif.). 71 candidate genes 112 polymorphisms were determined by allele specific primer-probe measurement system (Toyobo Gene Analysis, Tsuruga, Japan) by fluorescence method and spectrometry (see FIGS. 3 and 4). DNA fragment-containing a polymorphism site was amplified by polymerase chain reaction (PCR) by using two kinds of allele specific sense primers (or antisense primers) whose 5' end were labeled with fluorescein isothiocyanate (FITC) or Texas red (TxR) and an antisense primer (or a sense primer) whose 5' end was labeled with biotin. Alternatively, DNA fragment containing polymorphism site was amplified by PCR by using two kinds of allele specific sense primer and antisense primer whose 5' end was labeled with biotin or by using a sense primer and antisense primer whose 5' end was labeled with biotin. The reaction solution (25 μL) contained 20 ng of DNA, 5 pmol of each primer, 0.2 mmol/L of each deoxynucleoside triphosphate (DATP, dGTP, dCTP and dTTP), 1-4 mmol/L of $MgCl_2$, 1 U DNA polymerase (rTaq or KODplus; Toyobo Co., Ltd. Osaka, Japan), and each DNA polymerase buffer was used. Amplification protocol included: initial degeneration at 95° C. for 5 minutes; 35-45 cycles of degeneration at 95° C. for 30 minutes, annealing at 55-67.5° C. for 30 seconds, and extension at 72° C. for 30 seconds; and final extension at 72° C. for 2 minutes.

In the determination of the genotype by fluorescent method, amplified DNA was incubated in a solution containing streptavidin binding magnetic beads in a 96-well plate at room temperature. This plate was disposed on a magnetic stand and supernatant was collected from each well and transferred into each well of the 96-well plate containing 0.01 M NaOH, followed by measuring fluorescence by microplate reader at excitation wavelength and emission wavelength of 485 nm and 538 nm for FITC and at excitation wavelength and emission wavelength of 584 nm and 612 nm for TxR. Furthermore, in the determination of the genotype by spectrometry, amplified DNA was denatured by 0.3 M NaOH and hybridized by using a hybridization buffer containing any of allele specific probe fixed to the bottom surface of each well of the 96-well plate and 35-40% formamide at 37° C. for 30 minutes. The well was thoroughly washed and then alkaline phosphatase binding streptavidin was added to each well and the plate was shaken at 37° for 15 minutes. The well was washed again and a solution containing 0.8 mM 2-(4-iodophenyl)-3-(4-nitrophenyl)-5-(2,4-disulfophenyl)-2H-tetrazolium (monosodium salt) and 0.4 mM 5-bromo-4-chloro-3-indolyl phosphate p-toluidine salt was added, followed by measuring the absorbance (450 nm).

In order to confirm the accuracy of the determination of the genotype, DNA samples of 50 people were selected at random, and the samples were subjected to PCR-restriction fragment length polymorphism (PCR-RFLP) method or direct sequence determination for nucleic acid of PCR product. In any samples, the genotype determined by the allele specific primer-probe measurement system were the same as those determined by PCR-polymerase chain reaction-restriction fragment length polymorphism method or direct determination method of DNA sequence.

Note here that statistical analysis in the following association study was carried out as follows. First of all, data were shown in average±standard deviation. Comparison of clinical data was carried out between patients with myocardial infarction and controls by using an unpaired Student's t test or a Mann-Whitney U test. Data in three groups were compared by way of a one-way analysis of variance and a Scheffe's post-hoc test or a Kruskal-Wallis test. Qualitative data were tested by a chi-square test. The allele frequency was estimated by a gene counting method and its deviation from the Hardy-Weinberg equilibrium was tested by a chi-square test. Furthermore, a multivariate logistic regression analysis in which risk factors were corrected was carried out. Myocardial infarction was used as a dependent variable, and age, body mass index (BMI), smoking condition (0=no smoking, 1=smoking), metabolic factor (0=without histories of hypertension, diabetes, hypercholesteremia, hyperuricemia, 1=with histories above) and genotype of respective polymorphisms were used as independent variables. The respective genotypes were analyzed for dominant, recessive, additive genetic models, and P value, odds ratio, 95% confidence interval (CI) were calculated. In the combination of analysis of the genotype, odds ratio of each the genotype was calculated by a stepwise forward selection method of logistic regression analysis.

EXAMPLE 3

Selection of Polymorphism Associated with Myocardial Infarction and Development of Method for Diagnosing Myocardial Infarction Firstly, screening related analyses regarding 71 genes 112 polymorphisms were carried out for 451 males (myocardial infarction: 219, control: 232) and 458 females (myocardial infarction: 226, control: 232). These cases were selected at random from entire 5061 cases.

Background data of 909 people (451 males and 458 females) subjected to screening related analyses by the above-mentioned method were shown in FIG. 5. In males, no significant difference was found in age, BMI, and frequency of conventional risk factors of coronary artery disease such as smoking, hypertension, diabetes, hypercholesterolemia, hyperuricemia, etc. between myocardial infraction group and control group. In females, no significant difference was found in age, BMI, and frequency of hypercholesterolemia, hyperuricemia, etc. was not found between myocardial infarction group and control group, but the prevalence of smoking or diabetes was significantly higher in myocardial infarction group as compared with the control group. In the screening-related analysis between 112 polymorphisms and myocardial infarction, by the multivariate logistic regression analysis in which age, BMI, and conventional risk factors for coronary artery disease such as smoking, hypertension, diabetes, hypercholesterolemia, hyperuricemia were corrected, 19 single nucleotide polymorphisms (SNP) in males and 18 single nucleotide polymorphisms (SNP) in females were shown to be associated with myocardial infarction (FIG. 6). Note here that in the screening-related analyses, category, in which P value <0.1 in logistic regression analysis shows to have relation, was employed. In these SNPs, four SNPs were related to myocardial infarction in both males and females and other SNPs were related to myocardial infarction in either one of males or females.

Then, the determination of the genotype of these polymorphisms was carried out in the rest 4152 cases (male myocardial infarction subjects: 1784, male control: 1074, female myocardial infarction subjects: 590 and female control: 704). A large scale association study of these polymorphisms and myocardial infarction was carried out in total 5061 cases (male myocardial infarction subjects: 2003, male control: 1306, female myocardial infarction subjects: 816 and female control: 936).

FIG. 7 shows background data of the total 5061 cases (3309 males and 1752 females) in the large scale association study. In males, no significant difference was found in age, BMI and frequency of smoking between the myocardial infarction group and the control group, but the prevalence of hypertension or hyperuricemia was significantly lower in myocardial infarction group as compared with the control group, and the prevalence of diabetes or hypercholesterolemia was significantly higher in myocardial infarction group as compared with the control group. In females, no significant difference in age or the prevalence of hypertension was found between the infarction group and the control group, but BMI and the prevalence of smoking, diabetes, hypercholesterolemia,or hyperuricemia was significantly higher in myocardial infarction group as compared with the control group. In a large scale association study of myocardial infarction in the males (19

SNP) and females (18 SNP), by the multivariable logistic regression analysis in which age, BMI, and frequency of smoking, hypertension, diabetes, hypercholesterolemia, hyperuricemia were corrected, 10 SNPs in males and 5 SNPs in females showed significant relation to the myocardial infarction ($P<0.05$ in either of dominant or recessive gene model) (FIG. 8). Distribution of the genotypes and results of logistic regression analysis are shown in FIGS. 8 and 9, respectively.

In this Example, a stepwise forward selection method of multivariate logistic regression analysis was carried out (see FIG. 10). This method employed dominant or recessive genetic model based on P value in relation to the myocardial infarction of the respective SNPs shown in FIG. 9. FIG. 10 shows gene locus on the chromosome of these genes. The $-819T \rightarrow C$ polymorphism and $-592A \rightarrow C$ polymorphism in the interleukin-10 were in linkage disequilibrium [pairwise linkage disequilibrium coefficient, D' (D/$D_{max}$), of 0.406; standardized linkage disequilibrium coefficient, .r, of 0.396; $P<0.0001$, chi-square test]. Gene loci of tumor necrosis factor α gene and platelet-activating factor acetylhydrolase gene were in proximity to each other, but no relationship was found in distribution of the genotype of polymorphisms of the both genes. Similarly, gene loci of plasminogen activator inhibitor 1 gene and paraoxonase were in proximity to each other, but no relationship was found in distribution of the genotype of polymorphisms of the both genes.

The odds ratio of contraction with myocardial infarction by the combination of the genotype calculated by the stepwise forward selection method was shown in FIG. 11 and FIG. 13(A) as to males, and in FIG. 12 and FIG. 13(B) as to females. In males, maximum odds ratio was 4.50 in the genotype combination of five SNPs (TSP4 (1186G→C) polymorphism, connexin 37 (1019C→T) polymorphism, PAF acetylhydrolase (994G→T) polymorphism, angiotensinogen (−6G→A) polymorphism, tumor necrosis factor α (−863C→A) polymorphism) (see FIG. 11 and FIG. 13(A)). In the case where further five SNPs (SNP (NADH/NADPH oxidase p22 phox (242C→T) polymorphism, Apo E (−219G→T) polymorphism, Apo C-III (−482C→T) polymorphism, IL-10 (−819T→C) polymorphism, IL-10 (−592A→C) polymorphism) were added and SNPs are 10 in total, maximum odds ratio was 11.26 (see FIG. 10 and FIG. 13(A)). In females, by the combination of five SNP (Apo E (4070C→T) polymorphism, glycoprotein Ibα (1018C→T) polymorphism, stromelysin 1 (−1171/5A.6A) polymorphism, PAIL (−668/4G-5G) polymorphism, paraoxonase (584G→A) polymorphism)), maximum odds ratio was 88.51 (see FIG. 12 and FIG. 13(B)).

As mentioned above, the present inventors have investigated the relationship between myocardial infarction and 112 polymorphisms which were selected from 71 candidate genes; and identified 10 SNPs (in males) and five SNPs (in females) which were associated with myocardial infarction by way of a large scale association study of 5061 cases. Furthermore, by the stepwise forward selection method of multivariate logistic regression analysis, a method for diagnosing the risk of myocardial infarction (genetic risk diagnostic system) presenting the maximum odds ratio of 11.26 in males and maximum odds ratio of 88.51 was developed.

Main causes of myocardial infarction is arteriosclerotic coronary artery disease, which may cause hemodynamically significant stenosis in the internal diameter of artery to cause abnormalities in regulation of vasoconstriction and vasodilator action. As a result, rupture of arterial sclerosis lesion or thrombogenesis is likely to occur. The present inventors have selected 71 candidate genes based on the comprehensive viewpoint including vascular biology, platelet-leukocyte biology, coagulation and fibrinolysis system, a metabolic factor such as lipid, sugar, etc. In fact, a group of genes related to myocardial infarction had various roles in development condition. That is to say, vascular biology (connexin 37, NADH/NADPH oxidase p22 phox, and thrombospondin 4), vascular inflammation (tumor necrosis factor-α, platelet-activating factor acetylhydrolase, and interleukin-10), hypertension (angiotensinogen), lipid metabolism (apolipoprotein E and C-III and paraoxonase), function of platelet (glycoprotein Ibα), matrix metabolism (stromelysin-1), fibrinolytic system (PAI-1), and the like, are included (Boerma M, Forsberg L, van Zeijl L, et al. A genetic polymorphism in connexin 37 as a prognostic marker for atherosclerotic plaque development. J Intern Med 1999;246: 211-218, Inoue N, Kawashima S, Kanazawa K, Yamada S, Akita H, Yokoyama M. Polymorphism of the NADH/NADPH oxidase p22 phox gene in patients with coronary artery disease. Circulation 1998;97: 135-137, Topol E J, McCarthy J, Gabriel S, et al. Single nucleotide polymorphisms in multiple novel thrombospondin genes may be associated with familial premature myocardial infarction. Circulation 2001;104: 2641-2644, Skoog T, van't Hooft F M, Kallin B, et al. A common functional polymorphism (C→A substitution at position −863) in the promoter region of the tumor necrosis factor-α (TNF-α) gene associated with reduced circulating level of TNF-α. Hum Mol Genet 1999;8: 1443-1449, Yamada Y, Ichihara S, Fujimura T, Yokota M. Identification of the $G^{994} \rightarrow T$ missense mutation in exon 9 of the plasma platelet-activating factor acetylhydrolase gene as an independent risk factor for coronary artery disease in Japanese men. Metabolism 1998;47: 177-181, Koch W, Kastrati A, Bottiger C, Mehilli J, von Beckerath N, Schomig A. Interleukin-10 and tumor necrosis factor gene polymorphisms and risk of coronary artery disease and myocardial infarction. Atherosclerosis 2001;159: 137-144, Inoue I, Nakajima T, Williams C S, et al. A nucleotide substitution in the promoter of human angiotensinogen is associated with essential hypertension and affects basal transcription in vitro. J Clin Invest 1997;99: 1786-1797, Lambert J-C, Brousseau T, Defosse V, et al. Independent association of an APOE gene promoter polymorphism with increased risk of myocardial infarction and decreased APOE plasma concentrations-the ECTIM study. Hum Mol Genet 2000;9: 57-61, Eto M, Watanabe K, Makino I. Increased frequency of apolipoprotein epsilon 2 and epsilon 4 alleles in patients with ischemic heart disease. Clin Genet 1989;36: 183-188., Ruiz J, Blanche H, James R W, et al. Gln-Arg192 polymorphism of paraoxonase and coronary heart disease in type 2 diabetes. Lancet 1995;346: 869-72, Murata M, Matsubara Y, Kawano K, et al. Coronary artery disease and polymorphisms in a receptor mediating shear stress-dependent platelet activation. Circulation 1997;96: 3281-3286, Eriksson P, Kallin B, van't Hooft F M, Bavenholm P, Hamsten A. Allele-specific increase in basal transcription of the plasminogen-activator inhibitor 1 gene is associated with myocardial infarction. Proc Natl Acad Sci USA 1995;92: 1851-1855, Ye S, Watts G F, Mandalia S, Humphries S E, Henney A M. Preliminary report: genetic variation in the human stromelysin promoter is associated with progression of coronary atyheroscloersis. Br Heart J 1995; 73: 209-215). The present inventors have investigated 112 gene polymorphisms in 909 cases and investigated 19 SNPs in 2858 male cases and 18 SNPs in 1294 female cases. As a result, the present inventors determined 179,402 genotypes in total. The number of determined genes is the largest among those reported previously in the last relation analysis of gene polymorphisms. The method for diagnosing the risk of myocardial infarction shown in the above-mentioned Examples had maximum odds ratio of 11.26 in males and 88.51 in females, which are also maximum among those in the previously reported relation analysis.

In 15 SNPs associated with myocardial infarction, 4070T-C (Arg158Cys) polymorphism of the apolipoprotein E gene exhibited a maximum odds ratio as female myocardial infarction. Apolipoprotein E is a main component of chylomicron and very low density lipoprotein (VLDL) remnant and functions as ligand when these lipoporoteins are taken by receptors in the liver (Mahley R W. Apolipoprotein E: cholesterol transport protein with expanding role in cell biology. Science 1998;240: 622-630). 158Cys (e2) allele of apolipoprotein E gene causes abnormal binding to the receptor in the liver (Schneider W J, Kovanen P T, Brown M S, et al. Familial dysbetalipoproteinemia. Abnormal binding of mutant apolipoprotein E to low density lipoprotein receptors of human fibroblasts and membranes from liver and adrenal of rats, rabbits, and cows. J Clin Invest 1981;68: 1075-1085), and the removal from plasma is delayed (Gregg R E, Zech L A, Schaefer E J, Brewer H B Jr. Type III hyperlipoproteinemia: defective metabolism of an abnormal apolipoprotein E. Science 1981;211: 584-586). Most of familial dysbetalipoproteinemia (FD, or III type hyperlipoproteinemia) patients have homozygote of Arg158Cys polymorphism (Breslow J L, Zannis V I, SanGiacomo T R, Third J L, Tracy T, Glueck C J. Studies of familial type III hyperlipoproteinemia using as a genetic marker the apo E phenotype E2/2. J Lipid Res 1982; 23: 1224-1235). However, since only 1% to 4% of 158Cys/Cys homozygote develops familial dysbetalipoproteinemia, it is thought that other genetic factors or environmental factors are necessary to this disease. Accumulation of arteriosclerosis remnant lipoprotein (β-VLDL) in plasma in familial dysbetalipoproteinemia patients (Mahley R W. Apolipoprotein E: cholesterol transport protein with expanding role in cell biology. Science 1998;240: 622-630) or a mouse overexpressing human 158Cys/Cys (Sullivan P M, Mezdour H, Quarfordt S H, Maeda N. Type III hyperlipoproteinemia and spontaneous atherosclerosis in mice resulting from gene replacement of mouse Apoe with human APOE*2. J Clin Invest 1998;102: 130-135) is found to promote the development of arteriosclerosis. Eto et al. have reported that e2 (158Cys) allele is associated with coronary artery disease in Japanese males (odds ratio=2.44, e2 allele pair, e3/e3 type) and females (odds ratio=3.03) (Eto M, Watanabe K, Makino I. Increased frequency of apolipoprotein epsilon 2 and epsilon 4 alleles in patients with ischemic heart disease. Clin Genet 1989;36: 183-188). The conclusion of the present inventors that TT type (158Cys/Cys) is a risk factor for myocardial infarction agrees with the conclusion of Eto et al.

Some of SNPs investigated in the above-mentioned Examples may be in a linkage disequilibrium with SNPs of genes actually associated with the development of myocardial infarction existing in the vicinity thereof. However, nine genes in male and five genes in females are shown to be susceptible gene loci of myocardial infarction. Furthermore, combination of genotypes enables high reliable and predictability diagnostic method. Thus, diagnostic method of the present invention can be expected to contribute to primary prevention of myocardial infarction and the improvement in quality of life of middle and old aged persons as well as the reduction of health care cost.

The present invention is not limited to the description of the above embodiments. A variety of modifications, which are within the scopes of the following claims and which are achieved easily by a person skilled in the art, are included in the present invention.

Hereinafter, the following matters are disclosed.

11. A method for detecting the genotype, comprising the following step (a1),
   (a1) analyzing the following polymorphisms (1) to (10) in a nucleic acid sample:
   (1) polymorphism at the base number position 1019 of the connexin 37 gene;
   (2) polymorphism at the base number position -863 of the tumor necrosis factor α gene;
   (3) polymorphism at the base number position 242 of the NADH/NADPH oxidase p22 phox gene;
   (4) polymorphism at the base number position -6 of the angiotensinogen gene;
   (5) polymorphism at the base number position -219 of the apolipoprotein E gene;
   (6) polymorphism at the base number position 994 of the platelet-activating factor acetylhydrolase gene;
   (7) polymorphism at the base number position -482 of the apolipoprotein C-III gene;
   (8) polymorphism at the base number position 1186 of the thrombospondin 4 gene;
   (9) polymorphism at the base number position -819 of the interleukin-10 gene; and
   (10) polymorphism at the base number position -592 of the interleukin-10 gene.

12. A method for detecting the genotype, comprising the following step (b1),
   (b1) analyzing the following polymorphisms (11) to (15) in a nucleic acid sample:
   (11) polymorphism at the base number position -1171 of the stromelysin 1 gene;
   (12) polymorphism at the base number position -668 of the plasminogen activator inhibitor-1 gene;
   (13) polymorphism at the base number position 1018 of the glycoprotein Ibα gene;
   (14) polymorphism at the base number position 584 of the paraoxonase gene: and
   (15) polymorphism at the base number position 4070 of the apolipoprotein E gene.

13. A method for diagnosing the risk of myocardial infarction, comprising the following (i) to (iii):
   (i) a step of analyzing the following polymorphisms (1) to (10) in a nucleic acid sample:
   (1) polymorphism at the base number position 1019 of the connexin 37 gene;
   (2) polymorphism at the base number position -863 of the tumor necrosis factor α gene;
   (3) polymorphism at the base number position 242 of the NADH/NADPH oxidase p22 phox gene;
   (4) polymorphism at the base number position -6 of the angiotensinogen gene:
   (5) polymorphism at the base number position -219 of the apolipoprotein E gene;
   (6) polymorphism at the base number position 994 of the platelet-activating factor acetylhydrolase gene;
   (7) polymorphism at the base number position -482 of the apolipoprotein C-III gene;
   (8) polymorphism at the base number position 1186 of the thrombospondin,4 gene;
   (9) polymorphism at the base number position -819 of the interleukin-10 gene; and
   (10) polymorphism at the base number position -592 of the interleukin-10 gene;
   (ii) determining, based on the information about polymorphism which was obtained in the step (i), the genotype of the nucleic acid sample; and (iii) assessing, based on the genotype determined, a genetic risk of myocardial infarction.

14. A method for diagnosing the risk of myocardial infarction, comprising the following steps (iv) to (vi):
    (iv) a step of analyzing the following polymorphisms (11) to (15) in a nucleic acid sample:
        (11) polymorphism at the base number position −1171 of the stromelysin 1 gene;
        (12) polymorphism at the base number position −668 of the plasminogen activator inhibitor-1 gene;
        (13) polymorphism at the base number position 1018 of the glycoprotein Ibα gene;
        (14) polymorphism at the base number position 584 of the paraoxonase gene: and
        (15) polymorphism at the base number position 4070 of the apolipoprotein E gene.
    (v) determining, based on the information about polymorphism which was obtained in the step (iv), the genotype of the nucleic acid sample; and
    (vi) assessing, based on the genotype determined, a genetic risk of myocardial infarction.

INDUSTRIAL APPLICABILITY

According to the present invention, gene polymorphisms associated with myocardial infarction are analyzed and the genotypes of nucleic acid sample are detected. By using the information about polymorphisms obtained by the detection of the genotypes, diagnosis of the risk of myocardial infarction with high accuracy and high predictability can be carried out. Therefore, the present invention is an effective means for understanding the risk of development of myocardial infarction in advance. Furthermore, according to the present invention, auxiliary information useful for diagnosing the disease is obtained, thus enabling more appropriate treatment and improvement of prognosis. In addition, the present invention provides information useful in clarifying the development mechanism of myocardial infarction and is expected to contribute to prevention and treatment of myocardial infarction.

The invention claimed is:

1. A method for diagnosing the risk of myocardial infarction, comprising the following steps (i) to (iii):
   (i) analyzing two polymorphisms (1) and (2) in a nucleic acid sample:
      (1) polymorphism at the base number position 1019 of the connexin 37 gene; and
      (2) polymorphism at the base number position 242 of the NADH/NADPH oxidase p22 phox gene;
   (ii) determining, based on the information about said polymorphism which was obtained in the step (i), the genotype of the nucleic acid sample; and
   (iii) assessing, based on the genotype determined, a genetic risk of myocardial infarction.

* * * * *